United States Patent
Haas et al.

(10) Patent No.: US 8,513,263 B2
(45) Date of Patent: Aug. 20, 2013

(54) SUBSTITUTED PYRAZOLO[1,5-A]PYRIMIDINE COMPOUNDS AS TRK KINASE INHIBITORS

(75) Inventors: Julia Haas, Boulder, CO (US); Steven W. Andrews, Boulder, CO (US); Yutong Jiang, Boulder, CO (US); Gan Zhang, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 63 days.

(21) Appl. No.: 13/125,263

(22) PCT Filed: Oct. 21, 2009

(86) PCT No.: PCT/US2009/061519
§ 371 (c)(1),
(2), (4) Date: Apr. 20, 2011

(87) PCT Pub. No.: WO2010/048314
PCT Pub. Date: Apr. 29, 2010

(65) Prior Publication Data
US 2011/0195948 A1    Aug. 11, 2011

Related U.S. Application Data

(60) Provisional application No. 61/107,616, filed on Oct. 22, 2008.

(51) Int. Cl.
*A01N 43/90* (2006.01)
*A61K 31/519* (2006.01)
*C07D 487/00* (2006.01)

(52) U.S. Cl.
USPC ........................ 514/259.3; 544/281

(58) Field of Classification Search
None
See application file for complete search history.

(56) References Cited

FOREIGN PATENT DOCUMENTS

| | | |
|---|---|---|
| WO | WO 03/080064 A1 | 10/2003 |
| WO | 2004/022561 A1 | 3/2004 |
| WO | 2004/087707 A1 | 10/2004 |
| WO | 2004/089415 A2 | 10/2004 |
| WO | 2004/089471 A2 | 10/2004 |
| WO | 2006/087538 A1 | 8/2006 |
| WO | 2006/115452 A1 | 11/2006 |
| WO | 2007/013673 A1 | 2/2007 |
| WO | WO 2007/024680 A1 | 3/2007 |
| WO | 2007/038314 A2 | 4/2007 |
| WO | 2007/044449 A2 | 4/2007 |
| WO | 2007/048066 A2 | 4/2007 |
| WO | WO 2007/084815 A2 | 7/2007 |
| WO | WO 2007/102679 A1 | 9/2007 |
| WO | WO 2007/129161 A2 | 11/2007 |
| WO | 2008/037477 A1 | 4/2008 |
| WO | 2008/052734 A1 | 5/2008 |
| WO | WO 2008/115974 A2 | 9/2008 |
| WO | WO 2009/052145 A1 | 4/2009 |
| WO | WO 2010/033941 A1 | 3/2010 |
| WO | 2010/048314 A1 | 4/2010 |
| WO | 2010/051549 A1 | 5/2010 |

OTHER PUBLICATIONS

Int'l Search Report and Written Opinion Corresponding to Related Application No. PCT/US2009/061519.
Wang et al., "Trk kinase inhibitors as new treatments for cancer and pain", Expert Opin. Ther. Patents, 2009, pp. 305-319, vol. 19(3).

*Primary Examiner* — Jeffrey Murray
(74) *Attorney, Agent, or Firm* — John R. Moore, Esq.; Sarah S. Mastous; Viksnins Harris & Padys PLLP

(57) ABSTRACT

Compounds of Formula (I) in which $R^1$, $R^2$, $R^3$, $R^4$, X, Y and n have the meanings given in the specification, are inhibitors of Trk kinases and are useful in the treatment of diseases which can be treated with a Trk kinase inhibitor.

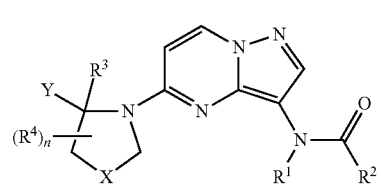

(I)

30 Claims, No Drawings

SUBSTITUTED PYRAZOLO[1,5-A]PYRIMIDINE COMPOUNDS AS TRK KINASE INHIBITORS

The present invention relates to novel compounds, to pharmaceutical compositions comprising the compounds, to a process for making the compounds and to the use of the compounds in therapy. More particularly, it relates to certain substituted pyrazolo[1,5-a]pyrimidine compounds which exhibit Trk family protein tyrosine kinase inhibition, and which are useful in the treatment of pain, inflammation, cancer, and certain infectious diseases.

The current treatment regimes for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members—TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., Current Opinion in Neurobiology, 2001, 11, 272-280).

Inhibitors of the Trk/neurotrophin pathway have been demonstrated to be effective in numerous pre-clinical animal models of pain. For example, antagonistic NGF and TrkA antibodies (for example, RN-624) have been shown to be efficacious in inflammatory and neuropathic pain animal models and in human clinical trials (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448). Additionally, recent literature indicates after inflammation, BDNF levels and TrkB signaling is increased in the dorsal root ganglion (Cho, L. et al. Brain Research 1997, 749, 358) and several studies have show antibodies that decrease signaling through the BDNF/TrkB pathway inhibit neuronal hypersensitization and the associated pain (Chang-Qi, L et al. Molecular Pain 2008, 4:27).

In addition, it has been shown that tumor cell sand tumor invading macrophages directly stimulates TrkA located on peripheral pain fibers. Using various tumor models in both mice and rats it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., J. Physiol. 2005, 569:685-95), neuropathic pain (Thompson, S. W., Proc. Natl. Acad. Sci. USA 1999, 96:7714-18) and surgical pain (Li, C.-Q. et al., Molecular Pain, 2008, 4(28), 1-11). Because TrkA and TrkB kinases may serve as a mediator of NGF driven biological responses, inhibitors of TrkA and/or other Trk kinases may provide an effective treatment for chronic pain states.

Recent literature has also shown that overexpression, activation, amplification and/or mutation of Trk's are associated with many cancers including neuroblastoma (Brodeur, G. M., Nat. Rev. Cancer 2003, 3, 203-216), ovarian cancer (Davidson. B., et al., Clin. Cancer Res. 2003, 9, 2248-2259), breast cancer (Kruettgen et al, Brain Pathology 2006, 16: 304-310), prostate cancer (Dionne et al, Clin. Cancer Res. 1998, 4(8): 1887-1898), pancreatic cancer (Dang et al, Journal of Gastroenterology and Hepatology 2006, 21(5): 850-858), multiple myeloma (Hu et al, Cancer Genetics and Cytogenetics 2007, 178: 1-10), astrocytoma and medulloblastoma (Kruettgen et al, Brain Pathology 2006, 16: 304-310) glioma (Hansen et al, Journal of Neurochemistry 2007, 103: 259-275), melanoma (Truzzi et al, Journal of Investigative Dermatology 2008, 128(8): 2031-2040, thyroid carcinoma (Brzezianska et al, Neuroendocrinology Letters 2007, 28(3), 221-229.), lung adenocarcinoma (Perez-Pinera et al, Molecular and Cellular Biochemistry 2007, 295(1&2), 19-26), large cell neuroendocrine tumors (Marchetti et al, Human Mutation 2008, 29(5), 609-616), and colorectal cancer (Bardelli, A., Science 2003, 300, 949). In preclinical models of cancer, Trk inhibitors are efficacious in both inhibiting tumor growth and stopping tumor metastasis. In particular, non-selective small molecule inhibitors of Trk A, B and C and Trk/Fc chimeras were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E. et al. *Cancer Res* (2008) 68:(2) 346-351) (Truzzi et al, Journal of Investigative Dermatology 2008, 128(8): 2031-2040. Therefore, an inhibitor of the Trk family of kinases is expected to have utility in the treatment of cancer.

In addition, inhibition of the neurotrophin/Trk pathway has been shown to be effective in treatment of pre-clinical models of inflammatory diseases. For example, inhibition of the neurotrophin/Trk pathway has been implicated in preclinical models of inflammatory lung diseases including asthma (Freund-Michel, V; Frossard, N.; *Pharmacology & Therapeutics* (2008), 117(1), 52-76), interstitial cystitis (Hu Vivian Y; et. al. *The Journal of Urology* (2005), 173(3), 1016-21), inflammatory bowel diseases including ulcerative colitis and Crohn's disease (Di Mola, F. F, et. al., Gut (2000), 46(5), 670-678) and inflammatory skin diseases such as atopic dermatitis (Dou, Y.-C.; et. al. *Archives of Dermatological Research* (2006), 298(1), 31-37), eczema and psoriasis (Raychaudhuri, S. P.; et. al. Journal of Investigative Dermatology (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's disease (Sohrabji, Farida; Lewis, Danielle K. Frontiers in Neuroendocrinology (2006), 27(4), 404-414). Modulation of the neutrophin/Trk pathway may have utility in treatment of these and related diseases.

The TrkA receptor is also thought to be critical to the disease process in the infection of the parasitic infection of *Typanosoma cruzi* (Chagas disease) in human hosts (de Melo-Jorge, M. et al. *Cell Host & Microbe* (2007), 1(4), 251-261). Thus, TrkA inhibition my have utility in treating Chagas disease and related protozoan infections.

Trk inhibitors may also find use in treating disease related to an imbalance of the regulation of bone remodeling, such as osteoporosis, rheumatoid arthritis, and bone metastases.

Bone metastases are a frequent complication of cancer, occurring in up to 70 percent of patients with advanced breast or prostate cancer (1) and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3)).

International Patent Application Publications WO 2006/115452 and WO 2006/087538 describe several classes of small molecules said to be inhibitors or Trk kinases which could be useful for treating pain or cancer.

Pyrazolo[1,5-a]pyrimidine compounds are known. For example, International Patent Application Publication WO 2008/037477 discloses pyrazolo[1,5-a]pyrimidine compounds bearing an alkyl, aryl or heterocyclic group at the 3-position. These compounds are asserted to be PI3K and/or mTOR Lipid Kinase inhibitors.

International Patent Application Publication WO 2008/058126 discloses pyrazolo[1,5-a]pyrimidine compounds bearing a phenyl group at the 3-position. These compounds are asserted to be Pim-kinase inhibitors.

U.S. Publication US 2006/0094699 discloses pyrazolo[1,5-a]pyrimidine compounds bearing a —C(=O)NH-phenyl, —C(=O)(4-methylpiperidinyl) or —C(=O)NMe(CH$_2$-trimethylpyrazolyl) group at the 3-position for use in combination therapy with a glucocorticoid receptor agonist.

It has now been found that certain pyrazolo[1,5-a]pyrimidine compounds bearing an aryl or heteroaryl-substituted heterocyclic group at the 5-position and a group having the formula NR$^1$C(=O)R$^2$ at the 3-position, wherein R$^1$ and R$^2$ are as defined herein, are inhibitors of Trk kinases, in particular inhibitors of TrkA and/or TrkB, which are useful for treating disorders and diseases which can be treated by inhibiting TrkA and/or TrkB kinases, such as pain, including chronic and acute pain, or cancer. Certain compounds which are dual inhibitors of TrkA and TrkB may be useful in the treatment of multiple types of pain including inflammatory pain, neuropathic pain, surgical pain, and pain associated with cancer, surgery and bone fracture. Selectivity for TrkA and/or TrkB is particularly desirable in compounds for use in treating pain. In addition, compounds of the invention may be useful for treating cancer, inflammation, neurodegenerative diseases and certain infectious diseases.

Accordingly, one embodiment of this invention provides a compound of the general Formula I:

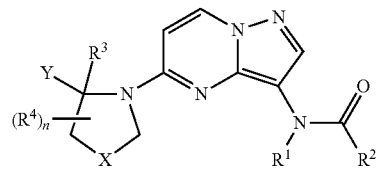

or a pharmaceutically acceptable salt thereof, wherein:

R$^1$ is H or (1-6C alkyl);

R$^2$ is NR$^b$R$^c$, (1-4C)alkyl, (1-4C)fluoroalkyl, CF$_3$, (1-4C)hydroxyalkyl, -(1-4C alkyl)hetAr$^1$, -(1-4C alkyl)NH$_2$, -(1-4C alkyl)NH(1-4C alkyl), -(1-4C alkyl)N(1-4C alkyl)$_2$, hetAr$^2$, hetCyc$^1$, hetCyc$^2$, phenyl which is optionally substituted with NHSO$_2$(1-4C alkyl), or (3-6C)$^e$cycloalkyl which is optionally substituted with (1-4C alkyl), CN, OH, OMe, NH$_2$, NHMe, N(CH$_3$)$_2$, F, CF$_3$, CO$_2$(1-4C alkyl), CO$_2$H, C(=O)NR$^e$R$^f$ or C(=O)OR$^g$;

R$^b$ is H or (1-6C alkyl);

R$^c$ is H, (1-4C)alkyl, (1-4C)hydroxyalkyl, hetAr$^3$, or phenyl, wherein said phenyl is optionally substituted with one or more substituents independently selected from halogen, CN, CF$_3$ and —O(1-4C alkyl), or NR$^b$R$^c$ forms a 4 membered heterocyclic ring having a ring nitrogen atom wherein said heterocyclic ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl, or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo, or NR$^b$R$^c$ forms a 7-8 membered bridged heterocyclic ring having a ring nitrogen atom and optionally having a second ring heteroatom selected from N and O, wherein said ring is optionally substituted with CO$_2$(1-4C alkyl);

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4C)alkoxy, and NH(1-4C alkyl);

hetCyc$^1$ is a carbon-linked 4-6 membered azacyclic ring optionally substituted with one or more substituents independently selected from (1-4C alkyl), and CO$_2$(1-4C alkyl);

hetCyc$^2$ is a pyridinone or pyridazinone ring which is optionally substituted with a substituent selected from (1-4C) alkyl;

hetAr$^3$ is a 5-6 membered heteroaryl ring having 1-2 ring heteroatoms independently selected from N and O and optionally substituted with one or more substituents independently selected from (1-4C)alkyl;

R$^e$ is H or (1-4C)alkyl;

R$^f$ is H, (1-4C)alkyl, or (3-6C)cycloalkyl;

or NR$^e$R$^f$ forms a 5-6-membered azacyclic ring optionally having an additional ring heteroatom selected from N and O, wherein the azacyclic ring is optionally substituted with OH;

R$^g$ is H or (1-6C)alkyl;

Y is (i) phenyl optionally substituted with one or more substituents independently selected from halogen, (1-4C) alkoxy, $CF_3$ and $CHF_2$, or (ii) a 5-6 membered heteroaryl ring having a ring heteroatom selected from N and S, wherein said heteroaryl ring is optionally substituted with one or more halogen atoms;

X is null, —$CH_2$—, —$CH_2CH_2$—, —$CH_2O$— or —$CH_2NR^d$—;

$R^d$ is H or (1-4C alkyl);

$R^3$ is H or (1-4C alkyl);

each $R^4$ is independently selected from halogen, (1-4C) alkyl, OH, (1-4C)alkoxy, $NH_2$, NH(1-4C alkyl) and $CH_2OH$; and n is 0, 1, 2, 3, 4, 5 or 6.

In certain embodiments of Formula I, $R^2$ is selected from any of the values described above, other than C(=O)$NR^eR^f$ or C(=O)$OR^g$.

In certain embodiments of Formula I, $R^1$ is hydrogen.

In certain embodiments of Formula I, $R^1$ is (1-6C)alkyl. A particular example is methyl.

In certain embodiments of Formula I, $R^2$ is a group having the formula $NR^bR^c$, such that the group at the 3 position of the pyrazolo[1,5-a]pyrimidine core of Formula I has the formula —$NR^1C(=O)NR^bR^c$.

In certain embodiments, $R^b$ is H or (1-6C alkyl).

In certain embodiments, $R^b$ is H. In certain embodiments, $R^b$ is (1-6C alkyl), for example Me.

In certain embodiments, $R^2$ is $NR^bR^c$ where $R^c$ is H, (1-4C) alkyl, (1-4C)hydroxyalkyl, $hetAr^3$, or phenyl, wherein said phenyl is optionally substituted with one or more substituents independently selected from halogen, CN, $CF_3$ and —O(1-4C alkyl).

In certain embodiments, $R^2$ is $NR^bR^c$, where $R^c$ is hydrogen. In particular embodiments, the group represented by $NR^bR^c$ is $NH_2$.

In certain embodiments, $R^2$ is $NR^bR^c$, where $R^c$ is (1-4C) alkyl. Examples include methyl, ethyl, propyl, isopropyl, butyl, isobutyl, and the like. In particular embodiments, the group represented by $NR^bR^c$ includes NHMe, $NMe_2$ and NH(t-butyl).

In certain embodiments, $R^2$ is $NR^bR^c$, where $R^c$ is (1-4C) hydroxyalkyl. Examples include $CH_2CH_2OH$ and $CH_2CH_2CH_2OH$. In particular embodiments, the group represented by $NR^bR^c$ includes NMe($CH_2CH_2OH$).

In certain embodiments, $R^2$ is $NR^bR^c$, where $R^c$ is $hetAr^3$, and $hetAr^3$ is an optionally substituted 5-6 membered heteroaryl ring having 1-2 ring heteroatoms independently selected from N and O. An example of $hetAr^3$ includes an isoxazolyl ring. In certain embodiments, $hetAr^3$ is unsubstituted. In other embodiments, $hetAr^3$ is substituted with one or more substituents independently selected from (1-4C)alkyl, for example one or more substituents independently selected from methyl and ethyl. Examples of $hetAr^3$ include dimethylisoxazolyl. In particular embodiments, the group represented by $NR^bR^c$ includes the group having the structure:

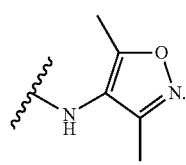 [SMILES: *Nc1c(C)noc1C]

In certain embodiments, $R^2$ is $NR^bR^c$, where $R^c$ is a phenyl group optionally substituted with one or more substituents independently selected from halogen, CN, $CF_3$ and 0-(1-4C) alkyl). Examples of $R^c$ include phenyl, fluorophenyl, chlorophenyl, cyanophenyl, methoxyphenyl, trifluoromethylphenyl, dichlorophenyl, and trimethoxyphenyl. More particular examples include 4-fluorophenyl, 3-chlorophenyl, 4-chlorophenyl, 3-cyanophenyl, 4-cyanophenyl, 4-methoxyphenyl, 2-4-dichlorophenyl, 3-(trifluoromethyl)phenyl, 3,5-dichlorophenyl, and 3,4,5-trimethoxyphenyl. In particular embodiments, the group represented by $NR^bR^c$ includes the structures:

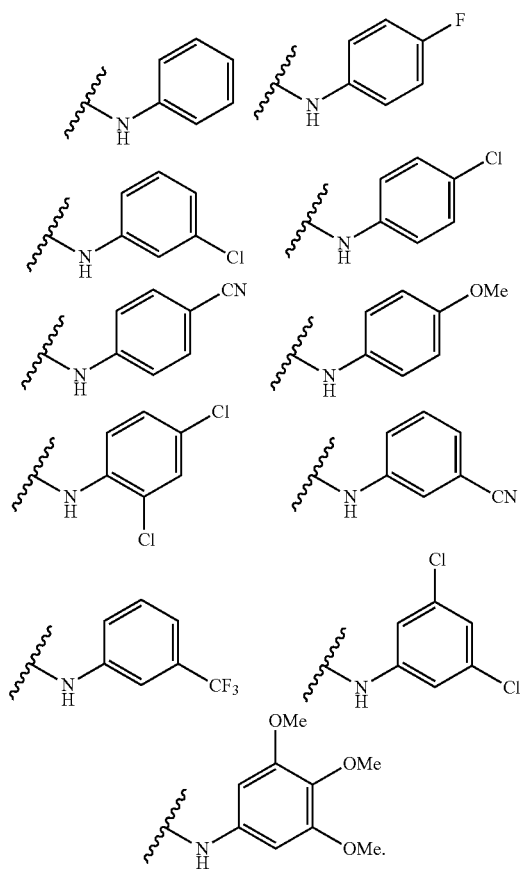

In certain embodiments, $R^2$ is $NR^bR^c$ where $R^c$ is selected from H, Me, t-butyl, $CH_2CH_2OH$ and $CH_2CH_2CH_2OH$, dimethylisoxazolyl, phenyl, fluorophenyl, chlorophenyl, cyanophenyl, methoxyphenyl, trifluoromethylphenyl, dichlorophenyl, and trimethoxyphenyl. More particular examples include 4-fluorophenyl, 3-chlorophenyl, 4-chlorophenyl, 3-cyanophenyl, 4-cyanophenyl, 4-methoxyphenyl, 2-4-dichlorophenyl, 3-(trifluoromethyl)phenyl, 3,5-dichlorophenyl, and 3,4,5-trimethoxyphenyl. In one embodiment, $R^b$ is H. In one embodiments, $R^b$ is (1-6C alkyl), for example methyl.

In certain embodiments, $R^2$ is —$NR^bR^c$, wherein:

(i) $NR^bR^c$ forms a 4 membered heterocyclic ring having a ring nitrogen atom, wherein said ring is optionally substituted with one or more substituents independently selected from halogen, OH, (1-4C alkyl), (1-4C)alkoxy, —OC(=O)(1-4C alkyl), $NH_2$, —NHC(=O)O(1-4C alkyl) and (1-4C)hydroxyalkyl, or (ii) $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo, or (iii) $NR^bR^c$ forms a 7-8 membered bridged heterocyclic ring having a ring nitrogen atom and optionally having a second ring heteroatom selected from N and O, wherein said ring is optionally substituted with $CO_2$(1-4C alkyl).

In certain embodiments, $R^2$ is $—NR^bR^c$, wherein $—NR^bR^c$ forms a 4 membered heterocyclic ring having a ring nitrogen atom, wherein said ring is optionally substituted with one or more substituents independently selected from halogen, OH, (1-4C alkyl), —O(1-4C alkyl), —OC(=O)(1-4C alkyl), $NH_2$, —NHC(=O)O(1-4C alkyl) and (1-4C)hydroxyalkyl. Examples include azetidinyl rings optionally substituted with one or more substituents independently selected from F, OH, methyl, OMe, $OC(=O)C(CH_3)_2$, $NH_2$, —NHC(=O)OC$(CH_3)_3$ and $CH_2OH$. Particular examples of $R^2$ when represented by —$NR^bR^c$, wherein —$NR^bR^c$ forms a 4 membered heterocyclic ring, include the structures:

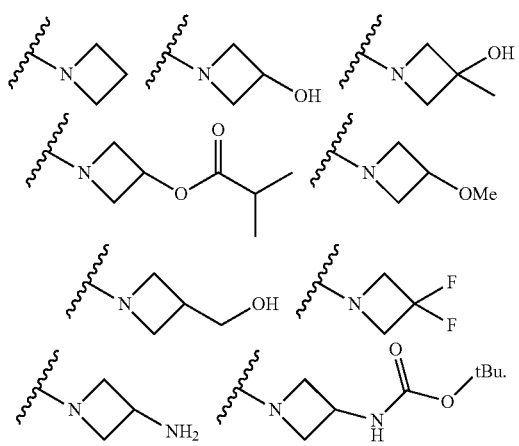

In certain embodiments, $R^2$ is —$NR^bR^c$, wherein —$NR^bR^c$ forms a 4 membered azacyclic ring optionally substituted with one or two substituents independently selected from OH, (1-4C alkyl), and —O(1-4C alkyl), for example OH, Me and OMe.

In certain embodiments, $R^2$ is —$NR^bR^c$, wherein —$NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo. Examples include optionally substituted pyrrolidinyl, piperidinyl, piperazinyl, morpholinyl and piperidinesulfone rings. Examples of substituents on the 5-6 membered heterocyclic ring include OH, F, $NH_2$, $CO_2H$, $CO_2Et$, $NHCO_2C(CH_3)_3$, $CF_3$, methyl, ethyl, isopropyl, $CO_2C(CH_3)_3$ and oxo. In one embodiment, the heterocyclic ring is optionally substituted with one or two of said substituents. Particular examples of $R^2$ when represented by —$NR^bR^c$, wherein —$NR^bR^c$ forms a 5-6 membered heterocyclic ring, include the structures:

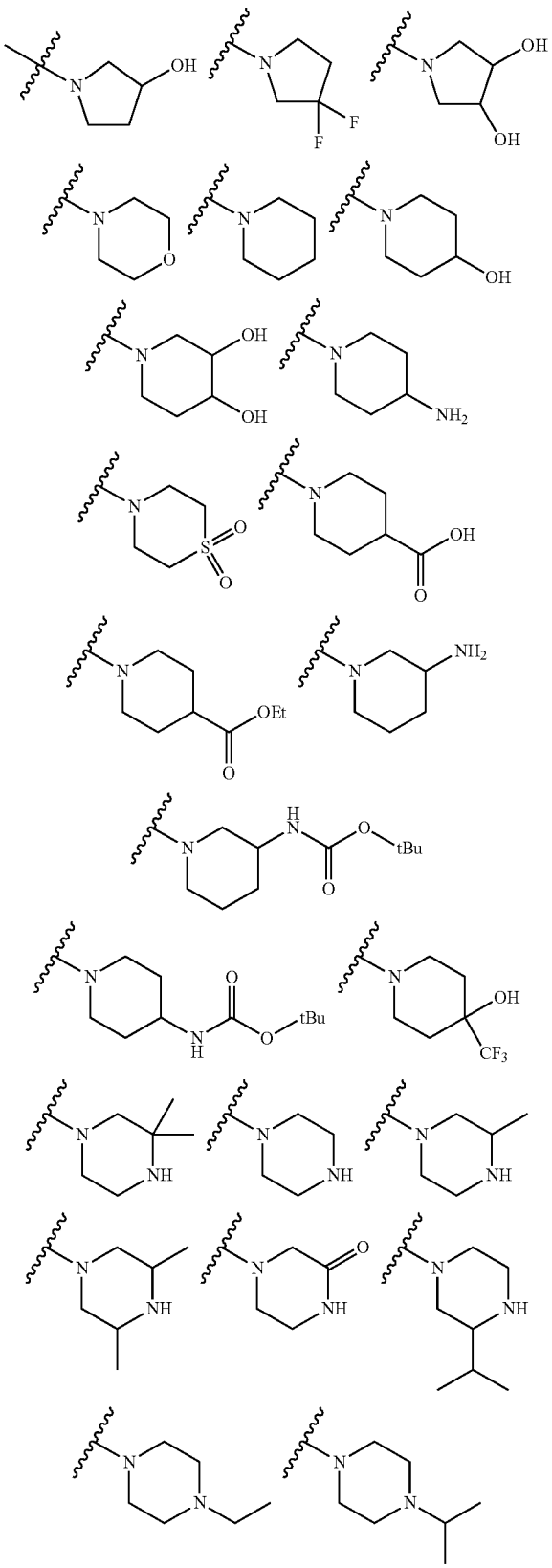

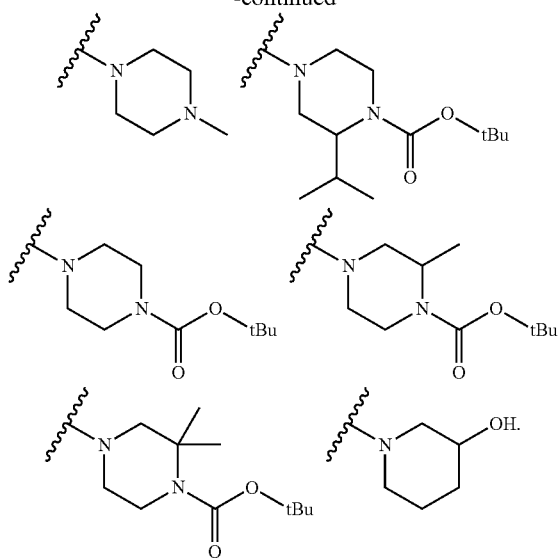

In certain embodiments, $R^2$ is —$NR^bR^c$, wherein —$NR^bR^c$ forms a 5-membered heterocyclic ring optionally substituted with one or two substituents independently selected from OH and (1-4C) alkyl, for example OH and Me. In certain embodiments, —$NR^bR^c$ forms an azacyclic ring optionally substituted with one to two substituted independently selected from OH and Me.

In certain embodiments, $R^2$ is —$NR^bR^c$, wherein —$NR^bR^c$ forms a 6-membered heterocyclic ring optionally substituted with one or two substituents independently selected from OH and (1-4C) alkyl, for example OH and Me.

In certain embodiments, $R^2$ is —$NR^bR^c$, wherein $NR^bR^c$ forms a 7-8 membered bridged heterocyclic ring having a ring nitrogen atom and optionally having a second ring heteroatom selected from N and O, wherein said ring is optionally substituted with $CO_2$(1-4C alkyl). Examples of bridged heterocyclic rings include diazabicyclooctane rings such as 3,8-diazabicyclo[3.2.1]octane and oxa-azabicyclo[2.2.1]heptane rings, which are optionally substituted with $CO_2$(1-4C alkyl), such as $CO_2C(CH_3)_3$. Particular examples of $R^2$ when represented by —$NR^bR^c$, wherein —$NR^bR^c$ forms a 7-8 membered bridged heterocyclic ring, include the structures:

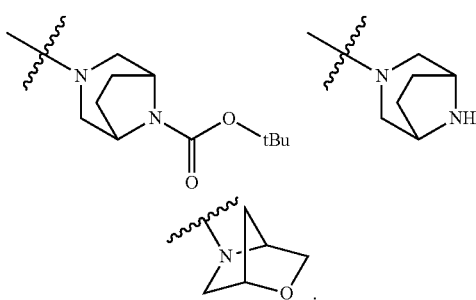

In certain embodiments, $R^2$ is selected from (1-4C)alkyl, (1-4C)fluoroalkyl, $CF_3$, -(1-4C)hydroxyalkyl, (1-4C alkyl)hetAr$^1$, and -(1-4C alkyl)NH(1-4C alkyl).

In certain embodiments, $R^2$ is (1-4C)alkyl. Particular examples include methyl, isopropyl and tert-butyl.

In certain embodiments, $R^2$ is (1-4C)fluoroalkyl. A particular example includes $CF(CH_3)_2$.

In certain embodiments, $R^2$ is $CF_3$.

In certain embodiments, $R^2$ is (1-4C)hydroxyalkyl. Particular examples include $C(CH_3)_2OH$ and $C(CH_3)_2CH_2OH$.

In certain embodiments, $R^2$ is -(1-4C alkyl)hetAr$^1$, where hetAr$^1$ is a 5-membered heteroaryl ring having 1-3 ring nitrogen atoms. An example of hetAr$^1$ is a triazolyl ring, such as 1,2,4-triazolyl. Examples of the (1-4C)alkyl portion include methylene, ethylene, dimethylmethylene, and the like. A particular value for $R^2$ when represented by -(1-4C alkyl)hetAr$^1$ is the structure:

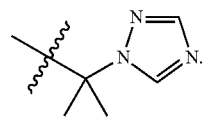 [SMILES: *C(C)(C)n1cncn1]

In certain embodiments, $R^2$ is -(1-4C alkyl)NH(1-4C alkyl). Examples include groups having the formula (1-4C alkyl)NHCH$_3$. A particular value include —$C(CH_3)_2NHCH_3$.

In certain embodiments, $R^2$ is selected from methyl, isopropyl, tert-butyl, $CF(CH_3)_2$, $CF_3$, $C(CH_3)_2OH$ and $C(CH_3)_2CH_2OH$, 2-(1,2,4-triazolyl)propan-2-yl, and —$C(CH_3)_2NHCH_3$.

In certain embodiments, $R^2$ is (3-6C cycloalkyl) which is optionally substituted with (1-4C)alkyl, CN, OH, OMe, $NH_2$, NHMe, $N(CH_3)_2$, F, $CF_3$, $CO_2$(1-4C alkyl) or $CO_2H$. In certain embodiments, $R^2$ is a cyclopropyl ring optionally substituted with (1-4C alkyl), CN, OH, $CF_3$, $CO_2$(1-4C alkyl) or $CO_2H$. Particular examples of $R^2$ include the structures:

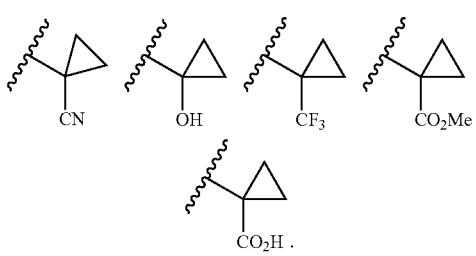

In certain embodiments $R^2$ is a (3-6C cycloalkyl) include cyclopropyl, cyclobutyl and cyclopentyl rings optionally substituted with (1-4C alkyl), CN, OH, $CF_3$, $CO_2$(1-4C alkyl) or $CO_2H$. Examples include cyclobutyl and cyclopentyl rings optionally substituted with OH. Further examples of $R^2$ include the structures:

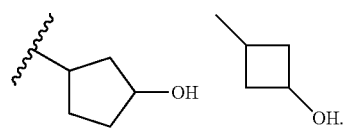

In certain embodiments, $R^2$ is selected from hetAr$^2$, hetCyc$^1$, and hetCyc$^2$.

In certain embodiments, $R^2$ is hetAr$^2$. Examples of hetAr$^2$ include pyridyl, pyrimidyl, pyrazinyl, pyrazolyl, imidazolyl and thiazolyl rings optionally substituted with one or more substituents independently selected from (1-4C alkyl), halogen, (1-4C)alkoxy and NH(1-4C alkyl). Particular examples of substituents for hetAr$^2$ include methyl, ethyl, chloro, OMe, and NHCH(CH$_3$)$_2$. In certain embodiments, hetAr$^2$ is optionally substituted with 1 or 2 of said substituents. Particular values of R$^2$ when represented by hetAr$^2$ include the structures:

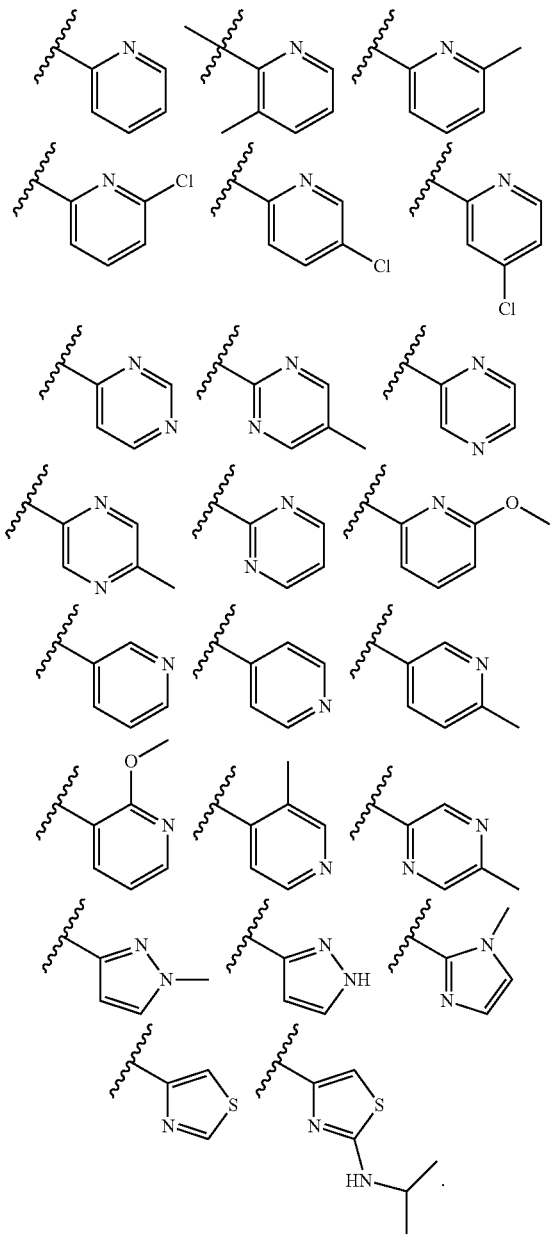

In certain embodiments, R$^2$ is hetCyc$^1$. Examples of hetCyc$^1$ include carbon-linked azetidinyl, pyrrolidinyl and piperidinyl rings optionally substituted with one or more substituents independently selected from (1-4C alkyl), CO$_2$H and CO$_2$(1-4C alkyl). Examples of substituents include methyl, ethyl, propyl, CO$_2$Me, CO$_2$Et and CO$_2$C(CH$_3$)$_3$. In one embodiment, hetCyc$^1$ is optionally substituted with one or two of said substituents. Particular values for R$^2$ represented by hetCyc$^1$ include the structures:

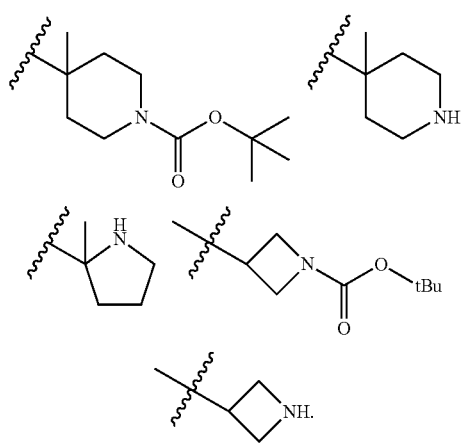

In certain embodiments, R$^2$ is hetCyc$^2$. Examples include a pyridinone or pyridazinone ring which is optionally substituted with a substituent selected from (1-4C)alkyl such as a methyl or ethyl group. Particular values of R$^2$ when represented by hetCyc$^2$ include the structures:

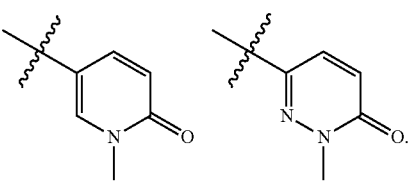

In certain embodiments, R$^2$ is selected from (i) pyridyl, pyrimidyl, pyrazinyl, pyrazolyl, imidazolyl and thiazolyl rings optionally substituted with one or more substituents independently selected from (1-4C alkyl), halogen, (1-4C) alkoxy and NH(1-4C alkyl); (ii) carbon-linked azetidinyl, pyrrolidinyl and piperidinyl rings optionally substituted with one or more substituents independently selected from (1-4C alkyl), CO$_2$H and CO$_2$(1-4C alkyl); and (iii) a pyridinone or pyridazinone ring which is optionally substituted with a substituent selected from (1-4C)alkyl.

In certain embodiments, R$^2$ is selected from the structures:

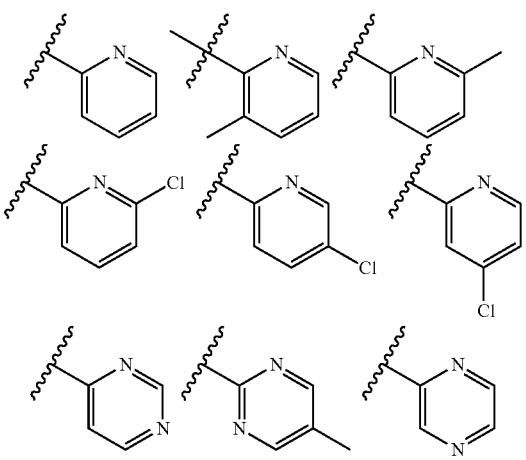

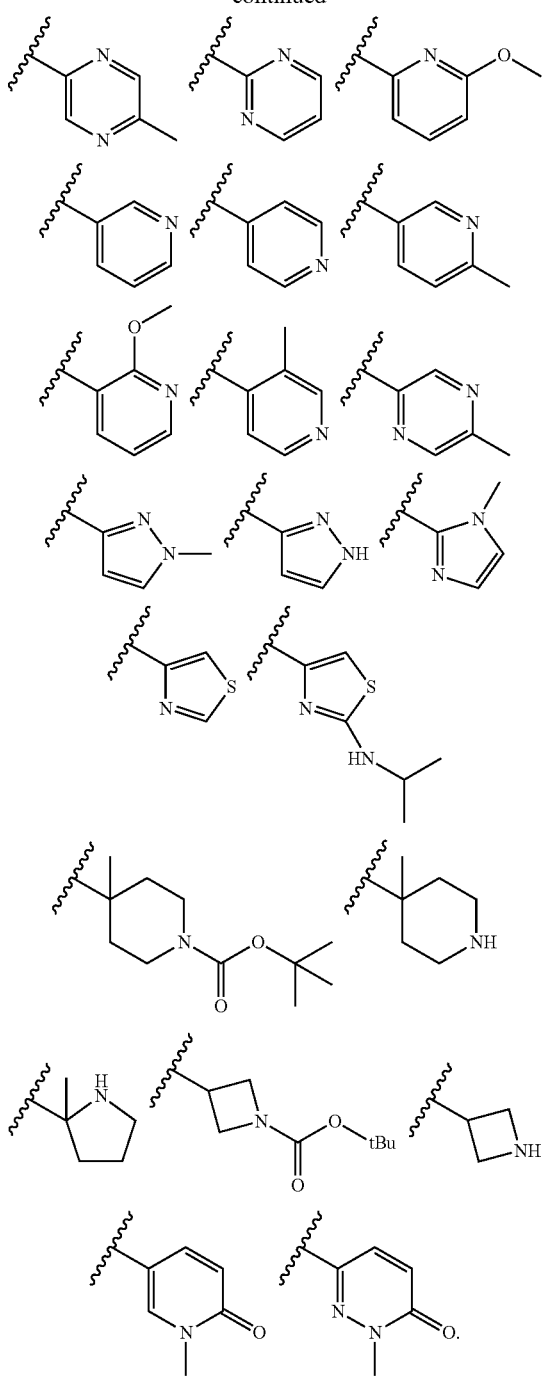

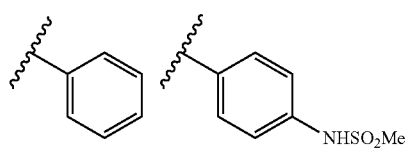

In certain embodiments, R² is phenyl which is optionally substituted with an NHSO₂(1-4C alkyl) group such a methanesulfonamido or an ethanesulfonamido group. Particular values for R² include the structures:

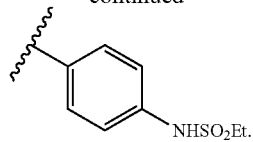

In certain embodiments, R² is C(=O)NR$^e$R$^f$ or C(=O)OR$^g$.

In certain embodiments, R² is C(=O)NR$^e$R$^f$. In certain embodiments, R$^e$ is H or (1-4C)alkyl and R$^f$ is H, (1-4C)alkyl, or (3-6C)cycloalkyl. Particular values for R² include C(=O)NH₂, C(=O)NHMe, C(=O)NMe₂ and C(=O)NH-cyclopropyl.

In certain embodiments R² is C(=O)NR$^e$R$^f$, where NR$^e$R$^f$ forms a 4-6-membered azacyclic ring optionally having an additional ring heteroatom selected from N and O, wherein the azacyclic ring is optionally substituted with OH. Particular values for R² include the structures:

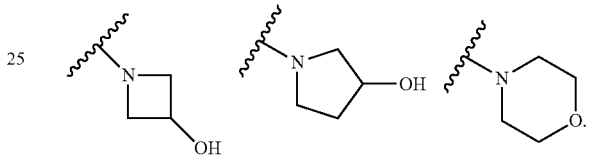

In certain embodiments where R² is C(=O)OR$^g$. Particular examples include C(=O)OH and C(=O)Me.

Referring now to the substituents on the ring at the 5-position of Formula I, in one embodiment Y is phenyl optionally substituted with one or more substituents independently selected from halogen, (1-4C)alkoxy, CF₃ and CHF₂. In one embodiment, Y is phenyl optionally substituted with one or more substituents independently selected from F, Cl, OMe, CF₃ and CHF₂. In certain embodiments, Y is phenyl optionally substituted with one or two of said substituents. Particular values for Y include phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl and 3-chloro-5-fluorophenyl.

In one embodiment, Y is a 5-6 membered heteroaryl ring having a ring heteroatom selected from N and S and optionally substituted with one or more halogen atoms. Examples include pyridyl and thienyl groups optionally substituted with one or more halogen atoms, for example one or more fluoro atoms. Particular values for Y include 2-pyridyl, 3-pyridyl, 5-fluoropyrid-3-yl and 2-thienyl.

In one embodiment, the Y group has the absolute configuration shown in FIG. Ia:

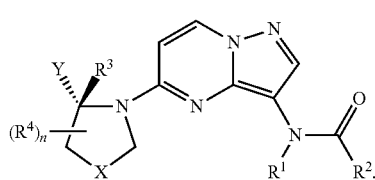

With reference to the R³ substituent, in one embodiment R³ is H. In one embodiment, R³ is (1-4C)alkyl, for example, methyl, ethyl, propyl, isopropyl or butyl. Particular values for R³ include hydrogen and methyl.

With reference to the R⁴ substituent, in one embodiment R⁴ is halogen. Particular examples are fluoro and chloro.

In one embodiment, R⁴ is (1-4C)alkyl, such as methyl, ethyl, propyl, isopropyl, or butyl. A particular example is methyl.

In one embodiment, R⁴ is OH.

In one embodiment, R⁴ is (1-4C)alkoxy, for example OMe and OEt.

In one embodiment, R⁴ is NH₂.

In one embodiment, R⁴ is NH(1-4C alkyl), for example NHMe, NHEt, NHPr, NHiPr or NHBu. A particular example is NHMe.

In one embodiment, R⁴ is CH₂OH.

In one embodiment, each R⁴ is independently selected from F, Cl, OH, OMe, NH₂, Me, CH₂OH and NHMe.

In one embodiment, n is 0, 1, 2, 3 or 4. In one embodiment, n is 0, 1, 2 or 3. In one embodiment, n is 0, 1 or 2.

With continued reference to the ring at the 5-position of Formula I, in certain embodiments, X is null, —CH₂— or —CH₂CH₂—.

In one embodiment X is null, such that the heterocyclic ring at the 5-position of Formula I has the structure:

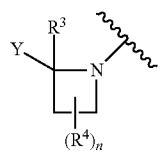

where R³, R⁴, Y and n are as defined herein. In one embodiment, Y is phenyl optionally substituted with one or more substituents independently selected from halogen, (1-4C) alkoxy, CF₃ and CHF₂. In one embodiment, Y is 5-6 membered heteroaryl ring having a ring heteroatom selected from N and S, wherein said heteroaryl ring is optionally substituted with one or more halogen atoms. In one embodiment, R³ is hydrogen. In another embodiment, R³ is methyl. A particular example of the ring at the 5-position of Formula I when X is null includes the structures:

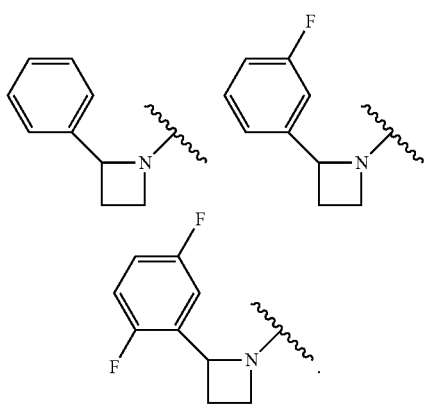

In one embodiment, X is CH₂, such that the heterocyclic ring at the 5-position of Formula I has the structure:

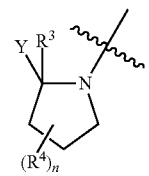

where R³, R⁴, Y and n are as defined herein. In one embodiment Y is phenyl optionally substituted with one or more substituents independently selected from halogen, (1-4C) alkoxy, CF₃ and CHF₂. In one embodiment, Y is a 5-6 membered heteroaryl ring having a ring heteroatom selected from N and S, wherein said heteroaryl ring is optionally substituted with one or more halogen atoms. In one embodiment, R³ is hydrogen. In another embodiment, R³ is methyl. In one embodiment, each R⁴ is independently selected from F, Cl, Me, OH, OMe, NH₂, NHMe, CH₂OH, CHF₂ and CF₃. In one embodiment, n is 0, 1 or 2. Particular examples of the ring at the 5-position of Formula I when X is CH₂ include the structures:

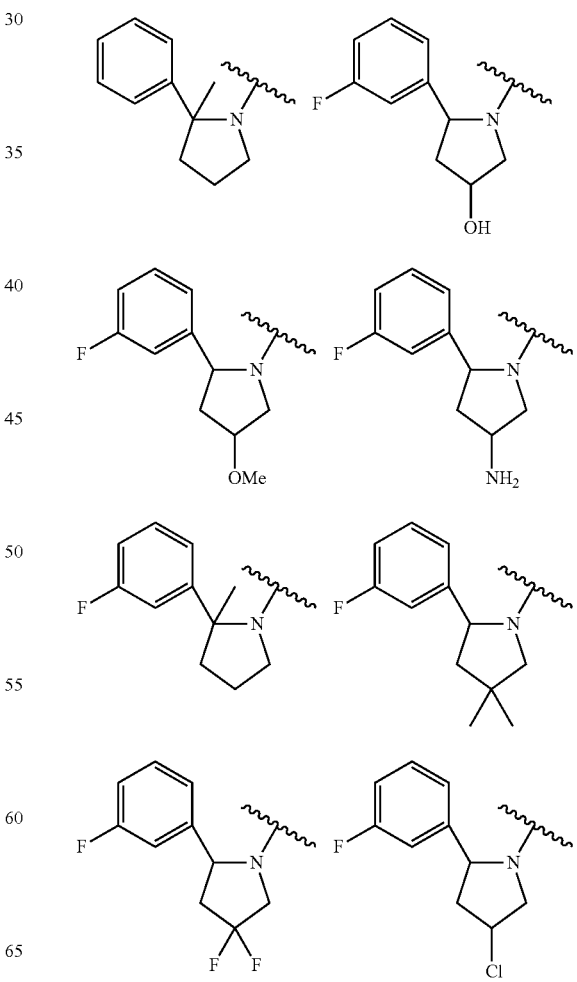

-continued

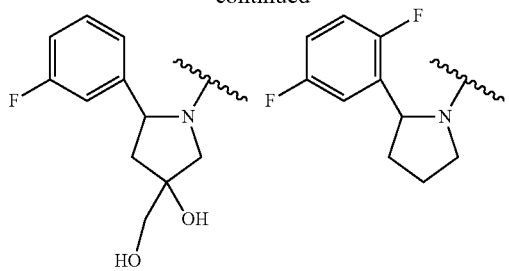

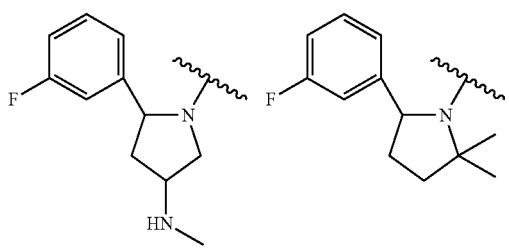

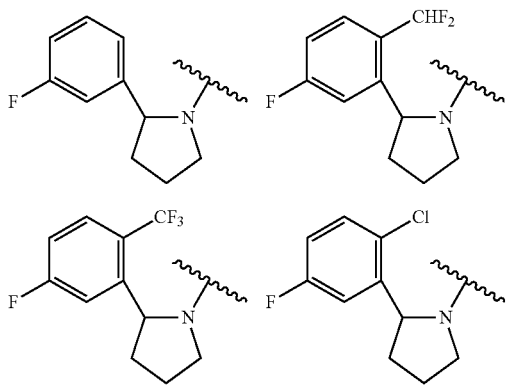

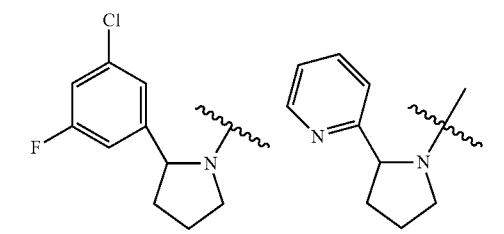

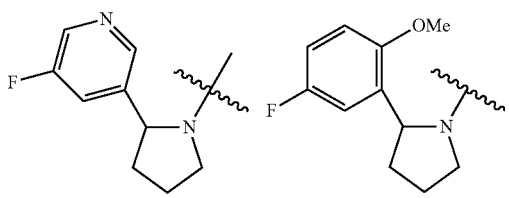

In one embodiment, X is CH₂CH₂, such that the heterocyclic ring at the 5-position of Formula I has the structure:

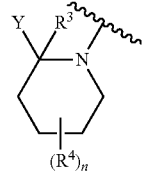

where $R^3$, $R^4$, Y and n are as defined herein. In one embodiment, phenyl optionally substituted with one or more substituents independently selected from halogen, (1-4C)alkoxy, $CF_3$ and $CHF_2$. In one embodiment, Y is a 5-6 membered heteroaryl ring having a ring heteroatom selected from N and S, wherein said heteroaryl ring is optionally substituted with one or more halogen atoms. In one embodiment, $R^3$ is hydrogen. In another embodiment, $R^3$ is methyl. In one embodiment, n is 0, 1 or 2. In one embodiment, n is 0. Particular examples of the ring at the 5-position of Formula I when X is $CH_2CH_2$ include the structures:

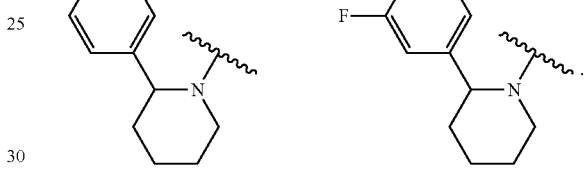

In one embodiment, X is —CH₂O—. In one embodiment, the heterocyclic ring at the 5-position of Formula I has the structure:

where $R^3$, $R^4$, Y and n are as defined herein. In one embodiment, Y is phenyl optionally substituted with one or more substituents independently selected from halogen, (1-4C)alkoxy, $CF_3$ and $CHF_2$. In one embodiment, Y is phenyl optionally substituted with one or more substituents independently selected from F and (1-4C)alkoxy. In one embodiment, Y is a 5-6 membered heteroaryl ring having a ring heteroatom selected from N and S, wherein said heteroaryl ring is optionally substituted with one or more halogen atoms. In one embodiment, $R^3$ is hydrogen. In another embodiment, $R^3$ is methyl. In one embodiment, n is 0, 1 or 2. Particular examples of the ring at the 5-position of Formula I when X is —CH₂O— include the structures:

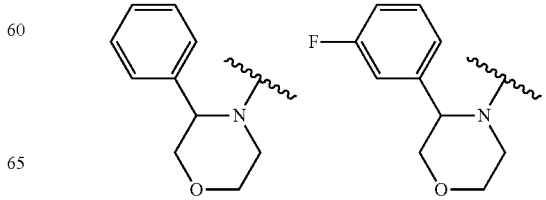

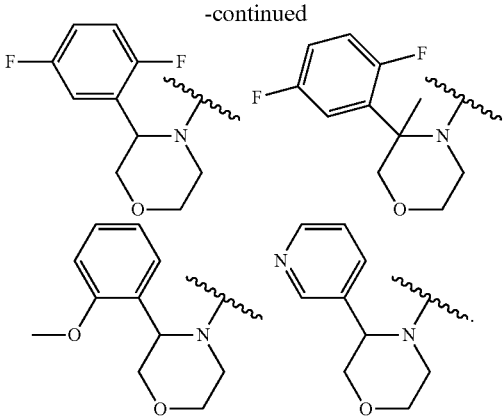

In one embodiment, X is —CH$_2$NR$^d$—. In one embodiment, the heterocyclic ring at the 5-position of Formula I has the structure:

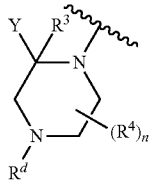

where R$^3$, R$^4$, Y, R$^d$ and n are as defined herein. In one embodiment, R$^d$ is H. In one embodiment, R$^d$ is (1-4C alkyl), for example methyl, ethyl, propyl, isopropyl, or butyl. A particular example is methyl. In one embodiment, Y is phenyl optionally substituted with one or more substituents independently selected from halogen, (1-4C)alkoxy, CF$_3$ and CHF$_2$. In one embodiment, Y is a 5-6 membered heteroaryl ring having a ring heteroatom selected from N and S, wherein said heteroaryl ring is optionally substituted with one or more halogen atoms. In one embodiment, n is 0. Particular examples of the ring at the 5-position of Formula I when X is —CH$_2$NR$^d$— include the structures:

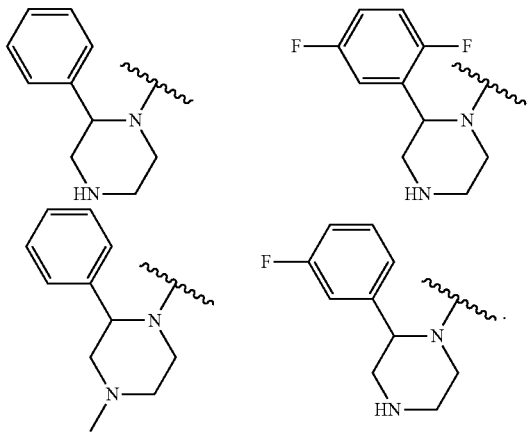

Compounds of Formula I include compound of Formula Ib, wherein
R$^1$ is H or (1-6C alkyl);
R$^2$ is NR$^b$R$^c$;

NR$^b$R$^c$ forms a 4 membered heterocyclic ring having a ring nitrogen atom, wherein said heterocyclic ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl, or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo;

Y is phenyl optionally substituted with one or more substituents independently selected from halogen, (1-4C)alkoxy, CF$_3$ and CHF$_2$;
X is null, —CH$_2$—, or —CH$_2$CH$_2$—;
R$^3$ is H or (1-4C alkyl);
each R$^4$ is independently selected from halogen, (1-4C) alkyl, OH, (1-4C)alkoxy, NH$_2$, NH(1-4C alkyl) and CH$_2$OH; and
n is 0, 1, or 2.

In one embodiment of Formula Ib, Y is phenyl optionally substituted with one or more halogen atoms. In one embodiment of Formula Ib, Y is phenyl optionally substituted with one or two fluorine atoms.

In one embodiment of Formula Ib, NR$^b$R$^c$ forms a 4 membered heterocyclic ring having a ring nitrogen atom, wherein said ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl, or (ii) NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo.

In one embodiment of Formula Ib, NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo.

In one embodiment of Formula Ib, n is zero or one.
In one embodiment of Formula Ib, R$^3$ is hydrogen.
Compounds of Formula Ib include compounds of Formula Ic wherein:
R$^1$ is H or (1-6C alkyl);
R$^2$ is NR$^b$R$^c$;
NR$^b$R$^c$ forms a 4 membered heterocyclic ring having a ring nitrogen atom, wherein said heterocyclic ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl;
Y is phenyl optionally substituted with one or more substituents independently selected from halogen, (1-4C)alkoxy, CF$_3$ and CHF$_2$;
X is —CH$_2$—;
R$^3$ is H or (1-4C alkyl);
each R$^4$ is independently selected from halogen, (1-4C) alkyl, OH, (1-4C)alkoxy, NH$_2$, NH(1-4C alkyl) and CH$_2$OH; and
n is 0, 1, or 2.

In one embodiment of Formula Ic, the heterocyclic ring formed by $NR^bR^c$ is optionally substituted with one or two substituents independently selected from F, OH, methyl, OMe, OC(=O)C(CH$_3$)$_2$, NH$_2$, —NHC(=O)OC(CH$_3$)$_3$ and CH$_2$OH.

In one embodiment of Formula Ic, the heterocyclic ring formed by $NR^bR^c$ is 4 membered azacyclic ring optionally substituted with one or two substituents independently selected from OH, (1-4C alkyl), and —O(1-4C alkyl), for example OH, Me and OMe.

In one embodiment of Formula Ic, Y is phenyl optionally substituted with one or more halogen atoms. In one embodiment of Formula Ic, Y is phenyl optionally substituted with one or two fluorine atoms.

Compounds of Formula Ib also include compounds of Formula Id wherein:

$R^1$ is H or (1-6C alkyl);

$R^2$ is $NR^bR^c$;

$NR^bR^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo;

Y is phenyl optionally substituted with one or more substituents independently selected from halogen, (1-4C)alkoxy, CF$_3$ and CHF$_2$;

X is —CH$_2$—;

$R^3$ is H or (1-4C alkyl);

each $R^4$ is independently selected from halogen, (1-4C) alkyl, OH, (1-4C)alkoxy, NH$_2$, NH(1-4C alkyl) and CH$_2$OH; and n is 0, 1, or 2.

In one embodiment of Formula Id, the heterocyclic ring formed by $NR^bR^c$ is optionally substituted with one or two substituents independently selected from OH, F, NH$_2$, CO$_2$H, CO$_2$Et, NHCO$_2$C(CH$_3$)$_3$, CF$_3$, methyl, ethyl, isopropyl, CO$_2$C(CH$_2$)$_3$ and oxo.

In one embodiment of Formula Id, the heterocyclic ring formed by $NR^bR^c$ is a 5-6 membered azacyclic ring optionally substituted with one or more substituents independently selected from OH, F, NH$_2$, CO$_2$H, CO$_2$Et, NHCO$_2$C(CH$_3$)$_3$, CF$_3$, methyl, ethyl, isopropyl, CO$_2$C(CH$_2$)$_3$ and oxo.

In one embodiment of Formula Id, the heterocyclic ring formed by $NR^bR^c$ is a 5 membered azacyclic ring optionally substituted with one or more substituents independently selected from OH, F, NH$_2$, CO$_2$H, CO$_2$Et, NHCO$_2$C(CH$_3$)$_3$, CF$_3$, methyl, ethyl, isopropyl, CO$_2$C(CH$_2$)$_3$ and oxo.

In certain embodiments of Formula Id, —$NR^bR^c$ forms a 5-membered azacyclic ring optionally substituted with one to two substituted independently selected from OH and Me.

In one embodiment of Formula Id, the heterocyclic ring formed by $NR^bR^c$ is a 6 membered azacyclic ring optionally substituted with one or more substituents independently selected from OH, F, NH$_2$, CO$_2$H, CO$_2$Et, NHCO$_2$C(CH$_3$)$_3$, CF$_3$, methyl, ethyl, isopropyl, CO$_2$C(CH$_2$)$_3$ and oxo.

In one embodiment of Formula Id, the heterocyclic ring formed by $NR^bR^c$ is a 6 membered azacyclic ring optionally substituted with one or two substituents independently selected from OH and (1-4C)alkyl, for example OH and Me.

In one embodiment of Formula Id, Y is phenyl optionally substituted with one or more halogen atoms. In one embodiment of Formula Id, Y is phenyl optionally substituted with one or two fluorine atoms.

In one embodiment of Formula Ic or Id, n is zero or one.

In one embodiment of Formula Ic or Id, $R^3$ is hydrogen.

In one embodiment of Formula Ic or Id, $R^1$ is hydrogen.

Compounds of Formula I include compound of Formula Ie, wherein:

$R^1$ is H or (1-6C alkyl);

$R^2$ is $NR^bR^c$;

$NR^bR^c$ forms a 4 membered heterocyclic ring having a ring nitrogen atom, wherein said heterocyclic ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl, or $NR^bR^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo;

Y is a 5-6 membered heteroaryl ring having a ring heteroatom selected from N and S, wherein said heteroaryl ring is optionally substituted with one or more halogen atoms;

X is null, —CH$_2$—, or —CH$_2$CH$_2$—;

$R^3$ is H or (1-4C alkyl);

each $R^4$ is independently selected from halogen, (1-4C) alkyl, OH, (1-4C)alkoxy, NH$_2$, NH(1-4C alkyl) and CH$_2$OH; and n is 0, 1, or 2.

Compounds of Formula I include compounds of Formula If, wherein:

$R^1$ is H or (1-6C alkyl);

$R^2$ is (1-4C)alkyl, (1-4C)fluoro alkyl, CF$_3$, (1-4C)hydroxyalkyl, -(1-4C alkyl)hetAr$^1$, -(1-4C alkyl)NH$_2$, -(1-4C alkyl)NH(1-4C alkyl), -(1-4C alkyl)N(1-4C alkyl)$_2$, hetAr$^2$, hetCyc$^1$, hetCyc$^2$, phenyl which is optionally substituted with NHSO$_2$(1-4C alkyl), or (3-6C)cycloalkyl which is optionally substituted with (1-4C alkyl), CN, OH, OMe, NH$_2$, NHMe, N(CH$_3$)$_2$, F, CF$_3$, CO$_2$(1-4C alkyl), CO$_2$H, C(=O)NR$^e$R$^f$ or C(=O)OR$^g$;

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4C)alkoxy, and NH(1-4C alkyl);

hetCyc$^1$ is a carbon-linked 4-6 membered azacyclic ring optionally substituted with one or more substituents independently selected from (1-4C alkyl), and CO$_2$(1-4C alkyl);

hetCyc$^2$ is a pyridinone or pyridazinone ring which is optionally substituted with a substituent selected from (1-4C) alkyl;

$R^e$ is H or (1-4C)alkyl;

$R^f$ is H, (1-4C)alkyl, or (3-6C)cycloalkyl;

or NR$^e$R$^f$ forms a 5-6-membered azacyclic ring optionally having an additional ring heteroatom selected from N and O, wherein the azacyclic ring is optionally substituted with OH;

$R^g$ is H or (1-6C)alkyl;

Y is (i) phenyl optionally substituted with one or more substituents independently selected from halogen, (1-4C) alkoxy, CF$_3$ and CHF$_2$, or (ii) a 5-6 membered heteroaryl ring having a ring heteroatom selected from N and S, wherein said heteroaryl ring is optionally substituted with one or more halogen atoms;

X is null, —CH$_2$—, —CH$_2$CH$_2$—;

$R^d$ is H or (1-4C alkyl);

R³ is H or (1-4C alkyl);

each R⁴ is independently selected from halogen, (1-4C) alkyl, OH, (1-4C)alkoxy, NH₂, NH(1-4C alkyl) and CH₂OH; and n is 0, 1, 2, 3, 4, 5 or 6.

In one embodiment of Formula If, Y is phenyl optionally substituted with one or more substituents independently selected from halogen, (1-4C)alkoxy, CF₃ and CHF₂.

In one embodiment of Formula If, Y is a 5-6 membered heteroaryl ring having a ring heteroatom selected from N and S, wherein said heteroaryl ring is optionally substituted with one or more halogen atoms.

In one embodiment of Formula If, R² is selected from (1-4C)alkyl, (1-4C)fluoroalkyl, CF₃, -(1-4C)hydroxyalkyl, (1-4C alkyl)hetAr¹, and -(1-4C alkyl)NH(1-4C alkyl)

In one embodiment of Formula If, R² is selected from methyl, isopropyl, tert-butyl, CF(CH₃)₂, CF₃, C(CH₃)₂OH and C(CH₃)₂CH₂OH, 2-(1,2,4-triazolyl)propan-2-yl, and —C(CH₃)₂NHCH₃.

In one embodiment of Formula If, R² is a cyclopropyl, cyclobutyl and cyclopentyl ring optionally substituted with (1-4C alkyl), CN, OH, CF₃, CO₂(1-4C alkyl) or CO₂H.

In one embodiment of Formula If, R² is selected from hetAr², hetCyc¹, and hetCyc².

In one embodiment of Formula If, R² is selected from (i) pyridyl, pyrimidyl, pyrazinyl, pyrazolyl, imidazolyl and thiazolyl rings optionally substituted with one or more substituents independently selected from (1-4C alkyl), halogen, (1-4C)alkoxy and NH(1-4C alkyl); (ii) carbon-linked azetidinyl, pyrrolidinyl and piperidinyl rings optionally substituted with one or more substituents independently selected from (1-4C alkyl), CO₂H and CO₂(1-4C alkyl); and (iii) a pyridinone or pyridazinone ring which is optionally substituted with a substituent selected from (1-4C)alkyl.

In one embodiment of Formula If, R² is C(=O)NRᵉRᶠ or C(=O)ORᵍ.

Compounds of Formula I include compound of Formula Ig, wherein

R¹ is H or (1-6C alkyl);

R² is NRᵇRᶜ;

Rᵇ is H or (1-6C alkyl);

Rᶜ is H, (1-4C)alkyl, (1-4C)hydroxyalkyl, hetAr³, or phenyl, wherein said phenyl is optionally substituted with one or more substituents independently selected from halogen, CN, CF₃ and —O(1-4C alkyl);

hetAr³ is a 5-6 membered heteroaryl ring having 1-2 ring heteroatoms independently selected from N and O and optionally substituted with one or more substituents independently selected from (1-4C)alkyl;

Y is (i) phenyl optionally substituted with one or more substituents independently selected from halogen, (1-4C)alkoxy, CF₃ and CHF₂, or (ii) a 5-6 membered heteroaryl ring having a ring heteroatom selected from N and S, wherein said heteroaryl ring is optionally substituted with one or more halogen atoms;

X is null, —CH₂—, or —CH₂CH₂—;

Rᵈ is H or (1-4C alkyl);

R³ is H or (1-4C alkyl);

each R⁴ is independently selected from halogen, (1-4C) alkyl, OH, (1-4C)alkoxy, NH₂, NH(1-4C alkyl) and CH₂OH; and n is 0, 1, 2, 3, 4, 5 or 6.

In one embodiment of Formula Ig, Y is phenyl optionally substituted with one or more substituents independently selected from halogen, (1-4C)alkoxy, CF₃ and CHF₂.

In one embodiment of Formula Ig, Y is a 5-6 membered heteroaryl ring having a ring heteroatom selected from N and S, wherein said heteroaryl ring is optionally substituted with one or more halogen atoms.

In one embodiment of Formula Ig, Rᶜ is selected from H, Me, t-butyl, CH₂CH₂OH and CH₂CH₂CH₂OH, dimethylisoxazolyl, phenyl, fluorophenyl, chlorophenyl, cyanophenyl, methoxyphenyl, trifluoromethylphenyl, dichlorophenyl, and trimethoxyphenyl. More particular examples include 4-fluorophenyl, 3-chlorophenyl, 4-chlorophenyl, 3-cyanophenyl, 4-cyanophenyl, 4-methoxyphenyl, 2-4-dichlorophenyl, 3-(trifluoromethyl)phenyl, 3,5-dichlorophenyl, and 3,4,5-trimethoxyphenyl.

In one embodiment of Formula Ig, n is 0, 1 or 2.

It will be appreciated that certain compounds according to the invention may contain one or more centers of asymmetry and may therefore be prepared and isolated in a mixture of isomers such as a racemic or diastereomeric mixture, or in an enantiomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for further compounds of Formula I.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Examples of particular salts include hydrogen sulfate salts, hydrochloride salts and trifluoroacetate salts.

It will further be appreciated that the compounds of Formula I and their salts may be isolated in the form of solvates, and accordingly that any such solvate is included within the scope of the present invention.

The compounds of Formula I also include compounds that differ only in the presence of one or more isotopically enriched atoms. For example, compounds of the invention include compounds wherein one or more hydrogen atoms are replaced deuterium or tritium, or one or more carbon atoms are replaced by a ¹³C- or ¹⁴C-enriched carbon are within the scope of this invention.

The term "(1-4C) alkyl" as used herein refers to saturated linear or branched-chain monovalent hydrocarbon radicals of one to four carbon atoms, respectively. Examples include, but are not limited to, methyl, ethyl, 1-propyl, 2-propyl, 1-butyl, 2-methyl-1-propyl, 2-butyl, and 2-methyl-2-propyl.

The term "(1-4C) alkoxy" as used herein refers to saturated linear or branched-chain monovalent radicals of one to four carbon atoms, respectively, wherein the radical is on the oxygen atom.

The term "(1-4C)hydroxyalkyl" as used herein refers to saturated linear or branched-chain monovalent hydrocarbon radicals of one to four carbon atoms, respectively, wherein one of the hydrogen atoms is replaced with an OH group.

The term "halogen" includes fluoro, chloro, bromo and iodo.

According to another aspect, the present invention provides a process for the preparation of a compound of Formula I or a pharmaceutically acceptable salt thereof as defined herein which comprises:

(a) for a compound of Formula I wherein $R^2$ is $NR^bR^c$, reacting a corresponding compound of formula II

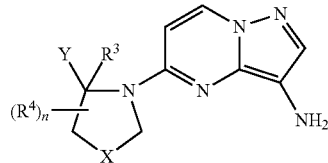

II with a compound having the formula $HNR^bR^c$ in the presence of a coupling reagent; or (b) for a compound of Formula I wherein $R^2$ is $NR^bR^c$ and Rb is H, reacting a corresponding compound of formula II with a compound having the formula O=C=N—$R^c$; or (c) for a compound of Formula I wherein $R^2$ is $hetAr^2$ or a phenyl ring which is optionally substituted with $NHSO_2$(1-4C alkyl), reacting a corresponding compound of Formula II with a corresponding compound having the formula HOC(=O)$R^2$ in the presence of a coupling reagent and a base; or (d) for a compound of Formula I wherein $R^2$ is (1-4C)alkyl, (1-4C)fluoroalkyl, $CF_3$, (1-4C)hydroxyalkyl, or (3-6C)cycloalkyl which is optionally substituted with (1-4C alkyl), CN, OH, $CF_3$, $CO_2$(1-4C alkyl) or $CO_2H$, reacting a corresponding compound of Formula II with a corresponding compound having the formula $(R^2CO)_2O$ in the presence of a base; or (e) for a compound of Formula I wherein $R^2$ is (1-4C)alkyl, (1-4C)fluoroalkyl, $CF_3$, (1-4C)hydroxyalkyl, or (3-6C)cycloalkyl which is optionally substituted with (1-4C alkyl), CN, OH, $CF_3$, $CO_2$(1-4C alkyl) or $CO_2H$, reacting a corresponding compound of Formula II with a corresponding compound having the formula HOC(=O)$R^2$ in the presence of a coupling reagent and a base; or (f) for a compound of Formula I wherein $R^2$ is C(=O)$NR^eR^f$, reacting a compound of formula VII

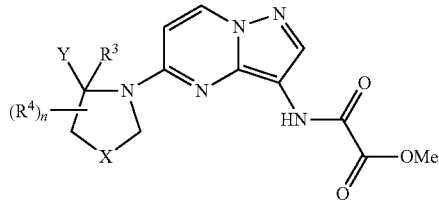

VII with a compound having the formula $HNR^eR^f$ in the presence of a base; or (g) for a compound of Formula I wherein $R^2$ is C(=O)$OR^g$, reacting a compound of Formula II with methyl 2-chloro-2-oxoacetate, and treating with an alkali hydroxide to prepare a compound of formula I where $R^g$ is H; and removing or adding any protecting groups if desired, and forming a salt if desired.

Referring to methods (a) and (e), examples of suitable coupling reagents include CDI (carbonyl diimidazole), phosgene, and bis(trichloromethyl)carbonate. The reaction is optionally performed in the presence of a tertiary amine base, such as DIEA (diisopropylethylamine). Suitable solvents include dichloromethane, dichloroethane, THF, and DMF. The reaction is conveniently performed at ambient temperature.

Compounds of formula II

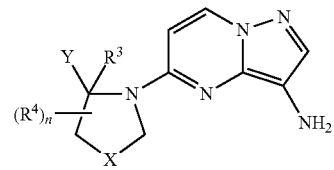

II can be prepared by reducing a corresponding compound of formula III

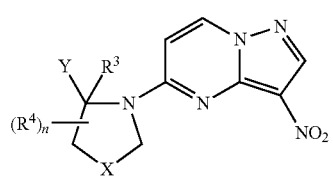

III under standard reducing conditions, for example reacting a compound of formula II with zinc dust under acidic conditions, such as in the presence of $NH_4Cl$ (saturated aqueous), HCl, or acetic acid. Another example of such standard reducing conditions includes reacting compounds of formula III under a hydrogen atmosphere in the presence of a precious metal catalyst to corresponding compounds of formula II.

Compounds of Formula III can be prepared by nitrating a corresponding compound having the formula IV

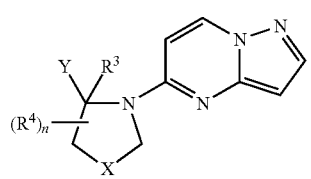

IV using standard nitrating conditions known in the art, for example by reacting a corresponding compound of Formula IV with nitric acid in the presence of an activating agent such as TFA or concentrated sulfuric acid.

Compounds of the formula IV can be prepared by coupling a corresponding compound of Formula V

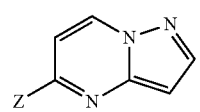

V where Z is a leaving group or atom, such as a halogen (for example Cl), with a corresponding compound having the formula VI

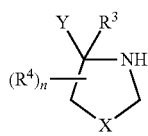

where $R^3$, $R^4$, n, X and Y are as defined herein, in a suitable solvent such as an alcohol (for example n-butanol or isopropanol), at elevated temperatures, for example at temperatures between 100 and 180° C., for example at a temperature of about 140° C. Compounds of Formula V are commercially available or can be prepared by standard methods known in the art.

Compounds of Formula II and III are also believed to be novel and provide a further embodiment of this invention.

Referring to method (b), suitable solvents include dichloromethane, dichloroethane, THF, and DMF. The reaction is conveniently performed at ambient temperature.

Referring to method (c), suitable coupling reagents include HATU, HBTU, TBTU, DCC (N,N'-dicyclohexylcarbodiimide), DIEC (1-(3-dimethylaminopropyl)-3-ethylcarboiimide) and any other amide coupling reagents well known to persons skilled in the art. Suitable bases include tertiary amine bases such as diisopropylethylamine (DIEA) and triethylamine. Suitable solvents include DMF and $CH_3CN$. The reaction is conveniently performed at temperatures between 0° C. and ambient temperature.

Referring to method (d), suitable bases include amine bases such as pyridine or triethylamine, and suitable coupling reagents include HATU, HBTU, TBTU, DCC(N,N'-dicyclohexylcarbodiimide), DIEC (1-(3-dimethylaminopropyl)-3-ethylcarboiimide) and any other amide coupling reagents well known to persons skilled in the art. Suitable solvents include dichloromethane and dichloroethane. The reaction is conveniently performed at temperatures between 0° C. and ambient temperature.

The ability of compounds to act as TrkA inhibitors may be demonstrated by the assays described in Examples A and B. The ability of compounds to act as TrkB inhibitors may be demonstrated by the assay described in Example B.

Compounds of Formula I are useful for treating chronic and acute pain, including pain associated with cancer, surgery, and bone fracture. Certain compounds which are inhibitors of TrkA and/or TrkB may be useful in the treatment of multiple types of pain including inflammatory pain, neuropathic pain, and pain associated with cancer, surgery, and bone fracture.

Compounds of Formula I are also useful for treating cancers including neuroblastoma, ovarian, pancreatic and colorectal cancer.

Compounds of Formula I are also useful for treating inflammation and certain infectious diseases.

In addition, compounds of Formula I may also be used to treat interstitial cystitis (IC), painful bladder syndrome (PBS), urinary incontinence, asthma, anorexia, atopic dermatitis, and psoriasis.

Compounds of Formula I may also be used to treat demyelination and dysmyelination by promoting myelination, neuronal survival, and oligodendrocyte differentiation via blocking Sp35-TrkA interaction.

Compounds of Formula I which are dual inhibitors of TrkA and TrkB may be useful in the treatment of multiple types of pain including inflammatory pain, neuropathic pain, surgical pain and pain associated with cancer.

Compounds of Formula I may be of therapeutic value for the useful in the treatment of bone-related diseases (such as those involving bone resorption). Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments.

Other osteolytic diseases that can be treated according to the present invention are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present invention contemplates treating.

As used herein, the term treatment includes prophylaxis as well as treatment of an existing condition.

Accordingly, another aspect of this invention provides a method of treating diseases or medical conditions in a mammal, wherein said disease or condition is treatable with an inhibitor of TrkA and/or TrkB, comprising administering to said mammal one or more compounds of Formula I or a pharmaceutically acceptable salt thereof in an amount effective to treat or prevent said disorder. In a particular embodiment, the invention provides a method of treating pain, cancer, inflammation, neurodegenerative disease or *Typanosoma cruzi* infection in a mammal, which comprises administering to said mammal a therapeutically effective amount of a compound of Formula I, or a pharmaceutically acceptable salt thereof.

In another embodiment, the invention provides a method of treating osteolytic disease in a mammal, which comprises administering to said mammal a therapeutically effective amount of a compound of Formula I or a pharmaceutically acceptable salt thereof.

The compounds of the present invention can be used in combination with one or more additional drugs that work by the same or a different mechanism of action. Such conjoint treatment may be achieved by way of the simultaneous, sequential or separate administration of the individual components of the treatment. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonal antibodies.

Accordingly, the compounds of Formula I may be administered in combination with one or more agents selected from mitotic inhibitors, alkylating agents, anti-metabolites, anti-sense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

The phrase "effective amount" means an amount of compound that, when administered to a mammal in need of such treatment, is sufficient to (i) treat or prevent a particular disease, condition, or disorder which can be treated with an inhibitor of TrkA and/or TrkB, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a condition treatable with an inhibitor or TrkA and/or TrkB, such as a TrkA and/or TrkB mediated condition, such as one or more conditions described herein.

According to a further aspect, the present invention provides the use of a compound of Formula I or a pharmaceutically acceptable salt thereof, in the treatment of a condition that can be treated with an inhibitor of TrkA and/or TrkB, such as a TrkA and/or TrkB mediated condition, such as a condition as defined hereinabove. In one embodiment, the invention provides a compound of Formula I, or a pharmaceutically acceptable salt thereof, for use in the treatment of pain, cancer, inflammation, neurodegenerative disease or *Typanosoma cruzi* infection.

In one embodiment, a compound of the invention is selected from any one of:

(R)—N-(5-(2-(2,5-difluorophenyl)pyrrolidin-1-yl)pyrazolo[1,5-a]pyrimidin-3-yl)-3-hydroxyazetidine-1-carboxamide;

(R)-3-(5-(2-(2,5-difluorophenyl)pyrrolidin-1-yl)pyrazolo[1,5-a]pyrimidin-3-yl)-1,1-dimethylurea;

(R)-1-tert-butyl-3-(5-(2-(2,5-difluorophenyl)pyrrolidin-1-yl)pyrazolo[1,5-a]pyrimidin-3-yl)urea;

(R)-1-(5-(2-(2,5-difluorophenyl)pyrrolidin-1-yl)pyrazolo[1,5-a]pyrimidin-3-yl)-3-phenylurea;

(R)—N-(5-(2-(2,5-difluorophenyl)pyrrolidin-1-yl)pyrazolo[1,5-a]pyrimidin-3-yl)isobutyramide;

(R)—N-(5-(2-(3-fluorophenyl)pyrrolidin-1-yl)pyrazolo[1,5-a]pyrimidin-3-yl)-1-methyl-6-oxo-1,6-dihydropyridazine-3-carboxamide;

(R)—N-(5-(4,4-difluoro-2-(3-fluorophenyl)pyrrolidin-1-yl)pyrazolo[1,5-a]pyrimidin-3-yl)-3-hydroxyazetidine-1-carboxamide;

(R)—N-(5-(2-(2-chloro-5-fluorophenyl)pyrrolidin-1-yl)pyrazolo[1,5-a]pyrimidin-3-yl)-3-hydroxyazetidine-1-carboxamide;

(R)—N-(5-(2-(3-fluorophenyl)pyrrolidin-1-yl)pyrazolo[1,5-a]pyrimidin-3-yl)morpholine-4-carboxamide;

N-(5-(2-(3-fluorophenyl)-2-methylpyrrolidin-1-yl)pyrazolo[1,5-a]pyrimidin-3-yl)-3-hydroxyazetidine-1-carboxamide;

(R)—N-(5-(2-(3-chloro-5-fluorophenyl)pyrrolidin-1-yl)pyrazolo[1,5-a]pyrimidin-3-yl)-3-hydroxyazetidine-1-carboxamide;

(R)—N-(5-(2-(2-(difluoromethyl)-5-fluorophenyl)pyrrolidin-1-yl)pyrazolo[1,5-a]pyrimidin-3-yl)-3-hydroxyazetidine-1-carboxamide;

(R)—N-(5-(2-(2,5-difluorophenyl)pyrrolidin-1-yl)pyrazolo[1,5-a]pyrimidin-3-yl)morpholine-4-carboxamide;

(S)—N-(5-((R)-2-(2,5-difluorophenyl)pyrrolidin-1-yl)pyrazolo[1,5-a]pyrimidin-3-yl)-3-hydroxypyrrolidine-1-carboxamide;

(3R,4R)—N-(5-((R)-2-(2,5-difluorophenyl)pyrrolidin-1-yl)pyrazolo[1,5-a]pyrimidin-3-yl)-3,4-dihydroxypyrrolidine-1-carboxamide;

(R)—N-(5-(2-(2,5-difluorophenyl)pyrrolidin-1-yl)pyrazolo[1,5-a]pyrimidin-3-yl)-3-methoxyazetidine-1-carboxamide;

(R)—N-(5-(2-(2,5-difluorophenyl)pyrrolidin-1-yl)pyrazolo[1,5-a]pyrimidin-3-yl)-3-hydroxy-3-methylazetidine-1-carboxamide;

(R)-1-(5-(2-(2,5-difluorophenyl)pyrrolidin-1-yl)pyrazolo[1,5-a]pyrimidin-3-yl)-3-(4-fluorophenyl)urea;

(R)-1-(4-chlorophenyl)-3-(5-(2-(2,5-difluorophenyl)pyrrolidin-1-yl)pyrazolo[1,5-a]pyrimidin-3-yl)urea;

(R)-1-(5-(2-(2,5-difluorophenyl)pyrrolidin-1-yl)pyrazolo[1,5-a]pyrimidin-3-yl)-3-(4-methoxyphenyl)urea;

(R)—N-(5-(2-(2-chloro-5-fluorophenyl)pyrrolidin-1-yl)pyrazolo[1,5-a]pyrimidin-3-yl)-3-methoxyazetidine-1-carboxamide;

(R)—N-(5-(2-(2-chloro-5-fluorophenyl)pyrrolidin-1-yl)pyrazolo[1,5-a]pyrimidin-3-yl)-3-hydroxy-3-methylazetidine-1-carboxamide;

(R)—N-(5-(2-(2-chloro-5-fluorophenyl)pyrrolidin-1-yl)pyrazolo[1,5-a]pyrimidin-3-yl)morpholine-4-carboxamide;

(S)-tert-butyl 4-(5-((R)-2-(2-chloro-5-fluorophenyl)pyrrolidin-1-yl)pyrazolo[1,5-a]pyrimidin-3-ylcarbamoyl)-2-methylpiperazine-1-carboxylate;

(S)—N-(5-((R)-2-(2-chloro-5-fluorophenyl)pyrrolidin-1-yl)pyrazolo[1,5-a]pyrimidin-3-yl)-3-methylpiperazine-1-carboxamide;

(R)—N-(5-(2-(2,5-difluorophenyl)pyrrolidin-1-yl)pyrazolo[1,5-a]pyrimidin-3-yl)-4-isopropylpiperazine-1-carboxamide;

(R)—N-(5-(2-(2,5-difluorophenyl)pyrrolidin-1-yl)pyrazolo[1,5-a]pyrimidin-3-yl)-4-ethylpiperazine-1-carboxamide;

(R)—N-(5-(2-(2,5-difluorophenyl)pyrrolidin-1-yl)pyrazolo[1,5-a]pyrimidin-3-yl)-4-methylpiperazine-1-carboxamide;

N-(5-((R)-2-(2,5-difluorophenyl)pyrrolidin-1-yl)pyrazolo[1,5-a]pyrimidin-3-yl)-3,5-dimethylpiperazine-1-carboxamide;

(S)-tert-butyl 4-(5-((R)-2-(2,5-difluorophenyl)pyrrolidin-1-yl)pyrazolo[1,5-a]pyrimidin-3-ylcarbamoyl)-2-methylpiperazine-1-carboxylate;

(S)—N-(5-((R)-2-(2,5-difluorophenyl)pyrrolidin-1-yl)pyrazolo[1,5-a]pyrimidin-3-yl)-3-methylpiperazine-1-carboxamide hydrochloride;

(R)—N-(5-(2-(3-fluorophenyl)pyrrolidin-1-yl)pyrazolo[1,5-a]pyrimidin-3-yl)-3-hydroxyazetidine-1-carboxamide;

(R)-methyl 1-(5-(2-(2,5-difluorophenyl)pyrrolidin-1-yl)pyrazolo[1,5-a]pyrimidin-3-ylcarbamoyl)cyclopropanecarboxylate;

(R)-1-(5-(2-(2,5-difluorophenyl)pyrrolidin-1-yl)pyrazolo[1,5-a]pyrimidin-3-ylcarbamoyl)cyclopropanecarboxylic acid;

(S)—N-(5-((R)-2-(3-chloro-5-fluorophenyl)pyrrolidin-1-yl)pyrazolo[1,5-a]pyrimidin-3-yl)-3-hydroxypyrrolidine-1-carboxamide;

(R)—N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide;

(S)—N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide;

(R)—N-(5-(2-(2-(difluoromethyl)-5-fluorophenyl)pyrrolidin-1-yl)pyrazolo[1,5-a]pyrimidin-3-yl)-4-hydroxypiperidine-1-carboxamide;

(R)—N-(5-((R)-2-(2-(difluoromethyl)-5-fluorophenyl)pyrrolidin-1-yl)pyrazolo[1,5-a]pyrimidin-3-yl)-3-hydroxypiperidine-1-carboxamide;

(S)—N-(5-((R)-2-(2-(difluoromethyl)-5-fluorophenyl)pyrrolidin-1-yl)pyrazolo[1,5-a]pyrimidin-3-yl)-3-hydroxypiperidine-1-carboxamide;

(R)—N-(5-((R)-2-(2-chloro-5-fluorophenyl)pyrrolidin-1-yl)pyrazolo[1,5-a]pyrimidin-3-yl)-3-hydroxypyrrolidine-1-carboxamide;

(R)—N-(5-(2-(2-chloro-5-fluorophenyl)pyrrolidin-1-yl)pyrazolo[1,5-a]pyrimidin-3-yl)-4-hydroxypiperidine-1-carboxamide;

(R)—N-(5-((R)-2-(2-chloro-5-fluorophenyl)pyrrolidin-1-yl)pyrazolo[1,5-a]pyrimidin-3-yl)-3-hydroxypiperidine-1-carboxamide;

(S)—N-(5-((R)-2-(2-chloro-5-fluorophenyl)pyrrolidin-1-yl)pyrazolo[1,5-a]pyrimidin-3-yl)-3-hydroxypiperidine-1-carboxamide;

(R)—N-(5-(2-(2,5-difluorophenyl)pyrrolidin-1-yl)pyrazolo[1,5-a]pyrimidin-3-yl)pivalamide;

(R)-tert-butyl 3-(5-(2-(2-chloro-5-fluorophenyl)pyrrolidin-1-yl)pyrazolo[1,5-a]pyrimidin-3-ylcarbamoyl)azetidine-1-carboxylate;

(R)—N-(5-(2-(2-chloro-5-fluorophenyl)pyrrolidin-1-yl)pyrazolo[1,5-a]pyrimidin-3-yl)azetidine-3-carboxamide;

(R)-tert-butyl 4-(5-(2-(2-chloro-5-fluorophenyl)pyrrolidin-1-yl)pyrazolo[1,5-a]pyrimidin-3-ylcarbamoyl)-4-methylpiperidine-1-carboxylate;

(R)—N-(5-(2-(2-chloro-5-fluorophenyl)pyrrolidin-1-yl)pyrazolo[1,5-a]pyrimidin-3-yl)-4-methylpiperidine-4-carboxamide;

(R)—N-(5-(2-(2,5-difluorophenyl)pyrrolidin-1-yl)pyrazolo[1,5-a]pyrimidin-3-yl)-2-hydroxy-2-methylpropanamide;

(R)—N-(5-(2-(2,5-difluorophenyl)pyrrolidin-1-yl)pyrazolo[1,5-a]pyrimidin-3-yl)-1-(trifluoromethyl)cyclopropanecarboxamide;

(R)-1-cyano-N-(5-(2-(2,5-difluorophenyl)pyrrolidin-1-yl)pyrazolo[1,5-a]pyrimidin-3-yl)cyclopropanecarboxamide;

(R)—N-(5-((R)-2-(2,5-difluorophenyl)pyrrolidin-1-yl)pyrazolo[1,5-a]pyrimidin-3-yl)-2-methylpyrrolidine-2-carboxamide;

(R)—N-(5-(2-(2,5-difluorophenyl)pyrrolidin-1-yl)pyrazolo[1,5-a]pyrimidin-3-yl)-2-fluoro-2-methylpropanamide;

(R)—N-(5-(2-(2,5-difluorophenyl)pyrrolidin-1-yl)pyrazolo[1,5-a]pyrimidin-3-yl)-2-(isopropylamino)thiazole-4-carboxamide;

(R)—N-(5-(2-(2,5-difluorophenyl)pyrrolidin-1-yl)pyrazolo[1,5-a]pyrimidin-3-yl)-2-methyl-2-(1H-1,2,4-triazol-1-yl)propanamide;

(R)—N-(5-(2-(2,5-difluorophenyl)pyrrolidin-1-yl)pyrazolo[1,5-a]pyrimidin-3-yl)pyrazine-2-carboxamide;

(R)—N-(5-(2-(2,5-difluorophenyl)pyrrolidin-1-yl)pyrazolo[1,5-a]pyrimidin-3-yl)-5-methylpyrazine-2-carboxamide;

(R)—N-(5-(2-(2,5-difluorophenyl)pyrrolidin-1-yl)pyrazolo[1,5-a]pyrimidin-3-yl)picolinamide;

(R)—N-(5-(2-(2,5-difluorophenyl)pyrrolidin-1-yl)pyrazolo[1,5-a]pyrimidin-3-yl)-6-methylpicolinamide;

(R)-5-chloro-N-(5-(2-(2,5-difluorophenyl)pyrrolidin-1-yl)pyrazolo[1,5-a]pyrimidin-3-yl)picolinamide;

(R)-4-chloro-N-(5-(2-(2,5-difluorophenyl)pyrrolidin-1-yl)pyrazolo[1,5-a]pyrimidin-3-yl)picolinamide;

(R)—N-(5-(2-(2,5-difluorophenyl)pyrrolidin-1-yl)pyrazolo[1,5-a]pyrimidin-3-yl)-3-methylpicolinamide;

(R)—N-(5-(2-(2,5-difluorophenyl)pyrrolidin-1-yl)pyrazolo[1,5-a]pyrimidin-3-yl)-3-hydroxy-2,2-dimethylpropanamide;

(R)—N-(5-(2-(2,5-difluorophenyl)pyrrolidin-1-yl)pyrazolo[1,5-a]pyrimidin-3-yl)-1-hydroxycyclopropanecarboxamide;

(R)—N-(5-(2-(2,5-difluorophenyl)pyrrolidin-1-yl)pyrazolo[1,5-a]pyrimidin-3-yl)-2-methyl-2-(methylamino)propanamide;

(R)—N-(5-(2-(2,5-difluorophenyl)pyrrolidin-1-yl)pyrazolo[1,5-a]pyrimidin-3-yl)pyrimidine-2-carboxamide;

(R)—N-(5-(2-(3-fluorophenyl)pyrrolidin-1-yl)pyrazolo[1,5-a]pyrimidin-3-yl)picolinamide;

(R)—N-(5-(2-(3-fluorophenyl)pyrrolidin-1-yl)pyrazolo[1,5-a]pyrimidin-3-yl)-3-methylpicolinamide;

(R)—N-(5-(2-(3-fluorophenyl)pyrrolidin-1-yl)pyrazolo[1,5-a]pyrimidin-3-yl)-1-methyl-2-oxo-1,2-dihydropyridine-4-carboxamide;

(R)-6-chloro-N-(5-(2-(2,5-difluorophenyl)pyrrolidin-1-yl)pyrazolo[1,5-a]pyrimidin-3-yl)picolinamide;

(R)-4-(ethylsulfonamido)-N-(5-(2-(3-fluorophenyl)pyrrolidin-1-yl)pyrazolo[1,5-a]pyrimidin-3-yl)benzamide;

(R)—N-(5-(2-(3-fluorophenyl)pyrrolidin-1-yl)pyrazolo[1,5-a]pyrimidin-3-yl)-1-methyl-1H-pyrazole-3-carboxamide;

(R)—N-(5-(2-(3-fluorophenyl)pyrrolidin-1-yl)pyrazolo[1,5-a]pyrimidin-3-yl)-1H-pyrazole-3-carboxamide;

(R)—N-(5-(2-(3-fluorophenyl)pyrrolidin-1-yl)pyrazolo[1,5-a]pyrimidin-3-yl)-6-methoxypicolinamide;

(R)—N-(5-(2-(3-fluorophenyl)pyrrolidin-1-yl)pyrazolo[1,5-a]pyrimidin-3-yl)nicotinamide;

(R)—N-(5-(2-(3-fluorophenyl)pyrrolidin-1-yl)pyrazolo[1,5-a]pyrimidin-3-yl)isonicotinamide;

(R)—N-(5-(2-(3-fluorophenyl)pyrrolidin-1-yl)pyrazolo[1,5-a]pyrimidin-3-yl)-6-methylnicotinamide;

(R)—N-(5-(2-(3-fluorophenyl)pyrrolidin-1-yl)pyrazolo[1,5-a]pyrimidin-3-yl)-2-methoxynicotinamide;

(R)—N-(5-(2-(3-fluorophenyl)pyrrolidin-1-yl)pyrazolo[1,5-a]pyrimidin-3-yl)-3-methylisonicotinamide;

(S)—N-(5-((R)-2-(2-chloro-5-fluorophenyl)pyrrolidin-1-yl)pyrazolo[1,5-a]pyrimidin-3-yl)-3-hydroxypyrrolidine-1-carboxamide;

(R)—N-(5-(2-(3-fluorophenyl)pyrrolidin-1-yl)pyrazolo[1,5-a]pyrimidin-3-yl)-5-methylpyrazine-2-carboxamide;

(R)—N-(5-(2-(3-fluorophenyl)pyrrolidin-1-yl)pyrazolo[1,5-a]pyrimidin-3-yl)-1-methyl-1H-imidazole-2-carboxamide;

(S)—N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide;

(R)—N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide;

(R)—N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide;

(S)—N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide;

(S)—N-(5-((R)-2-(5-fluoropyridin-3-yl)pyrrolidin-1-yl)pyrazolo[1,5-a]pyrimidin-3-yl)-3-hydroxypyrrolidine-1-carboxamide;

(R)—N-(5-((R)-2-(5-fluoropyridin-3-yl)pyrrolidin-1-yl)pyrazolo[1,5-a]pyrimidin-3-yl)-3-hydroxypyrrolidine-1-carboxamide;

(S)—N-(5-((R)-2-(5-fluoro-2-methoxyphenyl)pyrrolidin-1-yl)pyrazolo[1,5-a]pyrimidin-3-yl)-3-hydroxypyrrolidine-1-carboxamide;

(S)—N-(5-((R)-2-(5-fluoro-2-methoxyphenyl)pyrrolidin-1-yl)pyrazolo[1,5-a]pyrimidin-3-yl)-3-hydroxypiperidine-1-carboxamide;

(1S,4S)—N-(5-((R)-2-(2,5-difluorophenyl)pyrrolidin-1-yl)pyrazolo[1,5-a]pyrimidin-3-yl)-2-oxa-5-azabicyclo[2.2.1]heptane-5-carboxamide;

(R)—N-(5-((R)-2-(2,5-difluorophenyl)pyrrolidin-1-yl)pyrazolo[1,5-a]pyrimidin-3-yl)-3-hydroxypyrrolidine-1-carboxamide;

(1S,3R)—N-(5-((R)-2-(2,5-difluorophenyl)pyrrolidin-1-yl)pyrazolo[1,5-a]pyrimidin-3-yl)-3-hydroxycyclopentanecarboxamide;

(1S,3S)—N-(5-((R)-2-(2,5-difluorophenyl)pyrrolidin-1-yl)pyrazolo[1,5-a]pyrimidin-3-yl)-3-hydroxycyclopentanecarboxamide;

(R)—N-(5-(2-(2,5-difluorophenyl)pyrrolidin-1-yl)pyrazolo[1,5-a]pyrimidin-3-yl)-3-hydroxycyclobutanecarboxamide;

(R)—$N^1$-(5-(2-(2,5-difluorophenyl)pyrrolidin-1-yl)pyrazolo[1,5-a]pyrimidin-3-yl)-$N^2,N^2$-dimethyloxalamide;

(R)—$N^1$-(5-(2-(2,5-difluorophenyl)pyrrolidin-1-yl)pyrazolo[1,5-a]pyrimidin-3-yl)-$N^2$-methyloxalamide;

(R)—$N^1$-(5-(2-(2,5-difluorophenyl)pyrrolidin-1-yl)pyrazolo[1,5-a]pyrimidin-3-yl)oxalamide;

(R)—$N^1$-cyclopropyl-N2-(5-(2-(2,5-difluorophenyl)pyrrolidin-1-yl)pyrazolo[1,5-a]pyrimidin-3-yl)oxalamide;

(R)—N-(5-(2-(2,5-difluorophenyl)pyrrolidin-1-yl)pyrazolo[1,5-a]pyrimidin-3-yl)-2-(3-hydroxyazetidin-1-yl)-2-oxoacetamide;

N-(5-((R)-2-(2,5-difluorophenyl)pyrrolidin-1-yl)pyrazolo[1,5-a]pyrimidin-3-yl)-2-((S)-3-hydroxypyrrolidin-1-yl)-2-oxoacetamide;

(R)—N-(5-(2-(2,5-difluorophenyl)pyrrolidin-1-yl)pyrazolo[1,5-a]pyrimidin-3-yl)-2-morpholino-2-oxoacetamide;

(R)-methyl 2-(5-(2-(2,5-difluorophenyl)pyrrolidin-1-yl)pyrazolo[1,5-a]pyrimidin-3-ylamino)-2-oxoacetate;

(R)-2-(5-(2-(2,5-difluorophenyl)pyrrolidin-1-yl)pyrazolo[1,5-a]pyrimidin-3-ylamino)-2-oxoacetic acid;

and salts thereof.

Particular examples of salts of the above compounds include hydrogen sulfate salts, hydrochloride salts and trifluoroacetate salts.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Acronyms found in the examples have the following meanings.

| | |
|---|---|
| CDI | carbonyldiimidazole |
| DIEA | diisopropylethylamine |
| DCM | dichloromethane |
| DME | dimethoxyethane |
| DMF | dimethylformamide |
| DMSO | dimethylsulfoxide |
| HATU | O-(7-azabenzotriazol-1-yl)-1,1,3,3-tetramethyluronium hexafluorophosphate |
| PS-DMAP | polystyrene-bound dimethylaminopyridine |
| TFA | trifluoroacetic acid |

Example A

TrkA ELISA Assay

An enzyme-linked immunosorbant assay (ELISA) was used to assess TrkA kinase activity in the presence of inhibitors. Immulon 4HBX 384-well microtiter plates (Thermo part #8755) were coated with a 0.025 mg/mL solution of poly(Glu, Ala, Tyr; 6:3:1; Sigma P3899). Various concentrations of test compound, 2.5 nM TrkA (Invitrogen Corp., histidine-tagged recombinant human TrkA, cytoplasmic domain), and 500 μM ATP were incubated for 25 minutes at ambient temperature in the coated plates while shaking. The assay buffer consisted of 25 mM MOPS pH 7.5, 0.005% (v/v) Triton X-100 and 5 mM MgCl$_2$. The reaction mixture was removed from the plate by washing with PBS containing 0.1% (v/v) Tween 20. The phosphorylated reaction product was detected using 0.2 µg/mL of a phosphotyrosine specific monoclonal antibody (clone PY20) conjugated to horseradish peroxidase in conjunction with the TMB Peroxidase Substrate System (KPL). After the addition of 1M phosphoric acid, the chromogenic substrate color intensity was quantitated via absorbance at 450 nm. $IC_{50}$ values were calculated using either a 4 or 5-parameter logistic curve fit.

In this assay, compounds of the invention had an average $IC_{50}$ below 1000 nM. Certain compounds had an average $IC_{50}$ below 100 nM. Table 1 provides specific $IC_{50}$ values for compounds of this invention when tested in this assay.

TABLE 1

| Example No. | TrkA Elisa Enzyme $IC_{50}$ (nM) |
|---|---|
| 1 | 20.7 |
| 2 | 15.8 |
| 3 | 22.2 |
| 4 | 5 |
| 5 | 12.1 |
| 6 | 19.2 |
| 7 | 77.5 |
| 8 | 13.7 |
| 9 | 820.8 |
| 10 | 187.9 |
| 11 | 171 |
| 12 | 26.5 |
| 13 | 32.2 |
| 14 | 9.7 |
| 15 | 13.3 |
| 16 | 27.5 |
| 17 | 19.7 |
| 18 | 4.6 |
| 19 | 10.1 |
| 20 | 4.8 |
| 21 | 27.9 |
| 22 | 11.5 |
| 23 | 41.7 |
| 24 | 55 |
| 25 | 82.3 |
| 26 | 45 |
| 27 | 106.7 |
| 28 | 57.4 |
| 29 | 98 |
| 30 | 153.7 |
| 31 | 88.3 |
| 32 | 115.6 |
| 33 | 4.7 |
| 34 | 98.2 |
| 35 | 20.2 |
| 36 | 18 |
| 37 | 8.7 |
| 38 | 85.5 |
| 39 | 25.7 |
| 40 | 30.8 |
| 41 | 4.1 |
| 42 | 28.3 |
| 43 | 11.7 |
| 44 | 13.4 |
| 45 | 6.3 |
| 46 | 37.3 |
| 47 | 190.3 |
| 48 | 15.3 |
| 49 | 29.2 |
| 50 | 12.4 |
| 51 | 5.2 |
| 52 | 4.2 |
| 53 | 31 |
| 54 | 14.2 |
| 55 | 3.1 |
| 56 | 14.4 |
| 57 | 2.2 |
| 58 | 3.1 |
| 59 | 1.7 |
| 60 | 4.2 |
| 61 | 4 |
| 62 | 4 |
| 63 | 1.7 |
| 64 | 7.5 |
| 65 | 16.5 |
| 66 | 52.5 |
| 67 | 3 |
| 68 | 4 |
| 69 | 6.2 |
| 70 | 55.6 |
| 71 | 3.5 |
| 72 | 45.5 |
| 73 | 8.5 |
| 74 | 15.3 |
| 75 | 7.4 |
| 76 | 53.3 |
| 77 | 71.8 |
| 78 | 47 |
| 79 | 5.7 |
| 80 | 320.2 |
| 81 | 8 |
| 82 | 6.6 |
| 83 | 35.4 |
| 84 | 3.2 |
| 85 | 5.7 |
| 86 | 14 |
| 87 | 14.6 |
| 88 | 156.1 |
| 89 | 896.1 |
| 90 | 11.3 |
| 91 | 10.2 |
| 92 | 107.4 |
| 93 | 28.5 |
| 94 | 20.3 |
| 95 | 42.5 |
| 96 | 27.4 |
| 97 | 47.45 |
| 98 | 7.65 |
| 99 | 4.65 |
| 100 | 15.85 |
| 101 | 10.1 |
| 102 | 12.75 |
| 103 | 82.4 |
| 104 | 7.65 |
| 105 | 4.7 |

Example B

TrkA and TrkB Omnia Assay

Trk enzymatic selectivity was assessed using Omnia™ Kinase Assay reagents from Invitrogen Corp. Enzyme (either TrkA or TrkB from Invitrogen Corp.) and test compound (various concentrations) were incubated for 10 minutes at ambient temperature in a 384-well white polypropylene plate (Nunc catalog # 267462). Omnia Tyr Peptide #4 (for TrkA) or #5 (for TrkB), as well as ATP, were then added to the plate. Final concentrations were as follows: 20 nM enzyme, 500 µM of ATP for TrkA assay or 1 mM ATP for TrkB assay, 10 µM peptide substrate. The assay buffer consisted of 25 mM MOPS pH 7.5, 0.005% (v/v) Triton X-100 and 5 mM $MgCl_2$. The production of phosphorylated peptide was monitored continuously for 70 minutes using a Molecular Devices Flex-Station $II^{384}$ microplate reader (excitation=360 nm; emission=485 nm). Initial rates were calculated from the progress curves. $IC_{50}$ values were then calculated from these rates using either a 4 or 5-parameter logistic curve fit.

Preparation A

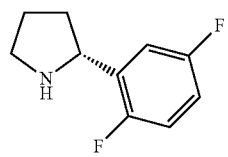 [SMILES: Fc1ccc(F)c([C@H]2CCCN2)c1]

Preparation of (R)-2-(2,5-difluorophenyl)pyrrolidine

Step A: Preparation of (R)-tert-butyl 2-(2,5-difluorophenyl)pyrrolidine-1-carboxylate: A solution of tert-butylpyrrolidine-1-carboxylate (20 g, 116.8 mmol) and (−)sparteine (32.9, 140 mmol) in MTBE (360 mL) was cooled to −78° C., and sec-BuLi (100 mL, 140 mmol, 1.4 M in cyclohexane) was introduced dropwise via cannula, keeping the internal temperature under −70° C. The resulting solution was stirred for 3 hours at −78° C., followed by addition of a solution of $ZnCl_2$ (93.4 mL, 93.4 mmol, 1M in $Et_2O$) drop-wise with rapid stirring, keeping the internal temperature below −65° C. The resulting light suspension was stirred at −78° C. for 30 minutes and then warmed to ambient temperature. The resulting mixture was charged with 2-bromo-1,4-difluorobenzene (14.5 mL, 128 mmol), followed by $Pd(OAc)_2$ (1.31 g, 5.8 mmol) and $t-Bu_3P$—$HBF_4$ (2.03 g, 7.0 mmol) in one portion. After stirring overnight at ambient temperature, 10.5 mL of $NH_4OH$ solution was added and the reaction was stirred for another hour. The resulting slurry was filtered through CELITE and washed with $Et_2O$ (1 L). The filtrate was washed with HCl (0.5 L, 1M aq.) and brine. The organic layer was filtered and concentrated, and the crude product was purified by silica column chromatography, eluting with 5-10% EtOAc/hexanes to give product (R)-tert-butyl 2-(2,5-difluorophenyl)pyrrolidine-1-carboxylate as yellow oil (23.9 g, 72% yield).

Step B: Preparation of (R)-2-(2,5-difluorophenyl)pyrrolidine: To (R)-tert-butyl 2-(2,5-difluorophenyl)pyrrolidine-1-carboxylate (23.9 g, 84.4 mmol) was added 56.2 mL 4N HCl (dioxane). After stirring at ambient temperature for 2 hours, 200 mL of ether was added and the mixture was stirred for 10 minutes. The resulting slurry was filtered, yielding the hydrochloride salt of the product as a white solid (17.2 g). To obtain the free base, the HCl salt product was dispersed in a mixture of EtOAc (200 mL) and NaOH solution (100 mL, 2 N aq.) The layers were separated and the aqueous layer was extracted with EtOAc. The combined organic extracts were filtered and concentrated to give the desired product as a liquid (13.2 g, 85% yield).

Step C: Determination of Enantiomeric Excess (ee %) of (R)-2-(2,5-difluorophenyl)pyrrolidine: To an ethanol solution of (R)-2-(2,5-difluorophenyl)pyrrolidine was added excess N-(2,4-dinitro-5-fluorophenyl)-L-alanine amide (FDAA, Marfey's reagent). The mixture was heated to reflux for approximately two minutes. After cooling to ambient temperature, the reaction mixture was diluted with acetonitrile and injected onto HPLC (YMC ODS-AQ 4.6×50 mm 3 μm 120 Å column; mobile phase: 5-95% solvent B in A; solvent A: $H_2O$/1% IPA/10 mM ammonium acetate, and solvent B: ACN/1% IPA/10 mM ammonium acetate; flow rate: 2 mL/min) to determine the enantiomeric excess of the product by calculating the peak areas of the two diastereomeric derivatives formed. A 1:1 racemic sample was prepared according the same procedure described herein, replacing (R)-2-(2,5-difluorophenyl)pyrrolidine with (rac)-2-(2,5-difluorophenyl)pyrrolidine. The ee % of the product obtained as described above was determined to be >93%.

Preparation B

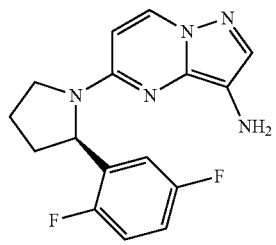 [SMILES: Nc1cnn2ccc(N3CCC[C@@H]3c3cc(F)ccc3F)nc12]

Preparation of (R)-5-(2-(2,5-difluorophenyl)pyrrolidin-1-yl)pyrazolo[1,5-a]pyrimidin-3-amine Step A: Preparation of (R)-5-(2-(2,5-difluorophenyl)pyrrolidin-1-yl)pyrazolo[1,5-a]pyrimidine: In a pressure reaction tube was added 5-chloropyrazolo[1,5-a]pyrimidine (4.2 g, 27 mmol), (R)-2-(2,5-difluorophenyl)pyrrolidine (Preparation A; 5.3 g, 29 mmol), anhydrous n-butanol (5 ml, 55 mmol), and DIEA (9.5 ml, 55 mmol). The yellowish suspension was sealed and heated in an oil bath (160° C.) overnight. The reaction was cooled to ambient temperature, diluted with EtOAc (250 mL), and filtered, rinsing the solid with EtOAc. The filtrate (330 mL) was washed with water (2×150 mL), brine (100 mL), concentrated, and purified by silica chromatography, eluting with 2:1 EtOAc/hexanes to give the product as a bright yellowish solid (5.6 g, 68% yield).

Step B: Preparation of (R)-5-(2-(2,5-difluorophenyl)pyrrolidin-1-yl)-3-nitropyrazolo[1,5-a]pyrimidine: (R)-5-(2-(2,5-difluorophenyl)pyrrolidin-1-yl)pyrazolo[1,5-a]pyrimidine (3.3 g, 10.99 mmol), was dissolved in 25 mL TFA at ambient temperature to give a clear yellowish solution, then nitric acid (3.434 mL, 54.94 mmol) was added drop-wise to the solution with rapid stirring. After addition, the reaction mixture was stirred for another 15 minutes at ambient temperature, then quenched by pouring onto ice with rapid stirring. The resulting yellowish suspension was filtered, rinsed with water, then the solid was triturated with MeOH (50 mL, with brief sonication), and vacuum-filtered, giving the pure product as a fine off-white powder (2.2 g, 58% yield).

Step C: Preparation of (R)-5-(2-(2,5-difluorophenyl)pyrrolidin-1-yl)pyrazolo[1,5-a]pyrimidin-3-amine: To a yellowish solution of (R)-5-(2-(2,5-difluorophenyl)pyrrolidin-1-yl)-3-nitropyrazolo[1,5-a]pyrimidine (2.3 g, 6.66 mmol), in a 1:1 mixture of MeOH/DCM (30 mL/30 mL) was added Zn dust (4.36 g, 66.6 mmol) [<10 micron, Aldrich] while stirring. Saturated $NH_4Cl$ aqueous solution (30 mL) was added dropwise to this suspension with rapid stirring. After $NH_4Cl$ addition was complete, the reaction mixture was allowed to cool to ambient temperature and stirred for another 15 minutes. The reaction was diluted with DCM (50 mL) and filtered through a GF/F paper, rinsing the wet cake with DCM. The organic layer of the filtrate was separated, and the aqueous layer was extracted with DCM (2×50 mL). The organic layers were combined, washed with brine (100 mL), dried over Na₂SO₄, and concentrated, to provide the basically pure product as a brownish foamy solid (2.08 g, 99% yield), which was used without further purification.

Example 1

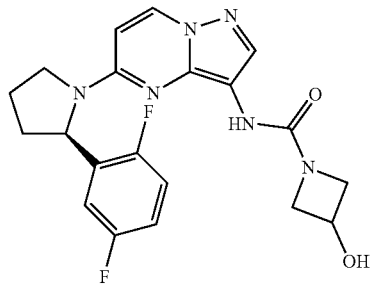 [SMILES: O=C(Nc1cnn2ccc(N3CCC[C@@H]3c3cc(F)ccc3F)nc12)N1CC(O)C1]

(R)—N-(5-(2-(2,5-difluorophenyl)pyrrolidin-1-yl)pyrazolo[1,5-a]pyrimidin-3-yl)-3-hydroxyazetidine-1-carboxamide To a DCM (1.0 mL) solution of (R)-5-(2-(2,5-difluorophenyl)pyrrolidin-1-yl)pyrazolo[1,5-a]pyrimidin-3-amine (Preparation B; 50 mg, 0.16 mmol), was added CDI (39 mg, 0.24 mmol) at ambient temperature in one portion. After stirring two hours, azetidin-3-ol hydrochloride (35 mg, 0.32 mmol) [purchased from Oakwood] was added in one portion, followed by addition of DIEA (0.083 mL, 0.48 mmol). After stirring for 5 minutes, the reaction was concentrated and directly purified by reverse-phase column chromatography, eluting with 5 to 48% acetonitrile/water to yield the final product as a yellowish foamy powder (66 mg, 100% yield). MS (apci) m/z=415.2 (M+H).

Example 1A

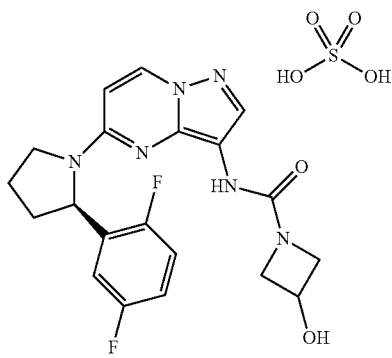 [SMILES: O=C(Nc1cnn2ccc(N3CCC[C@@H]3c3cc(F)ccc3F)nc12)N1CC(O)C1 ; O=S(=O)(O)O]

(R)—N-(5-(2-(2,5-difluorophenyl)pyrrolidin-1-yl)pyrazolo[1,5-a]pyrimidin-3-yl)-3-hydroxyazetidine-1-carboxamide sulfate To a solution of (R)—N-(5-(2-(2,5-difluorophenyl)pyrrolidin-1-yl)pyrazolo[1,5-a]pyrimidin-3-yl)-3-hydroxyazetidine-1-carboxamide (44 mg, 0.11 mmol) in methanol (3 mL) at ambient temperature was added sulfuric acid in methanol (531 µL, 0.11 mmol). The resulting solution was stirred for 30 minutes then concentrated to provide (R)—N-(5-(2-(2,5-difluorophenyl)pyrrolidin-1-yl)pyrazolo[1,5-a]pyrimidin-3-yl)-3-hydroxyazetidine-1-carboxamide sulfate (38 mg, 0.074 mmol, 70% yield) as a yellow solid.

Example 1B

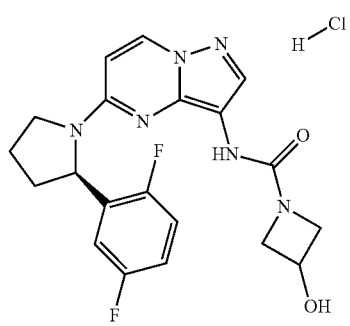 [SMILES: O=C(Nc1cnn2ccc(N3CCC[C@@H]3c3cc(F)ccc3F)nc12)N1CC(O)C1 ; Cl]

(R)—N-(5-(2-(2,5-difluorophenyl)pyrrolidin-1-yl)pyrazolo[1,5-a]pyrimidin-3-yl)-3-hydroxyazetidine-1-carboxamide hydrochloride To a methanol (1 mL) solution of (R)—N-(5-(2-(2,5-difluorophenyl)pyrrolidin-1-yl)pyrazolo[1,5-a]pyrimidin-3-yl)-3-hydroxyazetidine-1-carboxamide (5.2 mg, 0.013 mmol) was added HCl as a solution is dioxane (30 µL). After 30 minutes, the reaction was concentrated to provide (R)—N-(5-(2-(2,5-difluorophenyl)pyrrolidin-1-yl)pyrazolo[1,5-a]pyrimidin-3-yl)-3-hydroxyazetidine-1-carboxamide hydrochloride (5.7 mg, 0.013 mmol, 101% yield) as a yellow solid.

Example 2

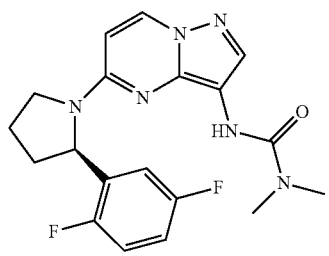 [SMILES: CN(C)C(=O)Nc1cnn2ccc(N3CCC[C@@H]3c3cc(F)ccc3F)nc12]

(R)-3-(5-(2-(2,5-difluorophenyl)pyrrolidin-1-yl)pyrazolo[1,5-a]pyrimidin-3-yl)-1,1-dimethylurea To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, dimethylamine (0.095 mL×2 N THF, 0.19 mmol) was added in one portion. The reaction was stirred for 5 minutes, then concentrated, and the residue was directly purified by reverse-phase column chromatography, eluting with 0 to 60% acetonitrile/water to yield the final product as a yellowish foamy powder (33 mg, 90% yield). MS (apci) m/z=387.2 (M+H).

Example 2A

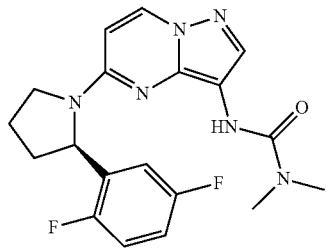 [SMILES: CN(C)C(=O)Nc1cnn2ccc(N3CCC[C@@H]3c3cc(F)ccc3F)nc12]

(R)-3-(5-(2-(2,5-difluorophenyl)pyrrolidin-1-yl)pyrazolo[1,5-a]pyrimidin-3-yl)-1,1-dimethylurea hydrochloride To a methanol (1 mL) solution of (R)-3-(5-(2-(2,5-difluorophenyl)pyrrolidin-1-yl)pyrazolo[1,5-a]pyrimidin-3-yl)-1,1-dimethylurea (8.5 mg, 0.022 mmol) was added HCl as a solution is dioxane (30 μL). After 30 minutes, the reaction was concentrated to provide (R)-3-(5-(2-(2,5-difluorophenyl)pyrrolidin-1-yl)pyrazolo[1,5-a]pyrimidin-3-yl)-1,1-dimethylurea hydrochloride (6.7 mg, 0.016 mmol, 72% yield) as a yellow solid.

Example 3

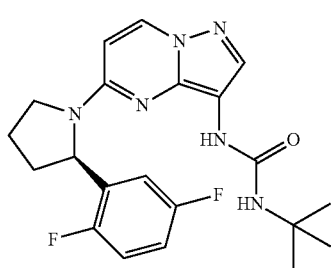 [SMILES: CC(C)(C)NC(=O)Nc1cnn2ccc(N3CCC[C@@H]3c3cc(F)ccc3F)nc12]

(R)-1-tert-butyl-3-(5-(2-(2,5-difluorophenyl)pyrrolidin-1-yl)pyrazolo[1,5-a]pyrimidin-3-yl)urea To a DCM (0.8 mL) solution of (R)-5-(2-(2,5-difluorophenyl)pyrrolidin-1-yl)pyrazolo[1,5-a]pyrimidin-3-amine (Preparation B; 25 mg, 0.079 mmol) was added 2-isocyanato-2-methylpropane (9.4 mg, 0.095 mmol) at ambient temperature drop-wise, followed by addition of DIEA (0.028 mL, 0.16 mmol). The reaction was stirred for 4 hours then concentrated, and the residue was directly purified by reverse-phase column chromatography, eluting with 5 to 65% acetonitrile/water to yield the final product as a pale-yellowish solid (27 mg, 82% yield). MS (apci) m/z=415.1 (M+H).

Example 4

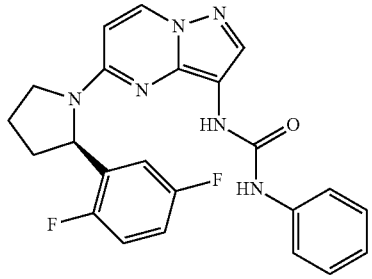 [SMILES: O=C(Nc1ccccc1)Nc1cnn2ccc(N3CCC[C@@H]3c3cc(F)ccc3F)nc12]

(R)-1-(5-(2-(2,5-difluorophenyl)pyrrolidin-1-yl)pyrazolo[1,5-a]pyrimidin-3-yl)-3-phenylurea To a DCM (0.8 mL) solution of (R)-5-(2-(2,5-difluorophenyl)pyrrolidin-1-yl)pyrazolo[1,5-a]pyrimidin-3-amine (Preparation B; 25 mg, 0.079 mmol) was added isocyanatobenzene (19 mg, 0.16 mmol) at ambient temperature dropwise. The reaction was stirred for 5 minutes then concentrated, and the residue was directly purified by reverse-phase column chromatography, eluting with 5 to 60% acetonitrile/water to yield the final product as a pale-yellowish solid (30 mg, 87% yield). MS (apci) m/z=435.2 (M+H).

Example 4A

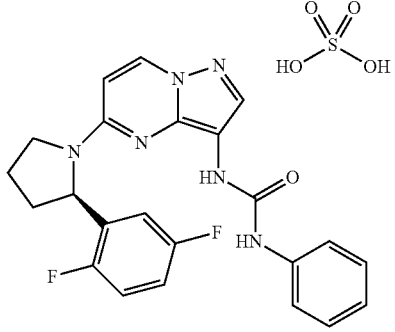 [SMILES: O=C(Nc1ccccc1)Nc1cnn2ccc(N3CCC[C@@H]3c3cc(F)ccc3F)nc12 ; O=S(=O)(O)O]

(R)-1-(5-(2-(2,5-difluorophenyl)pyrrolidin-1-yl)pyrazolo[1,5-a]pyrimidin-3-yl)-3-phenylurea sulfate To a solution of (R)-1-(5-(2-(2,5-difluorophenyl)pyrrolidin-1-yl)pyrazolo[1,5-a]pyrimidin-3-yl)-3-phenylurea (10.1 mg, 0.0232 mmol) in methanol (0.5 mL) at ambient temperature was added sulfuric acid in methanol (232 μL, 0.0232 mmol). The resulting solution was stirred for 30 minutes then concentrated to provide (R)-1-(5-(2-(2,5-difluorophenyl)pyrrolidin-1-yl)pyrazolo[1,5-a]pyrimidin-3-yl)-3-phenylurea sulfate (12 mg, 0.0225 mmol, 96.9% yield) as a yellow solid.

Example 5

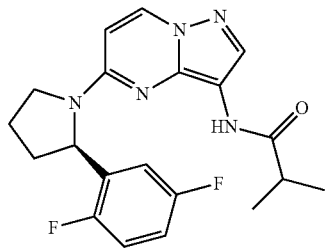 [SMILES: CC(C)C(=O)Nc1cnn2ccc(N3CCC[C@@H]3c3cc(F)ccc3F)nc12]

(R)—N-(5-(2-(2,5-difluorophenyl)pyrrolidin-1-yl)pyrazolo[1,5-a]pyrimidin-3-yl)isobutyramide A DCM (0.5 mL) solution of (R)-5-(2-(2,5-difluorophenyl)pyrrolidin-1-yl)pyrazolo[1,5-a]pyrimidin-3-amine (Preparation B; 20 mg, 0.063 mmol) was cooled in an ice bath, followed by addition of isobutyric anhydride (11.0 mg, 0.070 mmol) and pyridine (10 mg, 0.12 mmol) drop-wise. The reaction was allowed to warm up to ambient temperature and stirred for 1 hour. The reaction mixture was directly purified by reverse-phase column chromatography, eluting with 5 to 60% acetonitrile/water to yield the final product as a yellowish foamy solid (17 mg, 71%). MS (apci) m/z=386.2 (M+H).

Example 6

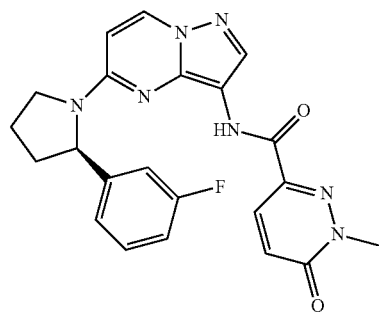 [SMILES: Cn1nc(C(=O)Nc2cnn3ccc(N4CCC[C@@H]4c4cccc(F)c4)nc23)ccc1=O]

(R)—N-(5-(2-(3-fluorophenyl)pyrrolidin-1-yl)pyrazolo[1,5-a]pyrimidin-3-yl)-1-methyl-6-oxo-1,6-dihydropyridazine-3-carboxamide Step A: Preparation of (R)-5-(2-(3-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step A with (R)-2-(3-fluorophenyl)pyrrolidine.

Step B: Preparation of (R)-2-(3-fluorophenyl)pyrrolidine: Prepared by the method of Preparation A, substituting 2-bromo-1,4-difluorobenzene with 1-bromo-3-fluorobenzene in step A.

Step C: Preparation of (R)—N-(5-(2-(3-fluorophenyl)pyrrolidin-1-yl)pyrazolo[1,5-a]pyrimidin-3-yl)-1-methyl-6-oxo-1,6-dihydropyridazine-3-carboxamide: To a mixture of (R)-5-(2-(3-fluorophenyl)pyrrolidin-1-yl)pyrazolo[1,5-a]pyrimidin-3-amine (30 mg, 0.10 mmol), 1-methyl-6-oxo-1,6-dihydropyridazine-3-carboxylic acid (34 mg, 0.22 mmol), and HATU (84 mg, 0.22 mmol) was added 0.8 mL DMF to make a solution. After cooling in an ice bath for 10 minutes, DIEA (0.053 mL, 0.30 mmol) was added to the reaction drop-wise. The reaction was allowed to warm up to ambient temperature and stirred overnight. The resulting fine yellowish suspension from the reaction mixture was filtered, rinsed with first DMF and then ether, to provide the final product as a yellowish solid (14.4 mg, 33% yield). MS (apci) m/z=434.2 (M+H).

Example 7

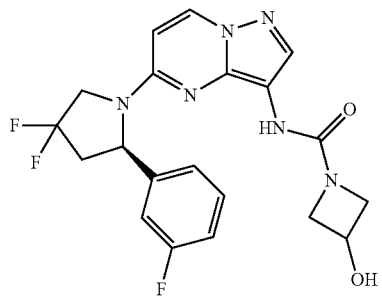 [SMILES: O=C(Nc1cnn2ccc(N3CC(F)(F)C[C@@H]3c3cccc(F)c3)nc12)N1CC(O)C1]

(R)—N-(5-(4,4-difluoro-2-(3-fluorophenyl)pyrrolidin-1-yl)pyrazolo[1,5-a]pyrimidin-3-yl)-3-hydroxyazetidine-1-carboxamide Steps A1-A6: Preparation of (R)-4,4-difluoro-2-(3-fluorophenyl)-pyrrolidine Step A1. Preparation of (R)-3-(tert-butyldimethylsilyloxy)-5-(3-fluorophenyl)-3,4-dihydro-2H-pyrrole: (3-Fluorophenyl)magnesium bromide (203.2 ml×0.5 M ether, 102 mmol) was slowly added (via syringe) to a solution of (R)-3-(tert-butyldimethylsilyloxy)-4-chlorobutanenitrile (9.5 g, 40.6 mmol) in 120 mL of MTBE. The reaction was stirred for two hours and then DME (35 ml) was slowly added over 15 minutes, followed by EtOH (23 mL). After stirring for overnight, brine and 1 M NaOH (50 mL each) were added to the reaction. After stirring for one hour, the reaction mixture was filtered through Celite, rinsing the solid with EtOAc. The filtrate was washed with 1 N NaOH and brine, filtered through Phase Separator filter paper, and concentrated, yielding the crude product, which was carried to the next step without further purification (12.8 g, 107% yield).

Step A2. Preparation of (3R,5R)-5-(3-fluorophenyl)pyrrolidin-3-ol: (R)-3-(tert-butyldimethylsilyloxy)-5-(3-fluorophenyl)-3,4-dihydro-2H-pyrrole (5.0 g, 17.0 mmol) was dissolved in 50 mL methanol and 10 mL AcOH and cooled to −40° C. NaBH$_4$ (1.6 g, 43 mmol) was slowly added in small portions. The reaction was allowed to warm to ambient temperature. Most of the solvent was removed by rotary evaporation. The reaction was taken up in 200 mL of EtOAc, washed with 1 N NaOH, and filtered through Phase Separator filter paper, and concentrated. The crude product was taken up in 20 mL of 2 N HCl in dioxane. The reaction was concentrated, taken up in 200 mL of EtOAc, washed with 1 N NaOH, filtered, and concentrated, yielding the crude product, which was carried to the next step without further purification (2.93 g, 95% yield).

Step A3. Preparation of (2R,4R)-tert-butyl 2-(3-fluorophenyl)-4-hydroxypyrrolidine-1-carboxylate: To a mixture of (3R,5R)-5-(3-fluorophenyl)pyrrolidin-3-ol (3.4 g, 18.8 mmol), di-tert-butyl dicarbonate (4.91 g, 22.5 mmol), and PS-DMAP (2.29 g, 18.8 mmol) were added 100 mL DCM and 50 mL THF, and the reaction was left to stand for one week with periodic sonication treatment. The mixture was filtered, concentrated, and purified by silica column chromatography, eluting with 2-10% MeOH/DCM to yield the pure product (4 g, 76% yield).

Step A4. Preparation of (R)-tert-butyl 2-(3-fluorophenyl)-4-oxopyrrolidine-1-carboxylate: (2R,4R)-tert-Butyl 2-(3-fluorophenyl)-4-hydroxypyrrolidine-1-carboxylate (1.4 g, 4.98 mmol) and Dess-Martin periodinane (2.53 g, 5.97 mmol) were mixed in 50 mL DCM and stirred at ambient temperature overnight. For workup, 20 mL 1N NaOH was added to reaction, and stirred for 30 minutes, followed by addition of 20 mL brine. The reaction mixture was extracted with several portions of DCM. The combined organic extracts were filtered through a Phase Separator filter paper, concentrated, and purified by reverse phase chromatography, eluting with 20-70% acetonitrile/water to yield the product as yellow oil (600 mg, 43% yield.)

Step A5. Preparation of (R)-tert-butyl 4,4-difluoro-2-(3-fluorophenyl)pyrrolidine-1-carboxylate: (R)-tert-butyl 2-(3-fluorophenyl)-4-oxopyrrolidine-1-carboxylate (200 mg, 0.72 mmol) and Bis(2-methoxyethyl)aminosulfur trifluoride (238 mg, 1.07 mmol) were mixed in 25 mL DCM and stirred at ambient temperature overnight. For workup, 5 mL 1N NaOH was added and the reaction stirred for 30 minutes. The reaction was filtered through Celite, rinsing with DCM. Brine (2 mL) was added to the filtrate and the mixture was filtered through a Biotage Phase Separator frit, washing with several portions of DCM. The combined organic extracts were concentrated and purified by reverse phase chromatography, eluting with 20-90% acetonitrile/water to yield the product as clear oil (180 mg, 83%).

Step A6. Preparation of (R)-4,4-difluoro-2-(3-fluorophenyl)pyrrolidine: To (R)-tert-butyl 4,4-difluoro-2-(3-fluorophenyl)pyrrolidine-1-carboxylate (180 mg, 0.6 mmol) in a pressure reaction tube was added a solution of HCl (2 mL, 4 N dioxane, 8 mmol), then the reaction was sealed and heated at 60° C. for 4 hours. For workup, the reaction was poured into a mixture of ice and 1 M NaOH, and extracted with several portions of EtOAc. The combined organic extracts were filtered through a Phase Separator filter paper and concentrated, yielding the final product as clear oil, which was used in the next step without further purification.

Step B: Preparation of (R)-5-(4,4-difluoro-2-(3-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step 1 with (R)-4,4-difluoro-2-(3-fluorophenyl)-pyrrolidine.

Step C: Preparation of (R)—N-(5-(4,4-difluoro-2-(3-fluorophenyl)pyrrolidin-1-yl)pyrazolo[1,5-a]pyrimidin-3-yl)-3-hydroxyazetidine-1-carboxamide: To a DCM (0.7 mL) solution of (R)-5-(4,4-difluoro-2-(3-fluorophenyl)pyrrolidin-1-yl)pyrazolo[1,5-a]pyrimidin-3-amine (25 mg, 0.074 mmol), was added CDI (18 mg, 0.11 mmol) at ambient temperature in one portion. After stirring two hours, azetidin-3-ol hydrochloride (16 mg, 0.15 mmol) was added in one portion, followed by addition of DIEA (0.039 mL, 0.22 mmol). The reaction was stirred overnight, then concentrated, and the residue was directly purified by reverse-phase column chromatography, eluting with 0 to 45% acetonitrile/water to yield the final product as a yellowish oil (15 mg, 48% yield). MS (apci) m/z=433.1 (M+H).

Example 8

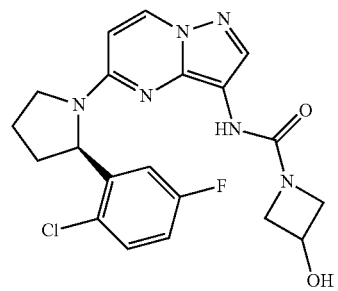 [SMILES: O=C(Nc1cnn2ccc(N3CCC[C@@H]3c3cc(F)ccc3Cl)nc12)N1CC(O)C1]

(R)—N-(5-(2-(2-chloro-5-fluorophenyl)pyrrolidin-1-yl)pyrazolo[1,5-a]pyrimidin-3-yl)-3-hydroxyazetidine-1-carboxamide Step A: Preparation of (R)-5-(2-(2-chloro-5-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step 1 with (R)-2-(2-chloro-5-fluorophenyl)pyrrolidine.

Step B: Preparation of (R)-2-(2-chloro-5-fluorophenyl)pyrrolidine: Prepared by the method of Preparation A, substituting 2-bromo-1,4-difluorobenzene with 2-bromo-1-chloro-4-fluorobenzene in Step A.

Step C: Preparation of (R)—N-(5-(2-(2-chloro-5-fluorophenyl)pyrrolidin-1-yl)pyrazolo[1,5-a]pyrimidin-3-yl)-3-hydroxyazetidine-1-carboxamide: To a DCM (0.8 mL) solution of (R)-5-(2-(2-chloro-5-fluorophenyl)pyrrolidin-1-yl)pyrazolo[1,5-a]pyrimidin-3-amine (30 mg, 0.090 mmol) was added CDI (29 mg, 0.18 mmol) at ambient temperature in one portion. After stirring two hours, azetidin-3-ol hydrochloride (20 mg, 0.18 mmol) was added in one portion, followed by addition of DIEA (0.047 mL, 0.27 mmol). The reaction was stirred for 5 minutes before it was concentrated and directly purified by reverse-phase column chromatography, eluting with 5 to 50% acetonitrile/water to yield the final product as a yellowish foamy powder (33 mg, 85% yield). MS (apci) m/z=431.1 (M+H).

Example 8A

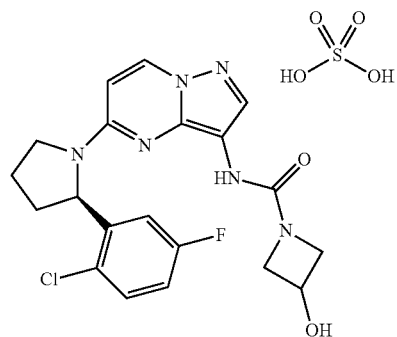

(R)—N-(5-(2-(2-chloro-5-fluorophenyl)pyrrolidin-1-yl)pyrazolo[1,5-a]pyrimidin-3-yl)-3-hydroxyazetidine-1-carboxamide To a solution of (R)—N-(5-(2-(2-chloro-5-fluorophenyl)pyrrolidin-1-yl)pyrazolo[1,5-a]pyrimidin-3-yl)-3-hy-

47 droxyazetidine-1-carboxamide (11.1 mg, 0.0258 mmol) in methanol (1 mL) at ambient temperature was added sulfuric acid in methanol (258 μL, 0.0258 mmol). The resulting solution was stirred for 30 minutes then concentrated to provide (R)—N-(5-(2-(2-chloro-5-fluorophenyl)pyrrolidin-1-yl)pyrazolo[1,5-a]pyrimidin-3-yl)-3-hydroxyazetidine-1-carboxamide sulfate (10 mg, 0.0189 mmol, 73.4% yield) as a yellow solid.

Example 9

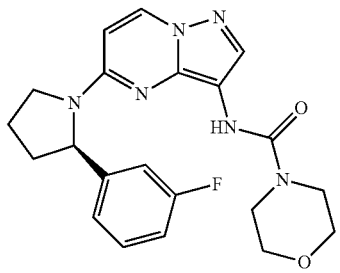 [SMILES: O=C(Nc1cnn2ccc(N3CCC[C@@H]3c3cccc(F)c3)nc12)N1CCOCC1]

(R)—N-(5-(2-(3-fluorophenyl)pyrrolidin-1-yl)pyrazolo[1,5-a]pyrimidin-3-yl)morpholine-4-carboxamide Step A: Preparation of (R)-5-(2-(3-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step A with (R)-2-(3-fluorophenyl)pyrrolidine.

Step B: Preparation of (R)—N-(5-(2-(3-fluorophenyl)pyrrolidin-1-yl)pyrazolo[1,5-a]pyrimidin-3-yl)morpholine-4-carboxamide: To a DCM (0.8 mL) solution of (R)-5-(2-(3-fluorophenyl)pyrrolidin-1-yl)pyrazolo[1,5-a]pyrimidin-3-amine (50 mg, 0.17 mmol) was added CDI (41 mg, 0.25 mmol) at ambient temperature in one portion. After stirring two hours, morpholine (22 mg, 0.25 mmol) was added in one portion. The reaction was stirred for 5 minutes before it was concentrated and directly purified by reverse-phase column chromatography, eluting with 5 to 54% acetonitrile/water to yield the final product as a yellowish foamy powder (69 mg, 100% yield). MS (apci) m/z=411.2 (M+H).

Example 10

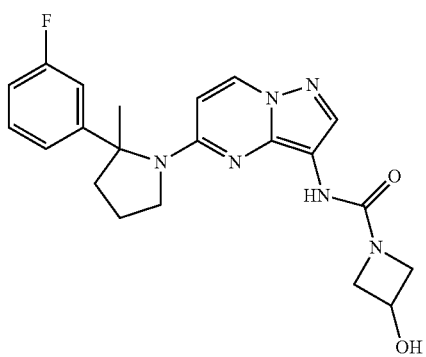 [SMILES: CC1(c2cccc(F)c2)CCCN1c1ccn2ncc(NC(=O)N3CC(O)C3)c2n1]

48

N-(5-(2-(3-fluorophenyl)-2-methylpyrrolidin-1-yl)pyrazolo[1,5-a]pyrimidin-3-yl)-3-hydroxyazetidine-1-carboxamide Step A: Preparation of tert-butyl 4-(3-fluorophenyl)-4-oxobutylcarbamate: In a round-bottomed flask was charged tert-butyl 2-oxopyrrolidine-1-carboxylate (2.2 g, 11.9 mmol) and THF (25 mL). The mixture was cooled down to −78° C. first, followed by slow addition of (3-fluorophenyl)magnesium bromide (17.8 mL, 17.8 mmol, 1.0 M solution in THF) over 15 minutes. The mixture was stirred for 3 hours, during which time the bath temperature rose from −78° C. to −10° C. The reaction was quenched by drop-wise addition of 1N HCl (2 mL) and warmed up to ambient temperature, followed by addition of EtOAc and water. After separating the organic layer, the aqueous layer was extracted with EtOAc three times. The combined organic layers was dried over $Na_2SO_4$ and concentrated to yield the product as a clear oil.

Step B: Preparation of 5-(3-fluorophenyl)-3,4-dihydro-2H-pyrrole: Crude tert-butyl 4-(3-fluorophenyl)-4-oxobutylcarbamate was dissolved in 10 mL $CH_2Cl_2$ first, followed by addition of 10 mL 4N HCl (dioxane). The reaction was stirred at ambient temperature for 4 hours and filtered, giving the HCl salt of the desired product as a white solid (~2 g). To obtain the free base product, EtOAc and saturated $NaHCO_3$ (aq.) solution were added to the HCl salt of the product. After separating the organic layer, the aqueous layer was extracted with EtOAc three times. The combined organic extracts was dried over $Na_2SO_4$ and concentrated to yield 5-(3-fluorophenyl)-3,4-dihydro-2H-pyrrole (1.46 g, 75%).

Step C: Preparation of 2-(3-fluorophenyl)-2-methylpyrrolidine: A solution of 5-(3-fluorophenyl)-3,4-dihydro-2H-pyrrole (6.1 g, 37.4 mmol) in 100 mL THF was cooled to −78° C., and boron trifluoride diethyl etherate (9.47 mL, 74.8 mmol) was added drop-wise over 5 minutes. The resulting cloudy reaction mixture was stirred at −78° C. for 40 minutes. MeLi (1.6 M in diethyl ether, 46.7 mL, 74.8 mmol) was added drop-wise over 10 minutes. The mixture was stirred at −78° C. for another 2 hours, then warmed up to ambient temperature overnight. For workup, water and EtOAc were added to the reaction mixture, and the aqueous layer was acidified with HCl solution. After separating and discarding the organic layer, the aqueous layer was basified with NaOH (6 N, aq.) to pH=12 and extracted twice with EtOAc. The combined organic extracts was dried over $Na_2SO_4$ and concentrated to get a mixture of the desired product (2-(3-fluorophenyl)-2-methylpyrrolidine) and starting material (4.3 g, 1.3:1 of the desired product:starting material, 37% yield). The crude product was used in the next step without any further purification.

Step D: Preparation of 5-(2-(3-fluorophenyl)-2-methylpyrrolidin-1-yl)pyrazolo[1,5-a]pyrimidin-3-amine: Prepared according to the method of Preparation B, substituting (R)-2-(2,5-difluorophenyl)pyrrolidine in Step 1 with 2-(3-fluorophenyl)-2-methylpyrrolidine.

Step E: Preparation of N-(5-(2-(3-fluorophenyl)-2-methylpyrrolidin-1-yl)pyrazolo[1,5-a]pyrimidin-3-yl)-3-hydroxyazetidine-1-carboxamide: To a DCM (0.7 mL) solution of 5-(2-(3-fluorophenyl)-2-methylpyrrolidin-1-yl)pyrazolo[1,5-a]pyrimidin-3-amine (25 mg, 0.08 mmol) was added CDI (20 mg, 0.12 mmol) at ambient temperature in one portion. After stirring one hour, azetidin-3-ol hydrochloride (20 mg, 0.12 mmol) was added in one portion, followed by addition of DIEA (0.028 mL, 0.16 mmol). The reaction was stirred for 30 minutes before it was concentrated and directly purified by reverse-phase column chromatography, eluting with 0 to 60% acetonitrile/water to yield the final product as a yellowish oil (18 mg, 55% yield). MS (apci) m/z=411.2 (M+H).

Example 11

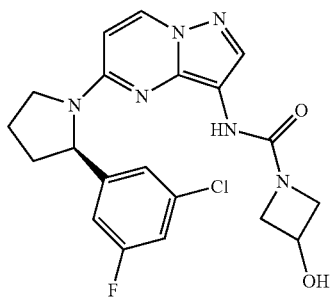 [SMILES: O=C(Nc1cnn2ccc(N3CCC[C@@H]3c3cc(F)cc(Cl)c3)nc12)N1CC(O)C1]

(R)—N-(5-(2-(3-chloro-5-fluorophenyl)pyrrolidin-1-yl)pyrazolo[1,5-a]pyrimidin-3-yl)-3-hydroxyazetidine-1-carboxamide Step A: Preparation of (R)-5-(2-(3-chloro-5-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step A with (R)-2-(3-chloro-5-fluorophenyl)pyrrolidine.

Step B: Preparation of (R)-2-(3-chloro-5-fluorophenyl)pyrrolidine: Prepared by the method of Preparation A, substituting 2-bromo-1,4-difluorobenzene with 1-bromo-3-chloro-5-fluorobenzene in step A.

Step C: Preparation of (R)—N-(5-(2-(3-chloro-5-fluorophenyl)pyrrolidin-1-yl)pyrazolo[1,5-a]pyrimidin-3-yl)-3-hydroxyazetidine-1-carboxamide: To a DCM (0.7 mL) solution of (R)-5-(2-(3-chloro-5-fluorophenyl)pyrrolidin-1-yl)pyrazolo[1,5-a]pyrimidin-3-amine (20 mg, 0.06 mmol, prepared as described in the following paragraph), was added CDI (20 mg, 0.12 mmol) at ambient temperature in one portion. After stirring two hours, azetidin-3-ol hydrochloride (20 mg, 0.18 mmol) was added in one portion, followed by addition of DIEA (0.032 mL, 0.18 mmol). The reaction was stirred overnight before it was concentrated and directly purified by reverse-phase column chromatography, eluting with 0 to 60% acetonitrile/water to yield the final product as a solid (29 mg, 74% yield). MS (apci) m/z=431.2 (M+H).

Example 12

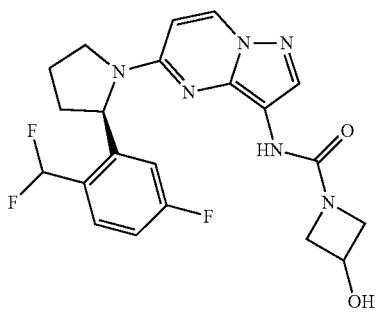 [SMILES: O=C(Nc1cnn2ccc(N3CCC[C@@H]3c3cc(F)ccc3C(F)F)nc12)N1CC(O)C1]

(R)—N-(5-(2-(2-(difluoromethyl)-5-fluorophenyl)pyrrolidin-1-yl)pyrazolo[1,5-a]pyrimidin-3-yl)-3-hydroxyazetidine-1-carboxamide Step A: Preparation of (R)-5-(2-(2-(difluoromethyl)-5-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step A with (R)-2-(2-(difluoromethyl)-5-fluorophenyl)pyrrolidine.

Step B: Preparation of (R)-2-(3-chloro-5-fluorophenyl)pyrrolidine: Prepared by the method of Preparation A, substituting 2-bromo-1,4-difluorobenzene with 2-bromo-1-(difluoromethyl)-4-fluorobenzene in step A.

Step C: Preparation of (R)—N-(5-(2-(2-(difluoromethyl)-5-fluorophenyl)pyrrolidin-1-yl)pyrazolo[1,5-a]pyrimidin-3-yl)-3-hydroxyazetidine-1-carboxamide: To a DCM (0.6 mL) solution of (R)-5-(2-(2-(difluoromethyl)-5-fluorophenyl)pyrrolidin-1-yl)pyrazolo[1,5-a]pyrimidin-3-amine (10 mg, 0.028 mmol, prepared as described in the following paragraph), was added CDI (9 mg, 0.056 mmol) at ambient temperature in one portion. After stirring two hours, azetidin-3-ol hydrochloride (6 mg, 0.056 mmol) was added in one portion, followed by addition of DIEA (0.015 mL, 0.084 mmol). The reaction was stirred overnight before it was concentrated and directly purified by reverse-phase column chromatography, eluting with 0 to 50% acetonitrile/water to yield the final product as a solid. MS (apci) m/z=447.2 (M+H).

Example 13

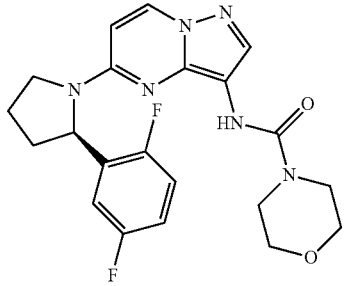 [SMILES: O=C(Nc1cnn2ccc(N3CCC[C@@H]3c3cc(F)ccc3F)nc12)N1CCOCC1]

(R)—N-(5-(2-(2,5-difluorophenyl)pyrrolidin-1-yl)pyrazolo[1,5-a]pyrimidin-3-yl)morpholine-4-carboxamide To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, morpholine (17 mg, 0.19 mmol) was added in one portion. The reaction was stirred for 5 minutes before it was concentrated and directly purified by reverse-phase column chromatography, eluting with 5 to 55% acetonitrile/water to yield the final product as a yellowish foamy powder (37 mg, 91% yield). MS (apci) m/z=429.2 (M+H).

Example 14

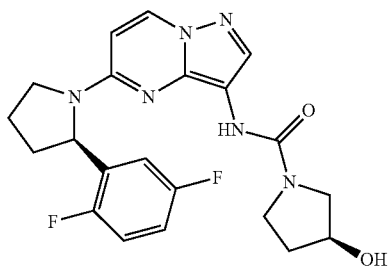 [SMILES: O=C(Nc1cnn2ccc(N3CCC[C@@H]3c3cc(F)ccc3F)nc12)N1CC[C@H](O)C1]

(S)—N-(5-((R)-2-(2,5-difluorophenyl)pyrrolidin-1-yl)pyrazolo[1,5-a]pyrimidin-3-yl)-3-hydroxypyrrolidine-1-carboxamide To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, (S)-pyrrolidin-3-ol (17 mg, 0.19 mmol) [purchased from Suven Life Sciences] was added in one portion. The reaction was stirred for 5 minutes before it was concentrated and directly purified by reverse-phase column chromatography, eluting with 0 to 50% acetonitrile/water to yield the final product as a yellowish foamy powder (30 mg, 74% yield). MS (apci) m/z=429.2 (M+H).

Example 14A

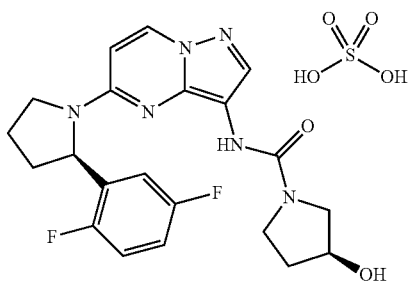

(S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate To a solution of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (4.5 mg, 0.011 mmol) in methanol (1 mL) at ambient temperature was added sulfuric acid in MeOH (105 μL, 0.011 mmol). The resulting solution was stirred for 30 minutes then concentrated to provide (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (5.2 mg, 0.0099 mmol, 94% yield) as a yellow solid.

Example 15

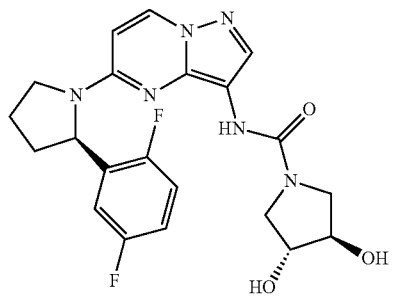 [SMILES: O=C(Nc1cnn2ccc(N3CCC[C@@H]3c3cc(F)ccc3F)nc12)N1C[C@@H](O)[C@H](O)C1]

(3R,4R)—N-(5-((R)-2-(2,5-difluorophenyl)pyrrolidin-1-yl)pyrazolo[1,5-a]pyrimidin-3-yl)-3,4-dihydroxypyrrolidine-1-carboxamide To a DCM (0.8 mL) solution of (R)-5-(2-(2,5-difluorophenyl)pyrrolidin-1-yl)pyrazolo[1,5-a]pyrimidin-3-amine (Preparation B; 26 mg, 0.08 mmol) was added CDI (27 mg, 0.16 mmol) at ambient temperature in one portion. After stirring two hours, (3R,4R)-pyrrolidine-3,4-diol (17.3 mg, 0.16 mmol) [obtained from benzyl de-protection of commercially available (3R,4R)-1-benzylpyrrolidine-3,4-diol] was added in one portion. A few drops of DMSO were added to obtain a clear reaction solution. The reaction was stirred for 5 minutes before it was concentrated and directly purified by reverse-phase column chromatography, eluting with 0 to 45% acetonitrile/water to yield the final product as a yellowish foamy powder (27 mg, 74% yield). MS (apci) m/z=445.2 (M+H).

Example 16

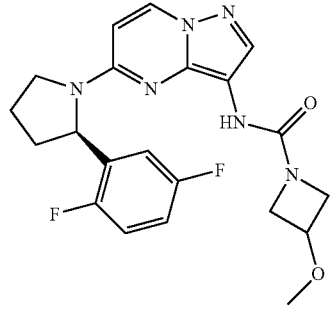 [SMILES: COC1CN(C(=O)Nc2cnn3ccc(N4CCC[C@@H]4c4cc(F)ccc4F)nc23)C1]

(R)—N-(5-(2-(2,5-difluorophenyl)pyrrolidin-1-yl)pyrazolo[1,5-a]pyrimidin-3-yl)-3-methoxyazetidine-1-carboxamide To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, 3-methoxyazetidine 2,2,2-trifluoroacetate (38 mg, 0.19 mmol) [obtained from N-de-protection of commercially available tert-butyl 3-methoxyazetidine-1-carboxylate using TFA in DCM] was added in one portion, followed by addition of DIEA (0.050 mL, 0.29 mmol). The reaction was stirred for 5 minutes before it was concentrated and directly purified by reverse-phase column chromatography, eluting with 0 to 55% acetonitrile/water to yield the final product as a yellowish foamy powder (34 mg, 83% yield). MS (apci) m/z=429.2 (M+H).

Example 16A

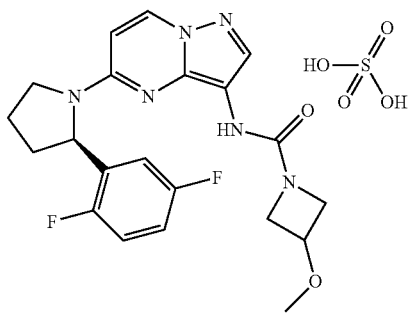

(R)—N-(5-(2-(2,5-difluorophenyl)pyrrolidin-1-yl) pyrazolo[1,5-a]pyrimidin-3-yl)-3-methoxyazetidine-1-carboxamide sulfate To a solution of (R)—N-(5-(2-(2,5-difluorophenyl)pyrrolidin-1-yl)pyrazolo[1,5-a]pyrimidin-3-yl)-3-methoxyazetidine-1-carboxamide (6.2 mg, 0.014 mmol) in methanol (1 mL) at ambient temperature was added sulfuric acid in methanol (145 μL, 0.014 mmol). The resulting solution was stirred for 30 minutes then concentrated to provide (R)—N-(5-(2-(2,5-difluorophenyl)pyrrolidin-1-yl)pyrazolo[1,5-a]pyrimidin-3-yl)-3-methoxyazetidine-1-carboxamide sulfate (7.2 mg, 0.014 mmol, 94% yield) as a yellow solid.

Example 17

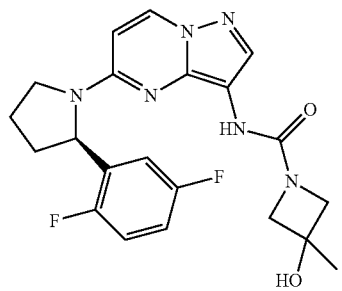 [SMILES: CC1(O)CN(C(=O)Nc2cnn3ccc(N4CCC[C@@H]4c4cc(F)ccc4F)nc23)C1]

(R)—N-(5-(2-(2,5-difluorophenyl)pyrrolidin-1-yl) pyrazolo[1,5-a]pyrimidin-3-yl)-3-hydroxy-3-methylazetidine-1-carboxamide To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, 3-methoxyazetidine 3-methylazetidin-3-ol hydrochloride (26 mg, 0.19 mmol) [obtained from N-deprotection of commercially available 1-benzhydryl-3-methylazetidin-3-ol under hydrogenation conditions facilitated by Pd(OH)$_2$ in EtOH and 1% TFA] was added in one portion, followed by addition of DIEA (0.050 mL, 0.29 mmol). The reaction was stirred for 5 minutes before it was concentrated and directly purified by reverse-phase column chromatography, eluting with 0 to 50% acetonitrile/water to yield the final product as a yellowish foamy powder (27 mg, 66% yield). MS (apci) m/z=429.2 (M+H).

Example 17A

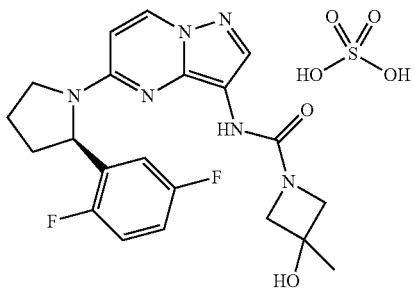

(R)—N-(5-(2-(2,5-difluorophenyl)pyrrolidin-1-yl) pyrazolo[1,5-a]pyrimidin-3-yl)-3-hydroxy-3-methylazetidine-1-carboxamide sulfate To a solution of (R)—N-(5-(2-(2,5-difluorophenyl)pyrrolidin-1-yl)pyrazolo[1,5-a]pyrimidin-3-yl)-3-hydroxy-3-methylazetidine-1-carboxamide (3.1 mg, 0.0072 mmol) in methanol (1 mL) at ambient temperature was added sulfuric acid in methanol (145 μL, 0.014 mmol). The resulting solution was stirred for 30 minutes then concentrated to provide (R)—N-(5-(2-(2,5-difluorophenyl)pyrrolidin-1-yl)pyrazolo[1,5-a]pyrimidin-3-yl)-3-hydroxy-3-methylazetidine-1-carboxamide sulfate (3.3 mg, 0.0063 mmol, 87% yield) as a yellow solid.

Example 17B

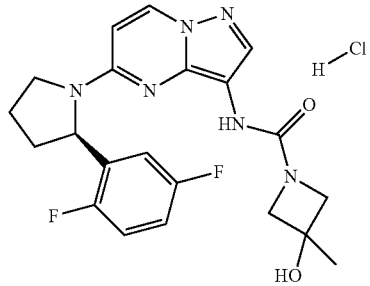

(R)—N-(5-(2-(2,5-difluorophenyl)pyrrolidin-1-yl) pyrazolo[1,5-a]pyrimidin-3-yl)-3-hydroxy-3-methylazetidine-1-carboxamide hydrochloride To a methanol (1 mL) solution of (R)—N-(5-(2-(2,5-difluorophenyl)pyrrolidin-1-yl)pyrazolo[1,5-a]pyrimidin-3-yl)-3-hydroxy-3-methylazetidine-1-carboxamide (10.2 mg, 0.0238 mmol) was added HCl as a solution is dioxane (30 μL). After 30 minutes, the reaction was concentrated to provide (R)—N-(5-(2-(2,5-difluorophenyl)pyrrolidin-1-yl)

pyrazolo[1,5-a]pyrimidin-3-yl)-3-hydroxy-3-methylazetidine-1-carboxamide hydrochloride (8.3 mg, 0.0179 mmol, 75.0% yield) as a yellow solid.

Example 18

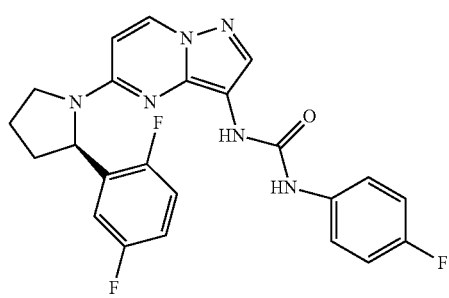 [SMILES: O=C(Nc1ccc(F)cc1)Nc1cnn2ccc(N3CCC[C@@H]3c3cc(F)ccc3F)nc12]

(R)-1-(5-(2-(2,5-difluorophenyl)pyrrolidin-1-yl)pyrazolo[1,5-a]pyrimidin-3-yl)-3-(4-fluorophenyl)urea To a DCM (0.8 mL) solution of (R)-5-(2-(2,5-difluorophenyl)pyrrolidin-1-yl)pyrazolo[1,5-a]pyrimidin-3-amine (Preparation B; 25 mg, 0.079 mmol) was added 1-fluoro-4-isocyanatobenzene (13 mg, 0.095 mmol) at ambient temperature drop-wise, followed by addition of DIEA (0.028 mL, 0.16 mmol). The reaction was stirred for 90 minutes before it was concentrated and directly purified by column chromatography on silica, eluting with 3:1 EtOAc/hexanes to yield the final product as a solid (30 mg, 84% yield). MS (apci) m/z=453.2 (M+H).

Example 19

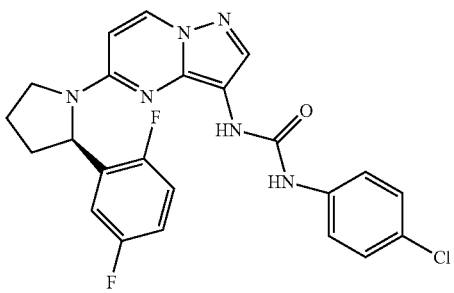 [SMILES: O=C(Nc1ccc(Cl)cc1)Nc1cnn2ccc(N3CCC[C@@H]3c3cc(F)ccc3F)nc12]

(R)-1-(4-chlorophenyl)-3-(5-(2-(2,5-difluorophenyl)pyrrolidin-1-yl)pyrazolo[1,5-a]pyrimidin-3-yl)urea Prepared by the method as described in Example 18, substituting 1-fluoro-4-isocyanatobenzene with 1-chloro-4-isocyanatobenzene, giving the final product as a fine white solid (33 mg, 89%). MS (apci) m/z=469.1 (M+H).

Example 20

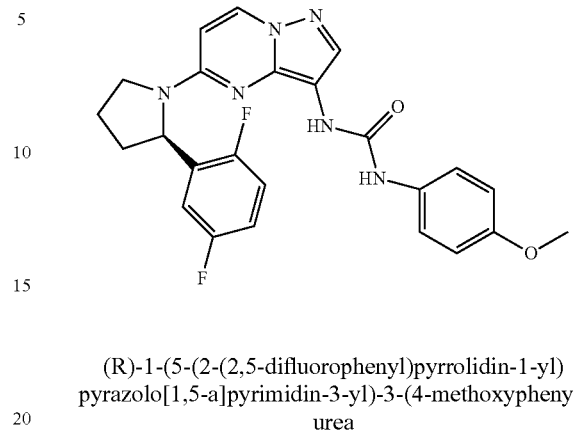

(R)-1-(5-(2-(2,5-difluorophenyl)pyrrolidin-1-yl)pyrazolo[1,5-a]pyrimidin-3-yl)-3-(4-methoxyphenyl)urea Prepared by the method as described in Example 18, substituting 1-fluoro-4-isocyanatobenzene with 1-methoxy-4-isocyanatobenzene, and eluting with first 4:1 EtOAc/hexanes and then 100% EtOAc during silica column chromatography purification step, giving the final product as a fine white solid (34 mg, 92%). MS (apci) m/z=465.2 (M+H).

Example 21

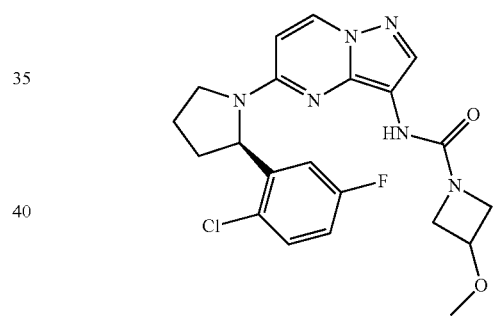

(R)—N-(5-(2-(2-chloro-5-fluorophenyl)pyrrolidin-1-yl)pyrazolo[1,5-a]pyrimidin-3-yl)-3-methoxyazetidine-1-carboxamide Step A: Preparation of (R)-5-(2-(2-chloro-5-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step A with (R)-2-(2-chloro-5-fluorophenyl)pyrrolidine.

Step B: Preparation of (R)—N-(5-(2-(2-chloro-5-fluorophenyl)pyrrolidin-1-yl)pyrazolo[1,5-a]pyrimidin-3-yl)-3-methoxyazetidine-1-carboxamide: To a DCM (0.8 mL) solution of (R)-5-(2-(2-chloro-5-fluorophenyl)pyrrolidin-1-yl)pyrazolo[1,5-a]pyrimidin-3-amine (30 mg, 0.090 mmol) was added CDI (29 mg, 0.18 mmol) at ambient temperature in one portion. After stirring for two hours, 3-methoxyazetidine 2,2,2-trifluoroacetate (36 mg, 0.18 mmol) [obtained from N-deprotection of commercially available tert-butyl 3-methoxyazetidine-1-carboxylate using TFA in DCM] was added in one portion, followed by addition of DIEA (0.047 mL, 0.27 mmol). The reaction was stirred for 5 minutes before it Example 22

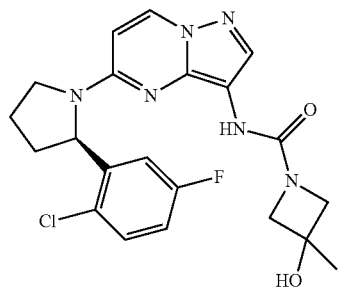 [SMILES: CC1(O)CN(C(=O)Nc2cnn3ccc(N4CCC[C@@H]4c4cc(F)ccc4Cl)nc23)C1]

(R)—N-(5-(2-(2-chloro-5-fluorophenyl)pyrrolidin-1-yl)pyrazolo[1,5-a]pyrimidin-3-yl)-3-hydroxy-3-methylazetidine-1-carboxamide To a DCM (0.8 mL) solution of (R)-5-(2-(2-chloro-5-fluorophenyl)pyrrolidin-1-yl)pyrazolo[1,5-a]pyrimidin-3-amine (Example 8, Step A; 22 mg, 0.066 mmol) was added CDI (22 mg, 0.13 mmol) at ambient temperature in one portion. After stirring two hours, 3-methoxyazetidine 3-methylazetidin-3-ol hydrochloride (18 mg, 0.13 mmol) was added in one portion, followed by addition of DIEA (0.035 mL, 0.20 mmol). The reaction was stirred for 5 minutes before it was concentrated and directly purified by reverse-phase column chromatography, eluting with 5 to 50% acetonitrile/water to yield the final product as a yellowish foamy powder (21 mg, 71% yield). MS (apci) m/z=445.2 (M+H).

Example 23

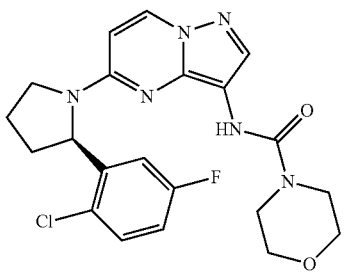 [SMILES: O=C(Nc1cnn2ccc(N3CCC[C@@H]3c3cc(F)ccc3Cl)nc12)N1CCOCC1]

(R)—N-(5-(2-(2-chloro-5-fluorophenyl)pyrrolidin-1-yl)pyrazolo[1,5-a]pyrimidin-3-yl)morpholine-4-carboxamide Prepared according to the method of Example 22, replacing (R)-5-(2-(2-chloro-5-fluorophenyl)pyrrolidin-1-yl)pyrazolo[1,5-a]pyrimidin-3-amine with morpholine to yield the product as a yellowish foamy powder (26 mg, 76% yield). MS (apci) m/z=445.1 (M+H).

Example 24

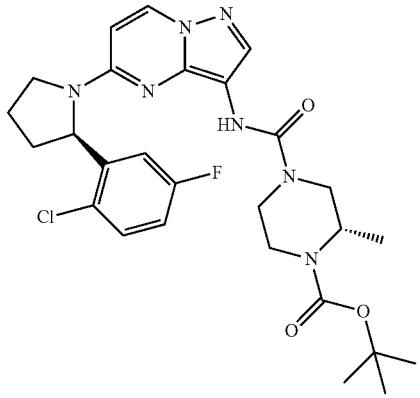 [SMILES: C[C@H]1CN(C(=O)Nc2cnn3ccc(N4CCC[C@@H]4c4cc(F)ccc4Cl)nc23)CCN1C(=O)OC(C)(C)C]

(S)-tert-butyl 4-(5-((R)-2-(2-chloro-5-fluorophenyl)pyrrolidin-1-yl)pyrazolo[1,5-a]pyrimidin-3-ylcarbamoyl)-2-methylpiperazine-1-carboxylate Prepared according to the method of Example 22, replacing (R)-5-(2-(2-chloro-5-fluorophenyl)pyrrolidin-1-yl)pyrazolo[1,5-a]pyrimidin-3-amine with (S)-tert-butyl 2-methylpiperazine-1-carboxylate to yield the product as a yellowish foamy powder (47 mg, 80% yield). MS (apci) m/z=558.1 (M+H).

Example 25

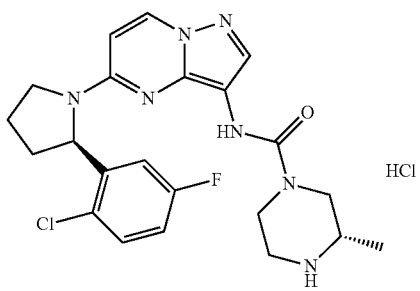 [SMILES: C[C@H]1CN(C(=O)Nc2cnn3ccc(N4CCC[C@@H]4c4cc(F)ccc4Cl)nc23)CCN1 ; Cl]

(S)—N-(5-((R)-2-(2-chloro-5-fluorophenyl)pyrrolidin-1-yl)pyrazolo[1,5-a]pyrimidin-3-yl)-3-methylpiperazine-1-carboxamide hydrochloride To (S)-tert-butyl 4-(5-((R)-2-(2-chloro-5-fluorophenyl)pyrrolidin-1-yl)pyrazolo[1,5-a]pyrimidin-3-ylcarbamoyl)-2-methylpiperazine-1-carboxylate (Example 24; 47 mg, 0.084 mmol), was added 1 mL 4 N HCl (dioxane) solution and stirred at ambient temperature for 10 minutes. The reaction was concentrated, treated with ether, and filtered, giving the final product HCl salt as a fine beige powder. MS (apci) m/z=458.1 (M+H).

Example 26

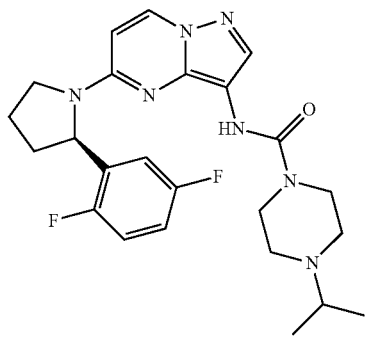 [SMILES: CC(C)N1CCN(C(=O)Nc2cnn3ccc(N4CCC[C@@H]4c4cc(F)ccc4F)nc23)CC1]

(R)-N-(5-(2-(2,5-difluorophenyl)pyrrolidin-1-yl)pyrazolo[1,5-a]pyrimidin-3-yl)-4-isopropylpiperazine-1-carboxamide To a DCM (0.8 mL) solution of (R)-5-(2-(2,5-difluorophenyl)pyrrolidin-1-yl)pyrazolo[1,5-a]pyrimidin-3-amine (Preparation B; 30 mg, 0.095 mmol) was added CDI (31 mg, 0.19 mmol) at ambient temperature in one portion. After stirring two hours, 1-isopropylpiperazine (24 mg, 0.19 mmol) was added in one portion. The reaction was stirred for 5 minutes before it was concentrated and directly purified by reverse-phase column chromatography, eluting with 5 to 45% acetonitrile/water to yield the final product as a yellowish foamy powder (40 mg, 90% yield). MS (apci) m/z=470.1 (M+H).

Example 27

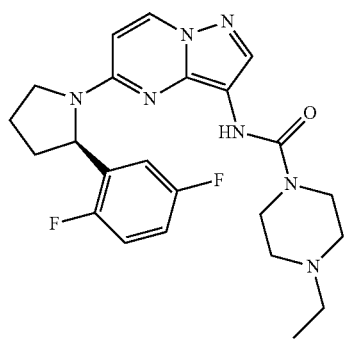 [SMILES: CCN1CCN(C(=O)Nc2cnn3ccc(N4CCC[C@@H]4c4cc(F)ccc4F)nc23)CC1]

(R)-N-(5-(2-(2,5-difluorophenyl)pyrrolidin-1-yl)pyrazolo[1,5-a]pyrimidin-3-yl)-4-ethylpiperazine-1-carboxamide Prepared by the method as described in Example 26, substituting 1-isopropylpiperazine with 1-ethylpiperazine, giving the final product as a yellowish solid (40 mg, 92%). MS (apci) m/z=456.1 (M+H).

Example 28

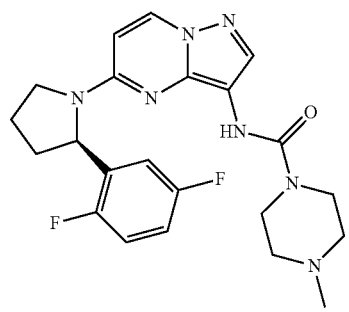 [SMILES: CN1CCN(C(=O)Nc2cnn3ccc(N4CCC[C@@H]4c4cc(F)ccc4F)nc23)CC1]

(R)-N-(5-(2-(2,5-difluorophenyl)pyrrolidin-1-yl)pyrazolo[1,5-a]pyrimidin-3-yl)-4-methylpiperazine-1-carboxamide Prepared by the method as described in Example 26, substituting 1-isopropylpiperazine with 1-methylpiperazine, giving the final product as a yellowish solid (38 mg, 90%). MS (apci) m/z=442.2 (M+H).

Example 28A

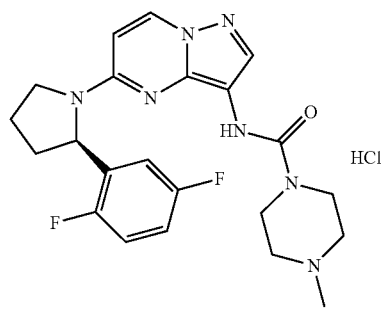 [SMILES: CN1CCN(C(=O)Nc2cnn3ccc(N4CCC[C@@H]4c4cc(F)ccc4F)nc23)CC1 ; Cl]

(R)-N-(5-(2-(2,5-difluorophenyl)pyrrolidin-1-yl)pyrazolo[1,5-a]pyrimidin-3-yl)-4-methylpiperazine-1-carboxamide hydrochloride To a methanol (1 mL) solution of (R)-N-(5-(2-(2,5-difluorophenyl)pyrrolidin-1-yl)pyrazolo[1,5-a]pyrimidin-3-yl)-4-methylpiperazine-1-carboxamide was added HCl as a solution is dioxane (30 µL). After 30 minutes, the reaction was concentrated to provide (R)-N-(5-(2-(2,5-difluorophenyl)pyrrolidin-1-yl)pyrazolo[1,5-a]pyrimidin-3-yl)-4-methylpiperazine-1-carboxamide hydrochloride as a yellow solid.

Example 29

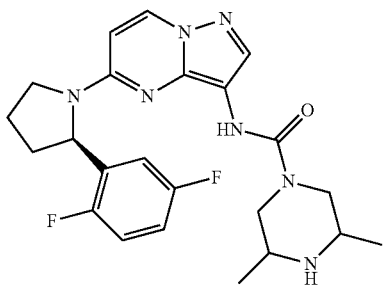 [SMILES: CC1CN(C(=O)Nc2cnn3ccc(N4CCC[C@@H]4c4cc(F)ccc4F)nc23)CC(C)N1]

N-(5-((R)-2-(2,5-difluorophenyl)pyrrolidin-1-yl)pyrazolo[1,5-a]pyrimidin-3-yl)-3,5-dimethylpiperazine-1-carboxamide Prepared by the method as described in Example 26, substituting 1-isopropylpiperazine with 2,6-dimethylpiperazine [predominantly cis, Aldrich], giving the final product as a yellowish solid (34 mg, 78%). MS (apci) m/z=456.2 (M+H).

Example 30

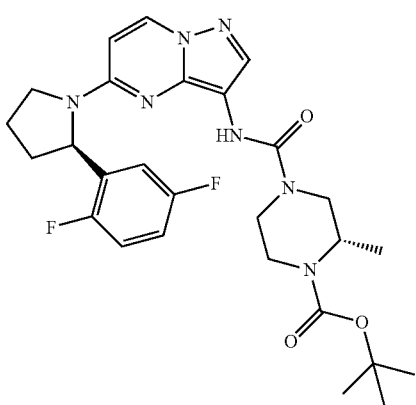 [SMILES: C[C@H]1CN(C(=O)Nc2cnn3ccc(N4CCC[C@@H]4c4cc(F)ccc4F)nc23)CCN1C(=O)OC(C)(C)C]

(S)-tert-butyl 4-(5-((R)-2-(2,5-difluorophenyl)pyrrolidin-1-yl)pyrazolo[1,5-a]pyrimidin-3-ylcarbamoyl)-2-methylpiperazine-1-carboxylate Prepared by the method as described in Example 26, substituting 1-isopropylpiperazine with (S)-tert-butyl 2-methylpiperazine-1-carboxylate, giving the final product as a yellowish solid (47 mg, 90%). MS (apci) m/z=542.2 (M+H).

Example 31

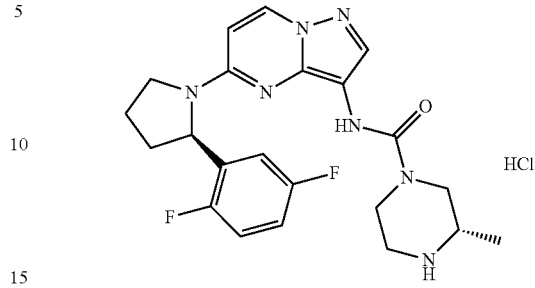

(S)—N-(5-((R)-2-(2,5-difluorophenyl)pyrrolidin-1-yl)pyrazolo[1,5-a]pyrimidin-3-yl)-3-methylpiperazine-1-carboxamide hydrochloride To (S)-tert-butyl 4-(5-((R)-2-(2,5-difluorophenyl)pyrrolidin-1-yl)pyrazolo[1,5-a]pyrimidin-3-ylcarbamoyl)-2-methylpiperazine-1-carboxylate (Example 30; 47 mg, 0.087 mmol), was added 1 mL 4 N HCl (dioxane) solution and stirred at ambient temperature for 1 hour. The reaction was concentrated, treated with ether, and filtered, giving the final product HCl salt as a fine yellowish powder. MS (apci) m/z=442.2 (M+H).

Example 32

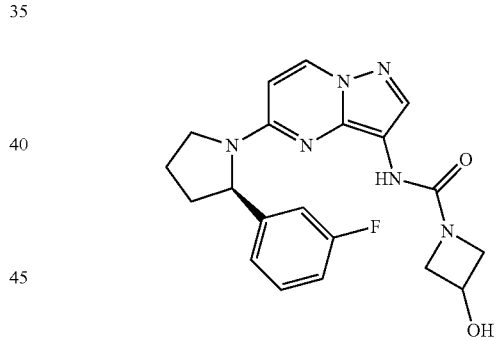

(R)—N-(5-(2-(3-fluorophenyl)pyrrolidin-1-yl)pyrazolo[1,5-a]pyrimidin-3-yl)-3-hydroxyazetidine-1-carboxamide To a DCM (0.8 mL) solution of (R)-5-(2-(3-fluorophenyl)pyrrolidin-1-yl)pyrazolo[1,5-a]pyrimidin-3-amine (Example 6, Step A; 50 mg, 0.17 mmol) was added CDI (41 mg, 0.25 mmol) at ambient temperature in one portion. After stirring two hours, azetidin-3-ol hydrochloride (28 mg, 0.25 mmol) was added in one portion, followed by addition of DIEA (0.059 mL, 0.34 mmol). The reaction was stirred for 5 minutes before it was concentrated and directly purified by reverse-phase column chromatography, eluting with 5 to 55% acetonitrile/water to yield the final product as a yellowish foamy powder (64 mg, 96% yield). MS (apci) m/z=397.2 (M+H).

Example 33

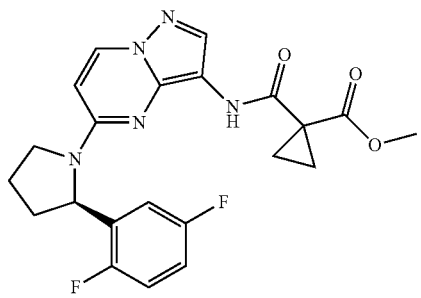 [SMILES: COC(=O)C1(C(=O)Nc2cnn3ccc(N4CCC[C@@H]4c4cc(F)ccc4F)nc23)CC1]

(R)-methyl 1-(5-(2-(2,5-difluorophenyl)pyrrolidin-1-yl)pyrazolo[1,5-a]pyrimidin-3-ylcarbamoyl)cyclopropanecarboxylate To a mixture of (R)-5-(2-(2,5-difluorophenyl)pyrrolidin-1-yl)pyrazolo[1,5-a]pyrimidin-3-amine (Preparation B; 43 mg, 0.14 mmol), 1-(methoxycarbonyl)cyclopropanecarboxylic acid (24 mg, 0.16 mmol), and HATU (62 mg, 0.16 mmol) was added 0.7 mL DMF to make a solution. After cooling in an ice bath for 10 minutes, DIEA (0.053 mL, 0.30 mmol) was added to the reaction drop-wise. The reaction was allowed to warm up to ambient temperature and stirred for 10 minutes. The reaction mixture was diluted with EtOAc (15 mL), washed with water, brine (5 mL each), concentrated, and purified by reverse-phase column chromatography, eluting with 5 to 72% acetonitrile/water to yield the final product as a yellowish foamy powder (36 mg, 60% yield). MS (apci) m/z=442.2 (M+H).

Example 34

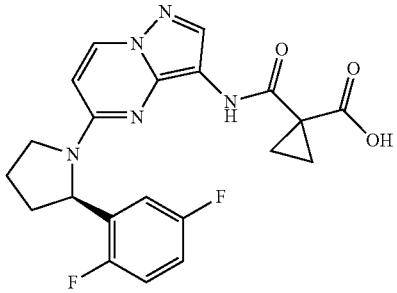 [SMILES: O=C(O)C1(C(=O)Nc2cnn3ccc(N4CCC[C@@H]4c4cc(F)ccc4F)nc23)CC1]

(R)-1-(5-(2-(2,5-difluorophenyl)pyrrolidin-1-yl)pyrazolo[1,5-a]pyrimidin-3-ylcarbamoyl)cyclopropanecarboxylic acid (R)-methyl 1-(5-(2-(2,5-difluorophenyl)pyrrolidin-1-yl)pyrazolo[1,5-a]pyrimidin-3-ylcarbamoyl)cyclopropanecarboxylate (Example 33; 24 mg, 0.054 mmol), was dissolved in a mixture solvent of THF/MeOH/water (0.3/0.3/0.2 mL), followed by addition of lithium hydroxide monohydrate (6 mg, 0.14 mmol). After stirring at ambient temperature for five hours, the reaction mixture was diluted with water (15 mL), acidified with 1N HCl (aq.) to pH ~3, and filtered, giving the final product as a fine white solid (19 mg, 82% yield). MS (apci) m/z=428.2 (M+H).

Example 35

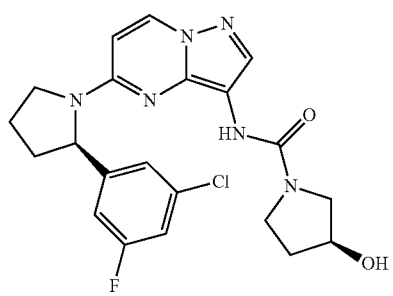 [SMILES: O=C(Nc1cnn2ccc(N3CCC[C@@H]3c3cc(F)cc(Cl)c3)nc12)N1CC[C@H](O)C1]

(S)—N-(5-((R)-2-(3-chloro-5-fluorophenyl)pyrrolidin-1-yl)pyrazolo[1,5-a]pyrimidin-3-yl)-3-hydroxypyrrolidine-1-carboxamide To a DCM (0.6 mL) solution of (R)-5-(2-(3-chloro-5-fluorophenyl)pyrrolidin-1-yl)pyrazolo[1,5-a]pyrimidin-3-amine (Example 11, Step A; 20 mg, 0.06 mmol), was added CDI (20 mg, 0.12 mmol) at ambient temperature in one portion. After stirring two hours, (S)-pyrrolidin-3-ol (16 mg, 0.18 mmol) was added in one portion. The reaction was stirred overnight before it was concentrated and directly purified by reverse-phase column chromatography, eluting with 0 to 60% acetonitrile/water to yield the final product as a solid (50 mg, 83% yield). MS (apci) m/z=445.2 (M+H).

Example 36

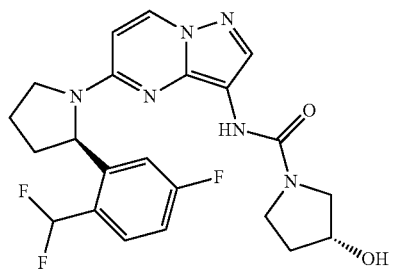 [SMILES: O=C(Nc1cnn2ccc(N3CCC[C@@H]3c3cc(F)ccc3C(F)F)nc12)N1CC[C@@H](O)C1]

(R)—N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide Step A: Preparation of (R)-5-(2-(2-(difluoromethyl)-5-fluorophenyl)pyrrolidin-1-yl)pyrazolo[1,5-a]pyrimidin-3-amine: Prepared according to the method of Preparation B, substituting (R)-2-(2,5-difluorophenyl)pyrrolidine in Step 1 with (R)-2-(2-(difluoromethyl)-5-fluorophenyl)pyrrolidine.

Step B: Preparation of (R)—N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide: To a DCM (0.6 mL) solution of (R)-5-(2-(2-(difluoromethyl)-5-fluorophenyl)pyrrolidin-1-yl)pyrazolo[1,5-a]pyrimidin-3-amine (10 mg, 0.028 mmol, prepared as described in the following paragraph), was added CDI (9 mg, 0.056 mmol) at ambient temperature in one portion. After stirring two hours, (S)-pyrrolidin-3-ol (8 mg, 0.084 mmol) was added in one portion. The reaction was stirred overnight, then concentrated and directly purified by reverse-phase column chromatography, eluting with 0 to 50% acetonitrile/water to yield the final product as a solid (9 mg, 69%). MS (apci) m/z=461.2 (M+H).

Example 37

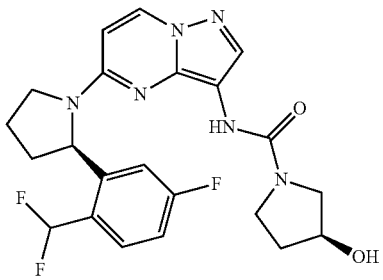 [SMILES: O=C(Nc1cnn2ccc(N3CCC[C@@H]3c3cc(F)ccc3C(F)F)nc12)N1CC[C@H](O)C1]

(S)—N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide Prepared by the method as described in Example 36, substituting (S)-pyrrolidin-3-ol with (R)-pyrrolidin-3-ol, giving the final product as a solid (12 mg, 89%). MS (apci) m/z=461.2 (M+H).

Example 38

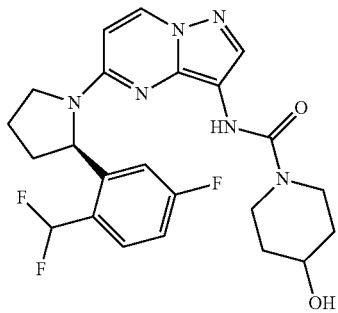 [SMILES: O=C(Nc1cnn2ccc(N3CCC[C@@H]3c3cc(F)ccc3C(F)F)nc12)N1CCC(O)CC1]

(R)—N-(5-(2-(2-(difluoromethyl)-5-fluorophenyl)pyrrolidin-1-yl)pyrazolo[1,5-a]pyrimidin-3-yl)-4-hydroxypiperidine-1-carboxamide Prepared by the method as described in Example 36, substituting (S)-pyrrolidin-3-ol with piperidin-4-ol, giving the final product as a solid (11 mg, 80%). MS (apci) m/z=475.2 (M+H).

Example 39

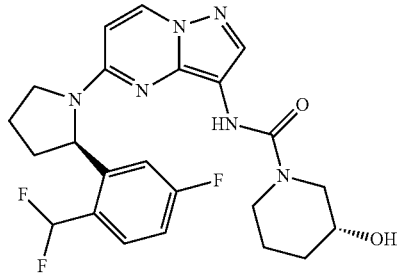 [SMILES: O=C(Nc1cnn2ccc(N3CCC[C@@H]3c3cc(F)ccc3C(F)F)nc12)N1CCC[C@@H](O)C1]

(R)—N-(5-(R)-2-(2-(difluoromethyl)-5-fluorophenyl)pyrrolidin-1-yl)pyrazolo[1,5-a]pyrimidin-3-yl)-3-hydroxypiperidine-1-carboxamide Prepared by the method as described in Example 36, substituting (S)-pyrrolidin-3-ol with (R)-piperidin-3-ol hydrochloride (followed by addition of 3 equivalents of DIEA), giving the final product as a solid (10 mg, 74%). MS (apci) m/z=475.2 (M+H).

Example 40

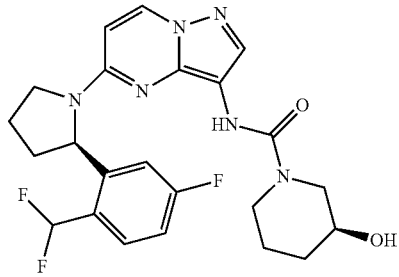 [SMILES: O=C(Nc1cnn2ccc(N3CCC[C@@H]3c3cc(F)ccc3C(F)F)nc12)N1CCC[C@H](O)C1]

(S)—N-(5-((R)-2-(2-(difluoromethyl)-5-fluorophenyl)pyrrolidin-1-yl)pyrazolo[1,5-a]pyrimidin-3-yl)-3-hydroxypiperidine-1-carboxamide Prepared by the method as described in Example 36, substituting (S)-pyrrolidin-3-ol with (S)-piperidin-3-ol hydrochloride (followed by addition of 3 equivalents of DIEA), giving the final product as a solid (11 mg, 80%). MS (apci) m/z=475.2 (M+H).

Example 41

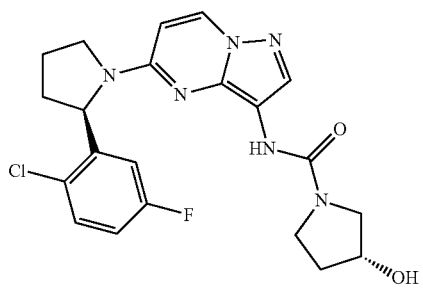 [SMILES: O=C(Nc1cnn2ccc(N3CCC[C@@H]3c3cc(F)ccc3Cl)nc12)N1CC[C@@H](O)C1]

(R)—N-(5-((R)-2-(2-chloro-5-fluorophenyl)pyrrolidin-1-yl)pyrazolo[1,5-a]pyrimidin-3-yl)-3-hydroxypyrrolidine-1-carboxamide To a DCM (0.8 mL) solution of (R)-5-(2-(2-chloro-5-fluorophenyl)pyrrolidin-1-yl)pyrazolo[1,5-a]pyrimidin-3-amine (10 mg, 0.030 mmol, prepared as described in Example 8) was added CDI (10 mg, 0.06 mmol) at ambient temperature in one portion. After stirring two hours, (S)-pyrrolidin-3-ol (5 mg, 0.06 mmol) was added in one portion. The reaction was stirred at ambient temperature for 20 hours before it was concentrated and directly purified by reverse-phase column chromatography, eluting with 5 to 50% acetonitrile/water to yield the final product as a solid (9 mg, 67% yield). MS (apci) m/z=445.2 (M+H).

Example 42

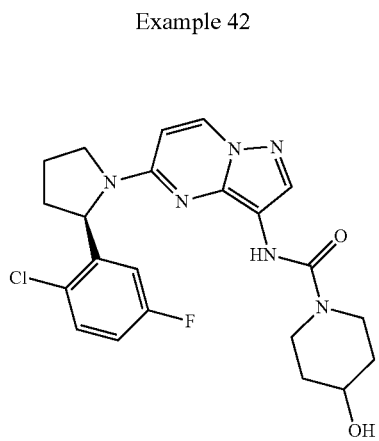

(R)—N-(5-(2-(2-chloro-5-fluorophenyl)pyrrolidin-1-yl)pyrazolo[1,5-a]pyrimidin-3-yl)-4-hydroxypiperidine-1-carboxamide Prepared by the method as described in Example 41, substituting (S)-pyrrolidin-3-ol with piperidin-4-ol, giving the final product as a solid (8 mg, 60%). MS (apci) m/z=459.2 (M+H).

Example 43

(R)—N-(5-((R)-2-(2-chloro-5-fluorophenyl)pyrrolidin-1-yl)pyrazolo[1,5-a]pyrimidin-3-yl)-3-hydroxypiperidine-1-carboxamide Prepared by the method as described in Example 41, substituting (S)-pyrrolidin-3-ol with (R)-piperidin-3-ol hydrochloride (followed by addition of 3 equivalents of DIEA), giving the final product as a solid (9.4 mg, 69%). MS (apci) m/z=459.1 (M+H).

Example 44

(S)—N-(5-((R)-2-(2-chloro-5-fluorophenyl)pyrrolidin-1-yl)pyrazolo[1,5-a]pyrimidin-3-yl)-3-hydroxypiperidine-1-carboxamide Prepared by the method as described in Example 41, substituting (S)-pyrrolidin-3-ol with (S)-piperidin-3-ol hydrochloride (followed by addition of 3 equivalents of DIEA), giving the final product as a solid (9.3 mg, 68%). MS (apci) m/z=459.2 (M+H).

Example 45

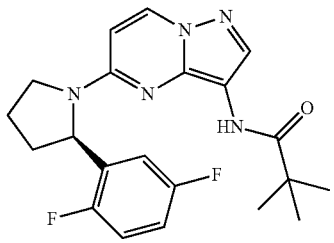 [SMILES: CC(C)(C)C(=O)Nc1cnn2ccc(N3CCC[C@@H]3c3cc(F)ccc3F)nc12]

(R)—N-(5-(2-(2,5-difluorophenyl)pyrrolidin-1-yl)pyrazolo[1,5-a]pyrimidin-3-yl)pivalamide A DCM (0.5 mL) solution of (R)-5-(2-(2,5-difluorophenyl)pyrrolidin-1-yl)pyrazolo[1,5-a]pyrimidin-3-amine (Preparation B; 20 mg, 0.063 mmol) was cooled in an ice bath, followed by addition of pivalic anhydride (26 mg, 0.14 mmol) and pyridine (12 mg, 0.14 mmol) drop-wise. The reaction was allowed to warm up to ambient temperature and stirred for 1 hour. The reaction mixture was directly purified by reverse-phase column chromatography, eluting with 5 to 65% acetonitrile/water to yield the final product as a yellowish foamy solid (19 mg, 75%). MS (apci) m/z=400.2 (M+H).

Example 46

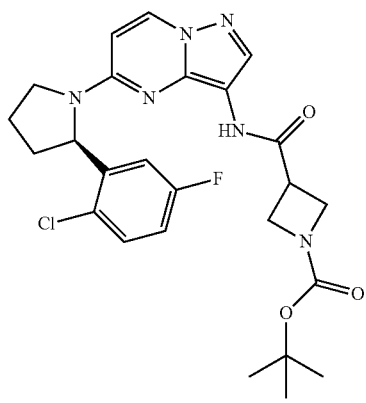 [SMILES: CC(C)(C)OC(=O)N1CC(C(=O)Nc2cnn3ccc(N4CCC[C@@H]4c4cc(F)ccc4Cl)nc23)C1]

(R)-tert-butyl 3-(5-(2-(2-chloro-5-fluorophenyl)pyrrolidin-1-yl)pyrazolo[1,5-a]pyrimidin-3-ylcarbamoyl)azetidine-1-carboxylate To a mixture of (R)-5-(2-(2-chloro-5-fluorophenyl)pyrrolidin-1-yl)pyrazolo[1,5-a]pyrimidin-3-amine (Example 8, Step A; 20 mg, 0.06 mmol), 1-(tert-butoxycarbonyl)azetidine-3-carboxylic acid (15 mg, 0.072 mmol), and HATU (28 mg, 0.072 mmol) was added 0.6 mL acetonitrile to make a solution. After cooling in an ice bath for 10 minutes, DIEA (0.032 mL, 0.18 mmol) was added to the reaction drop-wise. The reaction was allowed to warm up to ambient temperature and stirred overnight. The reaction mixture was directly purified by reverse-phase column chromatography, eluting with 5 to 70% acetonitrile/water to yield the final product as an off-white solid (19 mg, 61% yield). MS (apci) m/z=515.0 (M+H).

Example 47

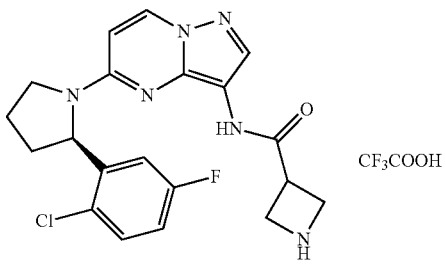 [SMILES: O=C(Nc1cnn2ccc(N3CCC[C@@H]3c3cc(F)ccc3Cl)nc12)C1CNC1 ; "CF3COOH"]

(R)—N-(5-(2-(2-chloro-5-fluorophenyl)pyrrolidin-1-yl)pyrazolo[1,5-a]pyrimidin-3-yl)azetidine-3-carboxamide trifluoroacetate To (R)-tert-butyl 3-(5-(2-(2-chloro-5-fluorophenyl)pyrrolidin-1-yl)pyrazolo[1,5-a]pyrimidin-3-ylcarbamoyl)azetidine-1-carboxylate (Example 46; 17 mg, 0.033 mmol), was added 0.5 mL 50% TFA solution in DCM and stirred at ambient temperature for 10 minutes. The reaction was concentrated, treated with ether, and filtered, giving the final product (TFA salt) as a fine beige powder (12 mg, 88% yield). MS (apci) m/z=415.2 (M+H).

Example 48

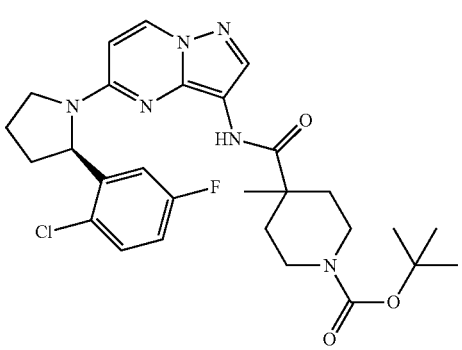 [SMILES: CC(C)(C)OC(=O)N1CCC(C)(C(=O)Nc2cnn3ccc(N4CCC[C@@H]4c4cc(F)ccc4Cl)nc23)CC1]

(R)-tert-butyl 4-(5-(2-(2-chloro-5-fluorophenyl)pyrrolidin-1-yl)pyrazolo[1,5-a]pyrimidin-3-ylcarbamoyl)-4-methylpiperidine-1-carboxylate To a mixture of (R)-5-(2-(2-chloro-5-fluorophenyl)pyrrolidin-1-yl)pyrazolo[1,5-a]pyrimidin-3-amine (Example 8, Step A; 25 mg, 0.075 mmol), 1-(tert-butoxycarbonyl)-4-methylpiperidine-4-carboxylic acid (22 mg, 0.090 mmol), and HATU (34 mg, 0.090 mmol) was added 0.6 mL DMF to make a solution. After cooling in an ice bath for 10 minutes, DIEA (0.039 mL, 0.23 mmol) was added to the reaction dropwise. The reaction was allowed to warm up to ambient temperature and stirred overnight. The reaction mixture was directly purified by reverse-phase column chromatography, eluting with 5 to 80% acetonitrile/water to yield the final product as a yellowish powder (28 mg, 67% yield). MS (apci) m/z=557.1 (M+H).

Example 49

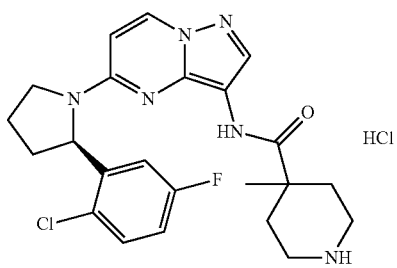 [SMILES: CC1(C(=O)Nc2cnn3ccc(N4CCC[C@@H]4c4cc(F)ccc4Cl)nc23)CCNCC1 ; Cl]

(R)—N-(5-(2-(2-chloro-5-fluorophenyl)pyrrolidin-1-yl)pyrazolo[1,5-a]pyrimidin-3-yl)-4-methylpiperidine-4-carboxamide hydrochloride To (R)-tert-butyl 4-(5-(2-(2-chloro-5-fluorophenyl)pyrrolidin-1-yl)pyrazolo[1,5-a]pyrimidin-3-ylcarbamoyl)-4-methylpiperidine-1-carboxylate (Example 48; 28 mg, 0.05 mmol), was added 1 mL 4 N HCl solution in dioxane and stirred at ambient temperature for 10 minutes. The reaction was concentrated, treated with ether, and filtered, giving the final product (HCl salt) as a fine beige powder. MS (apci) m/z=457.1 (M+H).

Example 50

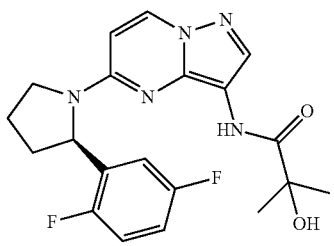 [SMILES: CC(C)(O)C(=O)Nc1cnn2ccc(N3CCC[C@@H]3c3cc(F)ccc3F)nc12]

(R)—N-(5-(2-(2,5-difluorophenyl)pyrrolidin-1-yl)pyrazolo[1,5-a]pyrimidin-3-yl)-2-hydroxy-2-methylpropanamide To a mixture of (R)-5-(2-(2,5-difluorophenyl)pyrrolidin-1-yl)pyrazolo[1,5-a]pyrimidin-3-amine (Preparation B; 25 mg, 0.079 mmol), 2-hydroxy-2-methylpropanoic acid (10 mg, 0.095 mmol), and HATU (36 mg, 0.095 mmol) was added 0.6 mL acetonitrile to make a solution. After cooling in an ice bath for 10 minutes, DIEA (0.041 mL, 0.24 mmol) was added to the reaction drop-wise. The reaction was allowed to warm up to ambient temperature and stirred overnight. The reaction mixture was concentrated, re-dissolved in methanol, and purified by reverse-phase column chromatography, eluting with 5 to 55% acetonitrile/water to yield the final product as an off-white solid (21 mg, 66% yield). MS (apci) m/z=402.2 (M+H).

Example 51

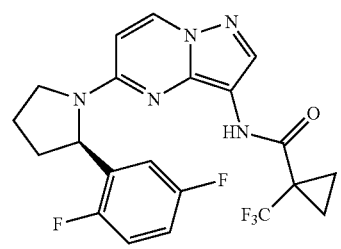 [SMILES: O=C(Nc1cnn2ccc(N3CCC[C@@H]3c3cc(F)ccc3F)nc12)C1(C(F)(F)F)CC1]

(R)—N-(5-(2-(2,5-difluorophenyl)pyrrolidin-1-yl)pyrazolo[1,5-a]pyrimidin-3-yl)-1-(trifluoromethyl)cyclopropane carboxamide To a mixture of (R)-5-(2-(2,5-difluorophenyl)pyrrolidin-1-yl)pyrazolo[1,5-a]pyrimidin-3-amine (Preparation B; 25 mg, 0.079 mmol), 1-(trifluoromethyl)cyclopropanecarboxylic acid (15 mg, 0.095 mmol), and HATU (36 mg, 0.095 mmol) was added 0.6 mL DMF to make a solution. After cooling in an ice bath for 10 minutes, DIEA (0.041 mL, 0.24 mmol) was added to the reaction drop-wise. The reaction was allowed to warm up to ambient temperature and stirred overnight. The reaction mixture was diluted with EtOAc (15 mL), washed with water and brine (5 mL each), concentrated, and purified by reverse-phase column chromatography, eluting with 5 to 72% acetonitrile/water to yield the final product as a beige solid (23 mg, 63% yield). MS (apci) m/z=452.2 (M+H).

Example 52

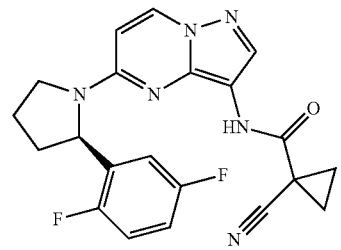 [SMILES: N#CC1(C(=O)Nc2cnn3ccc(N4CCC[C@@H]4c4cc(F)ccc4F)nc23)CC1]

(R)-1-cyano-N-(5-(2-(2,5-difluorophenyl)pyrrolidin-1-yl)pyrazolo[1,5-a]pyrimidin-3-yl)cyclopropanecarboxamide Prepared by the method as described in Example 51, substituting 1-(trifluoromethyl)cyclopropanecarboxylic acid with 1-cyanocyclopropanecarboxylic acid, to provide the final product as a white solid (18 mg, 56% yield). MS (apci) m/z=409.2 (M+H).

Example 53

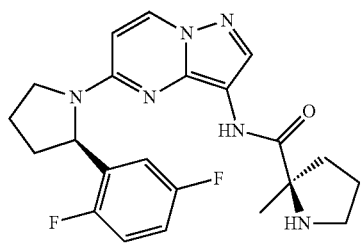 [SMILES: C[C@]1(C(=O)Nc2cnn3ccc(N4CCC[C@@H]4c4cc(F)ccc4F)nc23)CCCN1]

(R)—N-(5-((R)-2-(2,5-difluorophenyl)pyrrolidin-1-yl)pyrazolo[1,5-a]pyrimidin-3-yl)-2-methylpyrrolidine-2-carboxamide To a mixture of (R)-5-(2-(2,5-difluorophenyl)pyrrolidin-1-yl)pyrazolo[1,5-a]pyrimidin-3-amine (Preparation B; 25 mg, 0.079 mmol), (R)-1-(tert-butoxycarbonyl)-2-methylpyrrolidine-2-carboxylic acid (22 mg, 0.095 mmol), and HATU (36 mg, 0.095 mmol) was added 0.6 mL DMF to make a solution. After cooling in an ice bath for 10 minutes, DIEA (0.041 mL, 0.24 mmol) was added to the reaction drop-wise. The reaction was allowed to warm up to ambient temperature and stirred overnight. The reaction mixture was diluted with EtOAc (15 mL), washed with water and brine (5 mL each), concentrated, and purified by reverse-phase column chromatography, eluting with 5 to 68% acetonitrile/water to yield the N-Boc-protected product, (R)-tert-butyl 2-(5-((R)-2-(2,5-difluorophenyl)pyrrolidin-1-yl)pyrazolo[1,5-a]pyrimidin-3-ylcarbamoyl)-2-methylpyrrolidine-1-carboxylate, as a beige solid (32 mg, 73% yield). The de-protection was carried out by adding 1 mL 4 N HCl solution in dioxane to the above protected product. After 1 hour at ambient temperature, the reaction mixture was concentrated, treated with ether (1 mL), and filtered, giving the final product as an off-white solid. MS (apci) m/z=427.2 (M+H).

Example 54

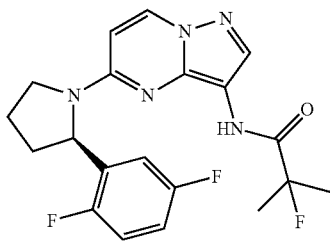 [SMILES: CC(C)(F)C(=O)Nc1cnn2ccc(N3CCC[C@@H]3c3cc(F)ccc3F)nc12]

(R)—N-(5-(2-(2,5-difluorophenyl)pyrrolidin-1-yl)pyrazolo[1,5-a]pyrimidin-3-yl)-2-fluoro-2-methyl-propanamide Prepared by the method as described in Example 51, substituting 1-(trifluoromethyl)-cyclopropane-carboxylic acid with 2-fluoro-2-methylpropanoic acid, to provide the final product as a pale-yellowish solid (25 mg, 77% yield). MS (apci) m/z=404.2 (M+H).

Example 55

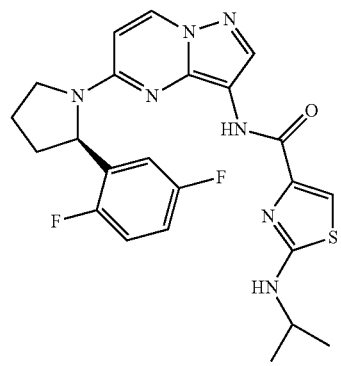 [SMILES: CC(C)Nc1nc(C(=O)Nc2cnn3ccc(N4CCC[C@@H]4c4cc(F)ccc4F)nc23)cs1]

(R)—N-(5-(2-(2,5-difluorophenyl)pyrrolidin-1-yl)pyrazolo[1,5-a]pyrimidin-3-yl)-2-(isopropylamino)thiazole-4-carboxamide Prepared by the method as described in Example 51, substituting 1-(trifluoromethyl)-cyclopropane-carboxylic acid with 2-(isopropylamino)thiazole-4-carboxylic acid hydrobromide, to provide the final product as a beige solid (34 mg, 89% yield). MS (apci) m/z=484.2 (M+H).

Example 56

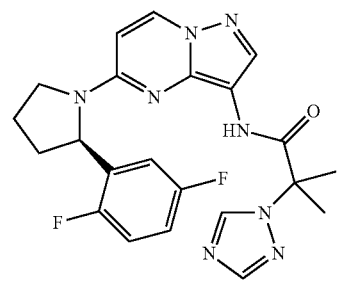 [SMILES: CC(C)(C(=O)Nc1cnn2ccc(N3CCC[C@@H]3c3cc(F)ccc3F)nc12)n1cncn1]

(R)—N-(5-(2-(2,5-difluorophenyl)pyrrolidin-1-yl)pyrazolo[1,5-a]pyrimidin-3-yl)-2-methyl-2-(1H-1,2,4-triazol-1-yl)propanamide Prepared by the method as described in Example 51, substituting 1-(trifluoromethyl)-cyclopropane-carboxylic acid with 2-methyl-2-(1H-1,2,4-triazol-1-yl)propanoic acid, to provide the final product as a pale-yellowish solid (26 mg, 72% yield). MS (apci) m/z=453.1 (M+H).

Example 57

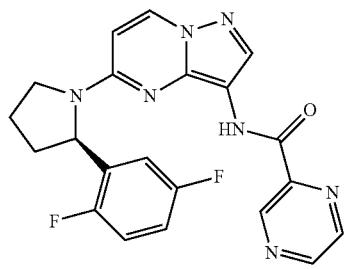

(R)—N-(5-(2-(2,5-difluorophenyl)pyrrolidin-1-yl)pyrazolo[1,5-a]pyrimidin-3-yl)pyrazine-2-carboxamide To a mixture of (R)-5-(2-(2,5-difluorophenyl)pyrrolidin-1-yl)pyrazolo[1,5-a]pyrimidin-3-amine (Preparation B; 25 mg, 0.079 mmol), pyrazine-2-carboxylic acid (12 mg, 0.095 mmol), and HATU (36 mg, 0.095 mmol) was added 0.6 mL DMF to make a solution. After cooling in an ice bath for 10 minutes, DIEA (0.041 mL, 0.24 mmol) was added to the reaction drop-wise. The reaction was allowed to warm up to ambient temperature and stirred for 10 minutes. The reaction mixture was diluted with EtOAc (15 mL), washed with water and brine (5 mL each), concentrated, and purified by reverse-phase column chromatography, eluting with 5 to 65% acetonitrile/water to yield the final product as a yellowish solid (31 mg, 93% yield). MS (apci) m/z=422.2 (M+H).

Example 58

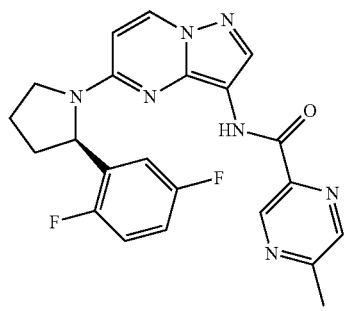 [SMILES: Cc1cnc(C(=O)Nc2cnn3ccc(N4CCC[C@@H]4c4cc(F)ccc4F)nc23)cn1]

(R)—N-(5-(2-(2,5-difluorophenyl)pyrrolidin-1-yl)pyrazolo[1,5-a]pyrimidin-3-yl)-5-methylpyrazine-2-carboxamide Prepared by the method as described in Example 57, substituting pyrazine-2-carboxylic acid with 5-methylpyrazine-2-carboxylic acid, to provide the final product as a yellowish solid (9 mg, 26% yield). MS (apci) m/z=436.2 (M+H).

Example 59

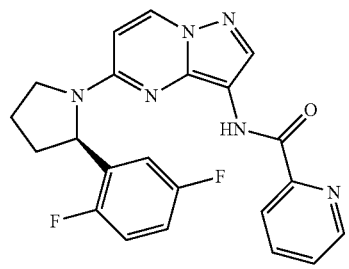 [SMILES: O=C(Nc1cnn2ccc(N3CCC[C@@H]3c3cc(F)ccc3F)nc12)c1ccccn1]

(R)—N-(5-(2-(2,5-difluorophenyl)pyrrolidin-1-yl)pyrazolo[1,5-a]pyrimidin-3-yl)picolinamide Prepared by the method as described in Example 57, substituting pyrazine-2-carboxylic acid with picolinic acid, to provide the final product as a yellowish solid (31 mg, 93% yield). MS (apci) m/z=421.2 (M+H).

Example 60

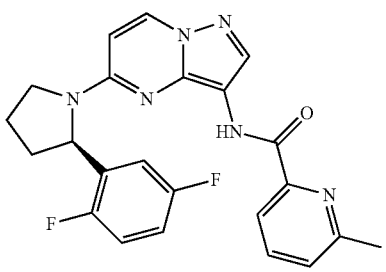 [SMILES: Cc1cccc(C(=O)Nc2cnn3ccc(N4CCC[C@@H]4c4cc(F)ccc4F)nc23)n1]

(R)—N-(5-(2-(2,5-difluorophenyl)pyrrolidin-1-yl)pyrazolo[1,5-a]pyrimidin-3-yl)-6-methylpicolinamide Prepared by the method as described in Example 57, substituting pyrazine-2-carboxylic acid with 6-methylpicolinic acid, to provide the final product as a yellowish solid (30 mg, 87% yield). MS (apci) m/z=435.2 (M+H).

Example 60A

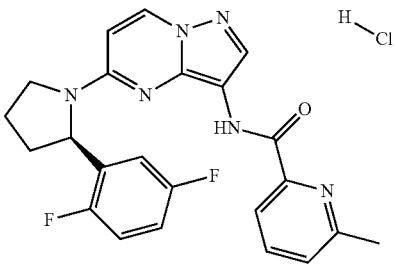 [SMILES: Cc1cccc(C(=O)Nc2cnn3ccc(N4CCC[C@@H]4c4cc(F)ccc4F)nc23)n1 ; Cl]

(R)—N-(5-(2-(2,5-difluorophenyl)pyrrolidin-1-yl) pyrazolo[1,5-a]pyrimidin-3-yl)-6-methylpicolinamide hydrochloride To a methanol (1 mL) solution of (R)—N-(5-(2-(2,5-difluorophenyl)pyrrolidin-1-yl)pyrazolo[1,5-a]pyrimidin-3-yl)-3-methylpicolinamide (10.3 mg, 0.0237 mmol) was added HCl as a solution is dioxane (30 μL). After 30 minutes, the reaction was concentrated to provide (R)—N-(5-(2-(2,5-difluorophenyl)pyrrolidin-1-yl)pyrazolo[1,5-a]pyrimidin-3-yl)-3-methylpicolinamide hydrochloride as a yellow solid.

Example 61

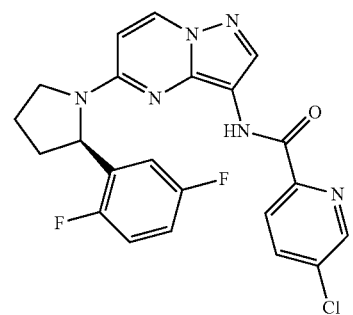 [SMILES: O=C(Nc1cnn2ccc(N3CCC[C@@H]3c3cc(F)ccc3F)nc12)c1ccc(Cl)cn1]

(R)-5-chloro-N-(5-(2-(2,5-difluorophenyl)pyrrolidin-1-yl)pyrazolo[1,5-a]pyrimidin-3-yl)picolinamide Prepared by the method as described in Example 57, substituting pyrazine-2-carboxylic acid with 5-chloropicolinic acid, to provide the final product as a yellowish solid (24 mg, 67% yield). MS (apci) m/z=455.2 (M+H).

Example 62

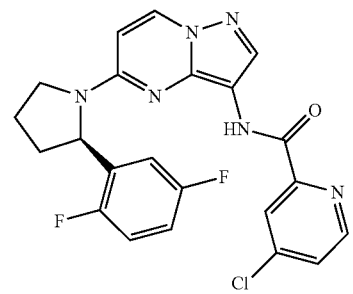 [SMILES: O=C(Nc1cnn2ccc(N3CCC[C@@H]3c3cc(F)ccc3F)nc12)c1cc(Cl)ccn1]

(R)-4-chloro-N-(5-(2-(2,5-difluorophenyl)pyrrolidin-1-yl)pyrazolo[1,5-a]pyrimidin-3-yl)picolinamide Prepared by the method as described in Example 57, substituting pyrazine-2-carboxylic acid with 4-chloropicolinic acid, to provide the final product as a beige solid (30 mg, 83% yield). MS (apci) m/z=455.2 (M+H).

Example 63

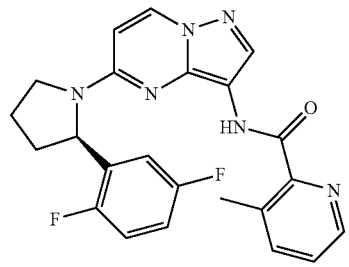 [SMILES: Cc1cccnc1C(=O)Nc1cnn2ccc(N3CCC[C@@H]3c3cc(F)ccc3F)nc12]

(R)—N-(5-(2-(2,5-difluorophenyl)pyrrolidin-1-yl) pyrazolo[1,5-a]pyrimidin-3-yl)-3-methylpicolinamide Prepared by the method as described in Example 57, substituting pyrazine-2-carboxylic acid with 3-methylpicolinic acid, to provide the final product as a beige solid (33 mg, 96% yield). MS (apci) m/z=435.2 (M+H).

Example 64

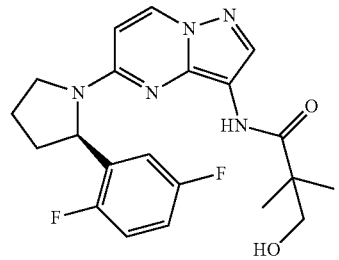 [SMILES: CC(C)(CO)C(=O)Nc1cnn2ccc(N3CCC[C@@H]3c3cc(F)ccc3F)nc12]

(R)—N-(5-(2-(2,5-difluorophenyl)pyrrolidin-1-yl) pyrazolo[1,5-a]pyrimidin-3-yl)-3-hydroxy-2,2-dimethylpropanamide Prepared by the method as described in Example 57, substituting pyrazine-2-carboxylic acid with 3-hydroxy-2,2-dimethylpropanoic acid, to provide the final product as a pale-yellowish solid (22 mg, 66% yield). MS (apci) m/z=416.2 (M+H).

Example 65

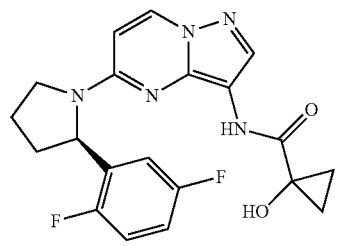 [SMILES: O=C(Nc1cnn2ccc(N3CCC[C@@H]3c3cc(F)ccc3F)nc12)C1(O)CC1]

(R)—N-(5-(2-(2,5-difluorophenyl)pyrrolidin-1-yl)
pyrazolo[1,5-a]pyrimidin-3-yl)-1-hydroxycyclopropanecarboxamide Prepared by the method as described in Example 57, substituting pyrazine-2-carboxylic acid with 1-hydroxycyclopropanecarboxylic acid, to provide the final product as a beige solid (6 mg, 16% yield). MS (apci) m/z=400.2 (M+H).

Example 66

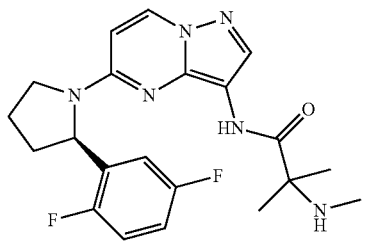 [SMILES: CNC(C)(C)C(=O)Nc1cnn2ccc(N3CCC[C@@H]3c3cc(F)ccc3F)nc12]

(R)—N-(5-(2-(2,5-difluorophenyl)pyrrolidin-1-yl)
pyrazolo[1,5-a]pyrimidin-3-yl)-2-methyl-2-(methylamino)propanamide Prepared by the method as described in Example 57, substituting pyrazine-2-carboxylic acid with 2-methyl-2-(methylamino)propanoic acid hydrochloride, to provide the final product as a solid (2 mg, 6% yield). MS (apci) m/z=415.1 (M+H).

Example 67

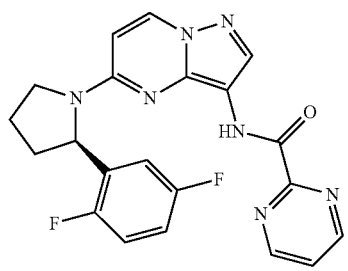 [SMILES: O=C(Nc1cnn2ccc(N3CCC[C@@H]3c3cc(F)ccc3F)nc12)c1ncccn1]

(R)—N-(5-(2-(2,5-difluorophenyl)pyrrolidin-1-yl)
pyrazolo[1,5-a]pyrimidin-3-yl)pyrimidine-2-carboxamide To a mixture of (R)-5-(2-(2,5-difluorophenyl)pyrrolidin-1-yl)pyrazolo[1,5-a]pyrimidin-3-amine (Preparation B; 25 mg, 0.079 mmol), pyrimidine-2-carboxylic acid (12 mg, 0.095 mmol), and HATU (36 mg, 0.095 mmol) was added 0.6 mL DMF. A few drops of DMSO were added to obtain a solution. After cooling in an ice bath for 10 minutes, DIEA (0.041 mL, 0.24 mmol) was added to the reaction drop-wise. The reaction was allowed to warm up to ambient temperature and stirred for one hour, then at 80° C. for 16 hours. Reaction did not reach completion before workup. The reaction mixture was diluted with EtOAc (15 mL), washed with water and brine (5 mL each), concentrated, and purified by reverse-phase column chromatography, eluting with 5 to 60% acetonitrile/water to yield the final product as a light yellowish solid (3 mg, 9% yield). MS (apci) m/z=422.2 (M+H).

Example 68

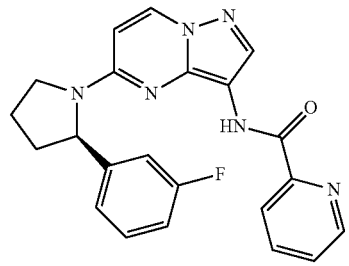 [SMILES: O=C(Nc1cnn2ccc(N3CCC[C@@H]3c3cccc(F)c3)nc12)c1ccccn1]

(R)—N-(5-(2-(3-fluorophenyl)pyrrolidin-1-yl)pyrazolo[1,5-a]pyrimidin-3-yl)picolinamide To a mixture of (R)-5-(2-(3-fluorophenyl)pyrrolidin-1-yl)pyrazolo[1,5-a]pyrimidin-3-amine (Example 6, Step A; 30 mg, 0.1 mmol), picolinic acid (15 mg, 0.12 mmol), and HATU (46 mg, 0.12 mmol) was added 0.7 mL DMF to make a solution. After cooling in an ice bath for 10 minutes, DIEA (0.053 mL, 0.3 mmol) was added to the reaction drop-wise. The reaction was allowed to warm up to ambient temperature and stirred for 10 minutes. The reaction mixture was diluted with EtOAc (15 mL), washed with water and brine (5 mL each), concentrated, and purified by reverse-phase column chromatography, eluting with 5 to 70% acetonitrile/water to yield the final product as a yellowish solid (35 mg, 86% yield). MS (apci) m/z=403.2 (M+H).

Example 69

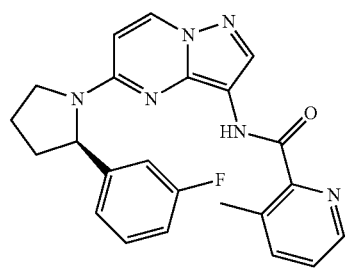 [SMILES: Cc1cccnc1C(=O)Nc1cnn2ccc(N3CCC[C@@H]3c3cccc(F)c3)nc12]

(R)—N-(5-(2-(3-fluorophenyl)pyrrolidin-1-yl)pyrazolo[1,5-a]pyrimidin-3-yl)-3-methylpicolinamide Prepared by the method as described in Example 68, substituting picolinic acid with 3-methylpicolinic acid, to provide the final product as a solid (35 mg, 83% yield). MS (apci) m/z=417.2 (M+H).

Example 70

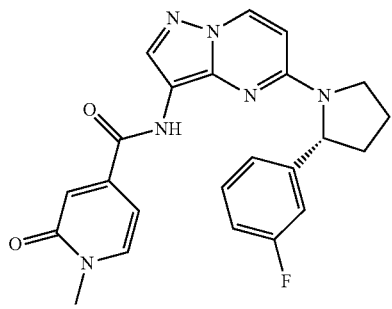 [SMILES: Cn1ccc(C(=O)Nc2cnn3ccc(N4CCC[C@@H]4c4cccc(F)c4)nc23)cc1=O]

(R)—N-(5-(2-(3-fluorophenyl)pyrrolidin-1-yl)pyrazolo[1,5-a]pyrimidin-3-yl)-1-methyl-2-oxo-1,2-dihydropyridine-4-carboxamide Prepared by the method as described in Example 68, substituting picolinic acid with 1-methyl-2-oxo-1,2-dihydropyridine-4-carboxylic acid, to provide the final product as a yellowish solid (18 mg, 41% yield). MS (apci) m/z=433.2 (M+H).

Example 71

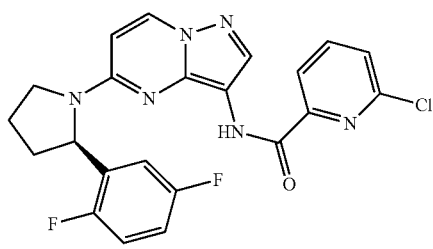 [SMILES: O=C(Nc1cnn2ccc(N3CCC[C@@H]3c3cc(F)ccc3F)nc12)c1cccc(Cl)n1]

(R)-6-chloro-N-(5-(2-(2,5-difluorophenyl)pyrrolidin-1-yl)pyrazolo[1,5-a]pyrimidin-3-yl)picolinamide Prepared by the method as described in Example 68, substituting (R)-5-(2-(3-fluorophenyl)pyrrolidin-1-yl)pyrazolo[1,5-a]pyrimidin-3-amine with (R)-5-(2-(2,5-difluorophenyl)pyrrolidin-1-yl)pyrazolo[1,5-a]pyrimidin-3-amine (Preparation B), and substituting picolinic acid with 6-chloropicolinic acid, to provide the final product as a yellowish solid (9.1 mg, 31% yield). MS (apci) m/z=455.2 (M+H).

Example 72

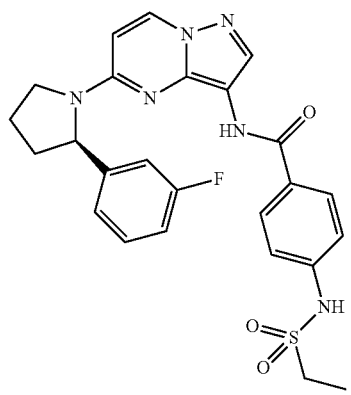 [SMILES: CCS(=O)(=O)Nc1ccc(C(=O)Nc2cnn3ccc(N4CCC[C@@H]4c4cccc(F)c4)nc23)cc1]

(R)-4-(ethylsulfonamido)-N-(5-(2-(3-fluorophenyl)pyrrolidin-1-yl)pyrazolo[1,5-a]pyrimidin-3-yl)benzamide Prepared by the method as described in Example 68, substituting picolinic acid with 4-(ethylsulfonamido)benzoic acid, to provide the final product as a yellowish solid (32 mg, 62% yield). MS (apci) m/z=509.2 (M+H).

Example 73

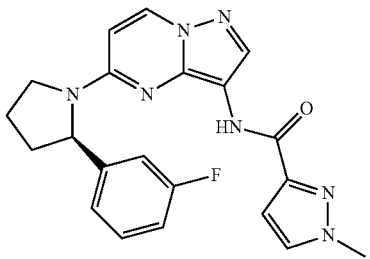 [SMILES: Cn1ccc(C(=O)Nc2cnn3ccc(N4CCC[C@@H]4c4cccc(F)c4)nc23)n1]

(R)—N-(5-(2-(3-fluorophenyl)pyrrolidin-1-yl)pyrazolo[1,5-a]pyrimidin-3-yl)-1-methyl-1H-pyrazole-3-carboxamide Prepared by the method as described in Example 68, substituting picolinic acid with 1-methyl-1H-pyrazole-3-carboxylic acid, to provide the final product as a yellowish solid (32 mg, 78% yield). MS (apci) m/z=406.3 (M+H).

Example 74

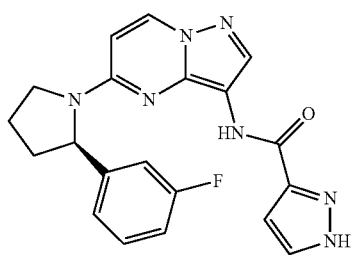 [SMILES: O=C(Nc1cnn2ccc(N3CCC[C@@H]3c3cccc(F)c3)nc12)c1cc[nH]n1]

(R)—N-(5-(2-(3-fluorophenyl)pyrrolidin-1-yl)pyrazolo[1,5-a]pyrimidin-3-yl)-1H-pyrazole-3-carboxamide Prepared by the method as described in Example 68, substituting picolinic acid with 1H-pyrazole-3-carboxylic acid, to provide the final product as a yellowish solid (14 mg, 35% yield). MS (apci) m/z=392.2 (M+H).

Example 75

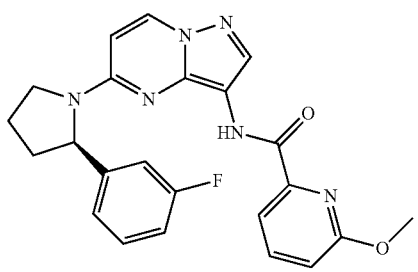 [SMILES: COc1cccc(C(=O)Nc2cnn3ccc(N4CCC[C@@H]4c4cccc(F)c4)nc23)n1]

(R)—N-(5-(2-(3-fluorophenyl)pyrrolidin-1-yl)pyrazolo[1,5-a]pyrimidin-3-yl)-6-methoxypicolinamide Prepared by the method as described in Example 68, substituting picolinic acid with 6-methoxypicolinic acid, to provide the final product as a yellowish solid (28 mg, 64% yield). MS (apci) m/z=433.2 (M+H).

Example 75A

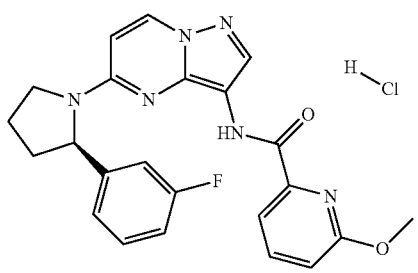 [SMILES: COc1cccc(C(=O)Nc2cnn3ccc(N4CCC[C@@H]4c4cccc(F)c4)nc23)n1 ; Cl]

(R)—N-(5-(2-(3-fluorophenyl)pyrrolidin-1-yl)pyrazolo[1,5-a]pyrimidin-3-yl)-6-methoxypicolinamide hydrochloride To a methanol (1 mL) solution of (R)—N-(5-(2-(3-fluorophenyl)pyrrolidin-1-yl)pyrazolo[1,5-a]pyrimidin-3-yl)-6-methoxypicolinamide (10.1 mg, 0.0234 mmol) was added HCl as a solution is dioxane (30 μL). After 30 minutes, the reaction was concentrated to provide (R)—N-(5-(2-(3-fluorophenyl)pyrrolidin-1-yl)pyrazolo[1,5-a]pyrimidin-3-yl)-6-methoxypicolinamide hydrochloride as a yellow solid.

Example 76

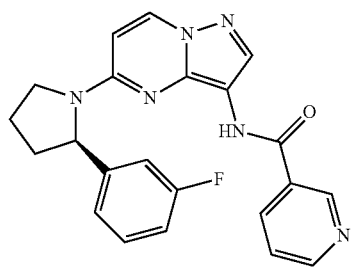 [SMILES: O=C(Nc1cnn2ccc(N3CCC[C@@H]3c3cccc(F)c3)nc12)c1cccnc1]

(R)—N-(5-(2-(3-fluorophenyl)pyrrolidin-1-yl)pyrazolo[1,5-a]pyrimidin-3-yl)nicotinamide To a mixture of (R)-5-(2-(3-fluorophenyl)pyrrolidin-1-yl)pyrazolo[1,5-a]pyrimidin-3-amine (Example 6, Step A; 30 mg, 0.1 mmol), nicotinic acid (25 mg, 0.2 mmol), and HATU (77 mg, 0.2 mmol) was added 0.7 mL DMF to make a solution. After cooling in an ice bath for 10 minutes, DIEA (0.053 mL, 0.3 mmol) was added to the reaction drop-wise. The reaction was allowed to warm up to ambient temperature and stirred for 3 hours. The reaction mixture was diluted with EtOAc (15 mL), washed with water and brine (5 mL each), concentrated, and purified by reverse-phase column chromatography, eluting with 5 to 57% acetonitrile/water to yield the final product as a yellowish solid (30 mg, 74% yield). MS (apci) m/z=403.2 (M+H).

Example 77

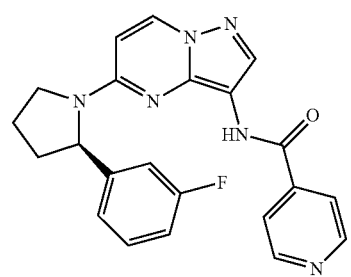 [SMILES: O=C(Nc1cnn2ccc(N3CCC[C@@H]3c3cccc(F)c3)nc12)c1ccncc1]

(R)—N-(5-(2-(3-fluorophenyl)pyrrolidin-1-yl)pyrazolo[1,5-a]pyrimidin-3-yl)isonicotinamide Prepared by the method as described in Example 76, substituting nicotinic acid with isonicotinic acid, to provide the final product as a yellowish solid (20 mg, 49% yield). MS (apci) m/z=403.2 (M+H).

Example 78

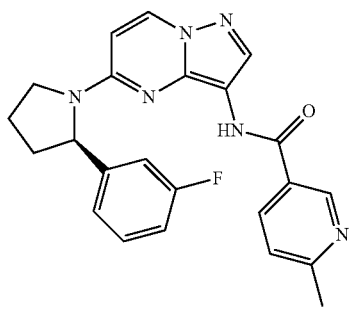 [SMILES: Cc1ccc(C(=O)Nc2cnn3ccc(N4CCC[C@@H]4c4cccc(F)c4)nc23)cn1]

(R)—N-(5-(2-(3-fluorophenyl)pyrrolidin-1-yl)pyrazolo[1,5-a]pyrimidin-3-yl)-6-methylnicotinamide Prepared by the method as described in Example 76, substituting nicotinic acid with 6-methylnicotinic acid, to provide the final product as a yellowish solid (27 mg, 64% yield). MS (apci) m/z=417.2 (M+H).

Example 79

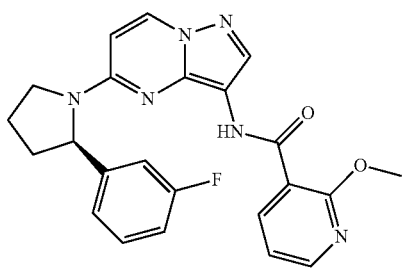 [SMILES: COc1ncccc1C(=O)Nc1cnn2ccc(N3CCC[C@@H]3c3cccc(F)c3)nc12]

(R)—N-(5-(2-(3-fluorophenyl)pyrrolidin-1-yl)pyrazolo[1,5-a]pyrimidin-3-yl)-2-methoxynicotinamide Prepared by the method as described in Example 76, substituting nicotinic acid with 2-methoxynicotinic acid, to provide the final product as a yellowish solid (32 mg, 73% yield). MS (apci) m/z=433.2 (M+H).

Example 80

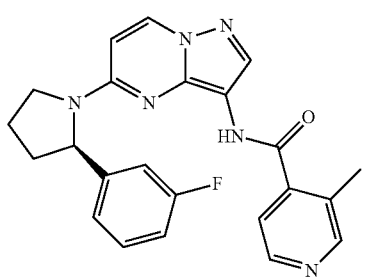 [SMILES: Cc1cnccc1C(=O)Nc1cnn2ccc(N3CCC[C@@H]3c3cccc(F)c3)nc12]

(R)—N-(5-(2-(3-fluorophenyl)pyrrolidin-1-yl)pyrazolo[1,5-a]pyrimidin-3-yl)-3-methylisonicotinamide Prepared by the method as described in Example 76, substituting nicotinic acid with 3-methylisonicotinic acid, to provide the final product as a yellowish solid (22 mg, 52% yield). MS (apci) m/z=417.2 (M+H).

Example 81

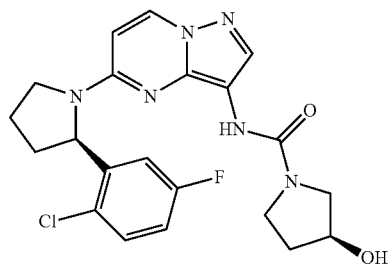 [SMILES: O=C(Nc1cnn2ccc(N3CCC[C@@H]3c3cc(F)ccc3Cl)nc12)N1CC[C@H](O)C1]

(S)—N-(5-((R)-2-(2-chloro-5-fluorophenyl)pyrrolidin-1-yl)pyrazolo[1,5-a]pyrimidin-3-yl)-3-hydroxy-pyrrolidine-1-carboxamide To a DCM (0.8 mL) solution of (R)-5-(2-(2-chloro-5-fluorophenyl)pyrrolidin-1-yl)pyrazolo[1,5-a]pyrimidin-3-amine (Example 8, Step A; 30 mg, 0.09 mmol) was added CDI (29 mg, 0.18 mmol) at ambient temperature in one portion. After stirring two hours, (S)-pyrrolidin-3-ol (15.8 mg, 0.181 mmol) was added in one portion. The reaction was stirred for 5 minutes before it was concentrated and directly purified by reverse-phase column chromatography, eluting with 5 to 53% acetonitrile/water to yield the final product as a yellowish foamy powder (33 mg, 81% yield). MS (apci) m/z=445.2 (M+H).

Example 82

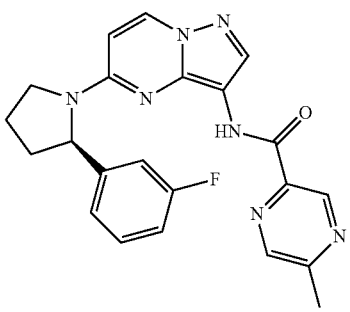 [SMILES: Cc1cnc(C(=O)Nc2cnn3ccc(N4CCC[C@@H]4c4cccc(F)c4)nc23)cn1]

(R)—N-(5-(2-(3-fluorophenyl)pyrrolidin-1-yl)pyrazolo[1,5-a]pyrimidin-3-yl)-5-methylpyrazine-2-carboxamide To a mixture of (R)-5-(2-(3-fluorophenyl)pyrrolidin-1-yl)pyrazolo[1,5-a]pyrimidin-3-amine (Example 6, Step A; 50 mg, 0.17 mmol, prepared as described in a previous example), 5-methylpyrazine-2-carboxylic acid (46 mg, 0.34 mmol), and HATU (128 mg, 0.34 mmol) was added 0.7 mL DMF to make a solution. After cooling in an ice bath for 10 minutes, DIEA (0.088 mL, 0.5 mmol) was added to the reaction drop-wise. The reaction was allowed to warm up to ambient temperature and stirred for 2 hours. The reaction mixture was directly filtered, rinsing with acetonitrile and then with ether, to provide the final product as a beige solid (44 mg, 63% yield). MS (apci) m/z=418.2 (M+H).

Example 83

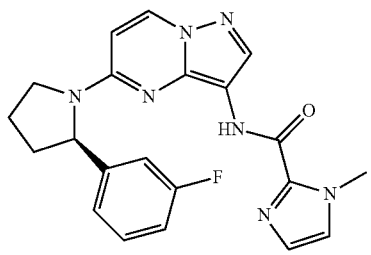 [SMILES: Cn1ccnc1C(=O)Nc1cnn2ccc(N3CCC[C@@H]3c3cccc(F)c3)nc12]

(R)—N-(5-(2-(3-fluorophenyl)pyrrolidin-1-yl)pyrazolo[1,5-a]pyrimidin-3-yl)-1-methyl-1H-imidazole-2-carboxamide To a mixture of (R)-5-(2-(3-fluorophenyl)pyrrolidin-1-yl)pyrazolo[1,5-a]pyrimidin-3-amine (Example 6, Step A; 40 mg, 0.13 mmol, prepared as described in a previous example), 1-methyl-1H-imidazole-2-carboxylic acid (34 mg, 0.27 mmol), and HATU (102 mg, 0.27 mmol) was added 1.0 mL DMF to make a solution. After cooling in an ice bath for 10 minutes, DIEA (0.07 mL, 0.4 mmol) was added to the reaction drop-wise. The reaction was allowed to warm up to ambient temperature and stirred for 10 minutes. The reaction mixture was diluted with EtOAc (15 mL), washed with water and brine (5 mL each), concentrated, and purified by reverse-phase column chromatography, eluting with 5 to 65% acetonitrile/water to yield the final product as a yellowish solid (37 mg, 68% yield). MS (apci) m/z=406.2 (M+H).

Example 84

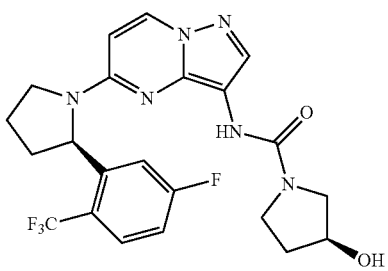 [SMILES: O=C(Nc1cnn2ccc(N3CCC[C@@H]3c3cc(F)ccc3C(F)(F)F)nc12)N1CC[C@H](O)C1]

(S)—N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide Step A: Preparation of (R)-5-(2-(5-fluoro-2-(trifluoromethyl)phenyl)pyrrolidin-1-yl)pyrazolo[1,5-a]pyrimidin-3-amine: Prepared according to Preparation B, substituting (R)-2-(2,5-difluorophenyl)pyrrolidine in Step 1 with (R)-2-(5-fluoro-2-(trifluoromethyl)phenyl)pyrrolidine.

Step B: Preparation of (R)-2-(5-fluoro-2-(trifluoromethyl)phenyl)pyrrolidine: Prepared by the method of Preparation A, substituting 2-bromo-1,4-difluorobenzene with 2-bromo-4-fluoro-1-(trifluoromethyl)benzene in Step A.

Step C: Preparation of (S)—N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide: To a DCM (1 mL) solution of (R)-5-(2-(5-fluoro-2-(trifluoromethyl)phenyl)pyrrolidin-1-yl)pyrazolo[1,5-a]pyrimidin-3-amine (25 mg, 0.068 mmol) was added CDI (22 mg, 0.14 mmol) at ambient temperature in one portion. After stirring for two hours, (S)-pyrrolidin-3-ol (18 mg, 0.21 mmol) was added in one portion. The reaction was stirred overnight before it was concentrated and directly purified by reverse-phase column chromatography, eluting with 0 to 60% acetonitrile/water to yield the final product as a yellowish solid (28 mg, 86% yield). MS (apci) m/z=479.2 (M+H).

Example 85

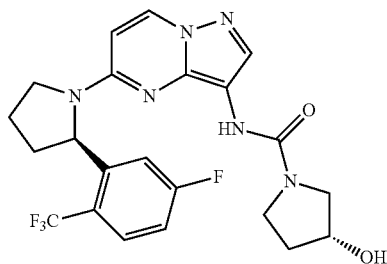 [SMILES: O=C(Nc1cnn2ccc(N3CCC[C@@H]3c3cc(F)ccc3C(F)(F)F)nc12)N1CC[C@@H](O)C1]

(R)—N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide Prepared by the method as described in Example 84, substituting (S)-pyrrolidin-3-ol in Step C with (R)-pyrrolidin-3-ol, giving the final product as a yellowish solid (26 mg, 79%). MS (apci) m/z=479.2 (M+H).

Example 86

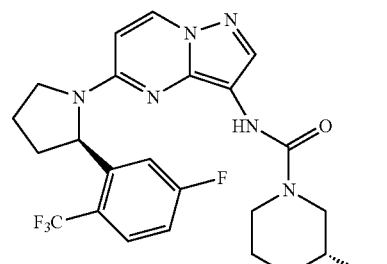

(R)—N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide Prepared by the method as described in Example 84, substituting (S)-pyrrolidin-3-ol in Step C with (R)-piperidin-3-ol, giving the final product as a yellowish solid (37 mg, 91%). MS (apci) m/z=493.2 (M+H).

Example 87

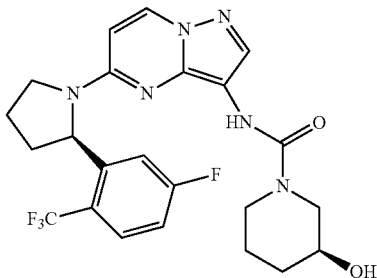 [SMILES: O=C(Nc1cnn2ccc(N3CCC[C@@H]3c3cc(F)ccc3C(F)(F)F)nc12)N1CCC[C@H](O)C1]

(S)—N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide Prepared by the method as described in Example 84, substituting (S)-pyrrolidin-3-ol in Step C with (S)-piperidin-3-ol, giving the final product as a yellowish solid (39 mg, 97%). MS (apci) m/z=493.2 (M+H).

Example 88

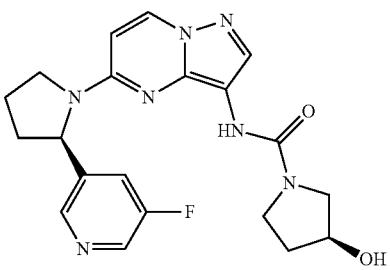 [SMILES: O=C(Nc1cnn2ccc(N3CCC[C@@H]3c3cncc(F)c3)nc12)N1CC[C@H](O)C1]

(S)—N-(5-((R)-2-(5-fluoropyridin-3-yl)pyrrolidin-1-yl)pyrazolo[1,5-a]pyrimidin-3-yl)-3-hydroxypyrrolidine-1-carboxamide Step A: Preparation of (R)-5-(2-(5-fluoropyridin-3-yl)pyrrolidin-1-yl)pyrazolo[1,5-a]pyrimidin-3-amine: Prepared according to Preparation B, substituting (R)-2-(2,5-difluorophenyl)pyrrolidine in Step 1 with (R)-3-fluoro-5-(pyrrolidin-2-yl)pyridine.

Step B: Preparation of (R)-3-fluoro-5-(pyrrolidin-2-yl)pyridine: Prepared by the method of Preparation A, substituting 2-bromo-1,4-difluorobenzene with 3-bromo-5-fluoropyridine in Step A.

Step C: Preparation of (S)—N-(5-((R)-2-(5-fluoropyridin-3-yl)pyrrolidin-1-yl)pyrazolo[1,5-a]pyrimidin-3-yl)-3-hydroxypyrrolidine-1-carboxamide: To a DCM (1 mL) solution of (R)-5-(2-(5-fluoropyridin-3-yl)pyrrolidin-1-yl)pyrazolo[1,5-a]pyrimidin-3-amine (25 mg, 0.084 mmol) was added CDI (27 mg, 0.17 mmol) at ambient temperature in one portion. After stirring for two hours, (S)-pyrrolidin-3-ol (15 mg, 0.17 mmol) was added in one portion. The reaction was stirred overnight before it was concentrated and directly purified by reverse-phase column chromatography, eluting with 0 to 40% acetonitrile/water to yield the final product as a solid (27 mg, 78% yield). MS (apci) m/z=412.2 (M+H).

Example 89

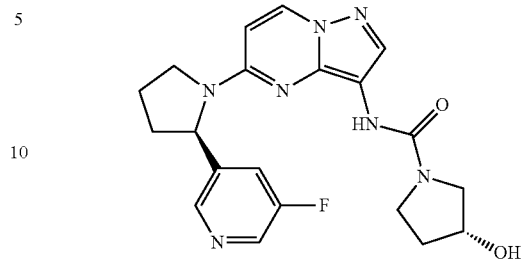

(R)—N-(5-((R)-2-(5-fluoropyridin-3-yl)pyrrolidin-1-yl)pyrazolo[1,5-a]pyrimidin-3-yl)-3-hydroxypyrrolidine-1-carboxamide Prepared by the method as described in Example 88, substituting (S)-pyrrolidin-3-ol in Step C with (R)-pyrrolidin-3-ol, giving the final product as a solid (28 mg, 81%). MS (apci) m/z=412.2 (M+H).

Example 90

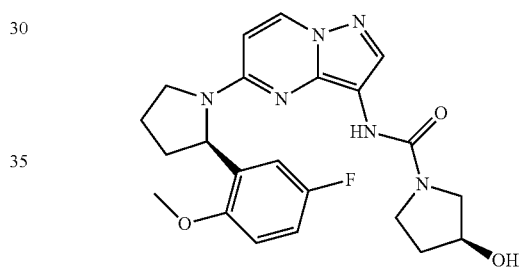

(S)—N-(5-(R)-2-(5-fluoro-2-methoxyphenyl)pyrrolidin-1-yl)pyrazolo[1,5-a]pyrimidin-3-yl)-3-hydroxypyrrolidine-1-carboxamide Step A: Preparation of (R)-5-(2-(5-fluoro-2-methoxyphenyl)pyrrolidin-1-yl)pyrazolo[1,5-a]pyrimidin-3-amine: Prepared according to Preparation B, substituting (R)-2-(2,5-difluorophenyl)pyrrolidine in Step 1 with (R)-2-(5-fluoro-2-methoxyphenyl)pyrrolidine.

Step B: Preparation of (R)-2-(5-fluoro-2-methoxyphenyl)pyrrolidine: Prepared by the method of Preparation A, substituting 2-bromo-1,4-difluorobenzene with 2-bromo-4-fluoro-1-methoxybenzene in Step A.

Step C: Preparation of (S)—N-(5-((R)-2-(5-fluoro-2-methoxyphenyl)pyrrolidin-1-yl)pyrazolo[1,5-a]pyrimidin-3-yl)-3-hydroxypyrrolidine-1-carboxamide: To a DCM (5 mL) solution of (R)-5-(2-(5-fluoro-2-methoxyphenyl)pyrrolidin-1-yl)pyrazolo[1,5-a]pyrimidin-3-amine (25 mg, 0.076 mmol) and DIEA (0.04 mL, 0.23 mmol) was added CDI (25 mg, 0.15 mmol) at ambient temperature in one portion. After stirring for one hour, (S)-pyrrolidin-3-ol (20 mg, 0.23 mmol) was added in one portion. The reaction was stirred overnight before it was concentrated and directly purified by reverse-phase column chromatography, eluting with 0 to 60% acetonitrile/water to yield the final product as a yellowish solid (28 mg, 83% yield). MS (apci) m/z=441.2 (M+H).

Example 91

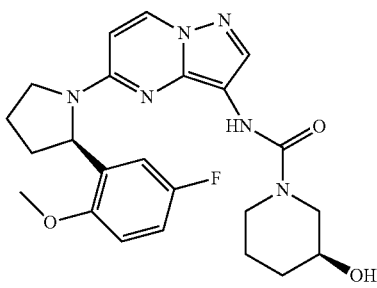 [SMILES: COc1ccc(F)cc1[C@H]1CCCN1c1ccn2ncc(NC(=O)N3CCC[C@H](O)C3)c2n1]

(S)—N-(5-((R)-2-(5-fluoro-2-methoxyphenyl)pyrrolidin-1-yl)pyrazolo[1,5-a]pyrimidin-3-yl)-3-hydroxypiperidine-1-carboxamide Prepared according to the method as described in Example 90, substituting (S)-pyrrolidin-3-ol in Step C with (S)-piperidin-3-ol, giving the final product as a yellowish solid. MS (apci) m/z=455.2 (M+H).

Example 92

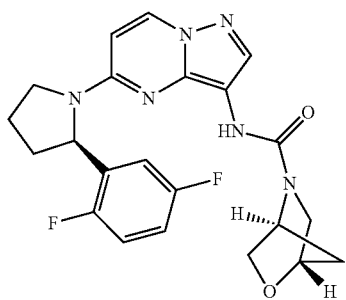 [SMILES: O=C(Nc1cnn2ccc(N3CCC[C@@H]3c3cc(F)ccc3F)nc12)N1C[C@@H]2C[C@H]1CO2]

(1S,4S)—N-(5-((R)-2-(2,5-difluorophenyl)pyrrolidin-1-yl)pyrazolo[1,5-a]pyrimidin-3-yl)-2-oxa-5-azabicyclo[2.2.1]heptane-5-carboxamide To a DCM (1.0 mL) solution of (R)-5-(2-(2,5-difluorophenyl)pyrrolidin-1-yl)pyrazolo[1,5-a]pyrimidin-3-amine (Preparation B; 50 mg, 0.16 mmol) was added CDI (51 mg, 0.32 mmol) at ambient temperature in one portion. After stirring 90 minutes, (1S,4S)-2-oxa-5-azabicyclo[2.2.1]heptane hydrochloride (43 mg, 0.32 mmol) was added in one portion, followed by DIEA (0.083 mL, 0.48 mmol). The reaction was stirred for 5 minutes before it was concentrated and directly purified by reverse-phase column chromatography, eluting with 0 to 60% acetonitrile/water to yield the final product as a pale-yellowish powder (60 mg, 86% yield). MS (apci) m/z=441.2 (M+H).

Example 93

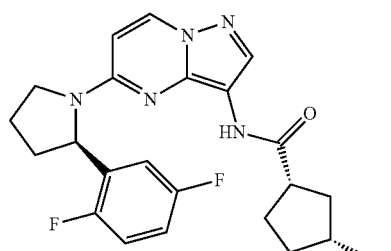

(R)—N-(5-((R)-2-(2,5-difluorophenyl)pyrrolidin-1-yl)pyrazolo[1,5-a]pyrimidin-3-yl)-3-hydroxypyrrolidine-1-carboxamide Prepared by the method as described in Example 92, substituting (1S,4S)-2-oxa-5-azabicyclo[2.2.1]heptane hydrochloride with (R)-pyrrolidin-3-ol. The crude material was purified by reverse-phase column chromatography with 5 to 50% acetonitrile/water eluent, giving the final product as a solid (89 mg, 66% yield). MS (apci) m/z=429.2 (M+H).

Example 94

(1S,3R)—N-(5-((R)-2-(2,5-difluorophenyl)pyrrolidin-1-yl)pyrazolo[1,5-a]pyrimidin-3-yl)-3-hydroxycyclopentanecarboxamide A DMA (1 mL) solution of (R)-5-(2-(2,5-difluorophenyl)pyrrolidin-1-yl)pyrazolo[1,5-a]pyrimidin-3-amine (Preparation B; 50 mg, 0.16 mmol), (1S,3R)-3-hydroxycyclopentanecarboxylic acid (23 mg, 0.17 mmol) [purchased from AFID Therapeutics Inc.] and 2-(1H-benzo[d][1,2,3]triazol-1-yl)-1,1,3,3-tetramethyluronium tetrafluoroborate (TBTU) (56 mg, 0.17 mmol) was first cooled in an ice-water bath, then DIEA (0.083 mL, 0.48 mmol) was added to reaction drop-wise. Ice bath was then removed and the reaction was stirred at ambient temperature for 1 hour to reach completion. The reaction mixture was diluted with water (10 mL) and vacuum-filtered, yielding the crude product as a beige solid. The crude was purified by reverse phase column chromatography, eluting with 5 to 57% acetonitrile/water to yield the final product as a solid (20 mg, 30% yield). MS (apci) m/z=428.2 (M+H).

Example 95

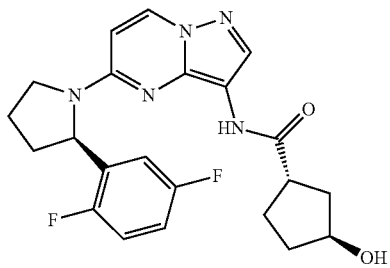 [SMILES: O=C(Nc1cnn2ccc(N3CCC[C@@H]3c3cc(F)ccc3F)nc12)[C@H]1CC[C@H](O)C1]

(1S,3S)—N-(5-((R)-2-(2,5-difluorophenyl)pyrrolidin-1-yl)pyrazolo[1,5-a]pyrimidin-3-yl)-3-hydroxycyclopentanecarboxamide Prepared by the same method as described in Example 94, substituting (1S,3R)-3-hydroxycyclopentane carboxylic acid with (1S,3S)-3-hydroxycyclopentanecarboxylic acid (23 mg, 0.17 mmol) [purchased from AFID Therapeutics Inc.] The crude product was purified by reverse phase column chromatography, eluting with 5 to 53% acetonitrile/water to yield the final product as a solid (35 mg, 52% yield). MS (apci) m/z=428.2 (M+H).

Example 96

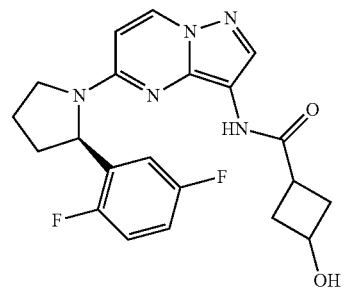 [SMILES: O=C(Nc1cnn2ccc(N3CCC[C@@H]3c3cc(F)ccc3F)nc12)C1CC(O)C1]

(R)—N-(5-(2-(2,5-difluorophenyl)pyrrolidin-1-yl)pyrazolo[1,5-a]pyrimidin-3-yl)-3-hydroxycyclobutanecarboxamide Prepared by the same method as described in Example 94, substituting (1S,3R)-3-hydroxycyclopentanecarboxylic acid with 3-hydroxycyclobutanecarboxylic acid (20 mg, 0.17 mmol) [purchased from Parkway Scientific]. The crude product was purified by reverse phase column chromatography, eluting with 5 to 53% acetonitrile/water to yield the final product as a solid (8 mg, 12% yield). MS (apci) m/z=414.2 (M+H).

Example 97

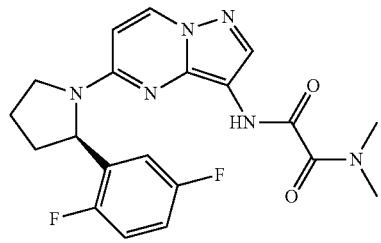 [SMILES: CN(C)C(=O)C(=O)Nc1cnn2ccc(N3CCC[C@@H]3c3cc(F)ccc3F)nc12]

(R)—$N^1$-(5-(2-(2,5-difluorophenyl)pyrrolidin-1-yl)pyrazolo[1,5-a]pyrimidin-3-yl)-$N^2$,$N^2$-dimethyloxalamide To a DCM (1 mL) solution of (R)-5-(2-(2,5-difluorophenyl)pyrrolidin-1-yl)pyrazolo[1,5-a]pyrimidin-3-amine (Preparation B; 50 mg, 0.16 mmol) was drop-wise added methyl 2-chloro-2-oxoacetate (19.4 mg, 0.159 mmol), followed by DIEA (0.0829 mL, 0.476 mmol). After the mild exothermal subsided and the reaction cooled back to ambient temperature, dimethylamine (0.8 mL, 1.6 mmol) [2M, THF] was added. The reaction was heated to gentle reflux for a few minutes, allowed to cool back to ambient temperature and stirred for 1 hour to reach completion. The reaction was concentrated and directly purified by reverse phase column chromatography, eluting with 5 to 60% acetonitrile/water to yield the final product as a pale-yellowish solid (48 mg, 73% yield). MS (apci) m/z=415.1 (M+H).

Example 98

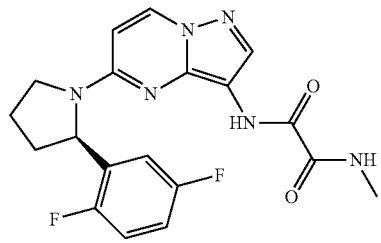 [SMILES: CNC(=O)C(=O)Nc1cnn2ccc(N3CCC[C@@H]3c3cc(F)ccc3F)nc12]

(R)—$N^1$-(5-(2-(2,5-difluorophenyl)pyrrolidin-1-yl)pyrazolo[1,5-a]pyrimidin-3-yl)-$N^2$-methyloxalamide Prepared by the same method as described in Example 97, substituting dimethylamine with methanamine (2M, THF), and the reaction was carried out at room temperature instead of at reflux. The crude product was purified by reverse phase column chromatography, eluting with 5 to 60% acetonitrile/water to yield the final product as a white solid (50 mg, 79% yield). MS (apci) m/z=401.1 (M+H).

Example 99

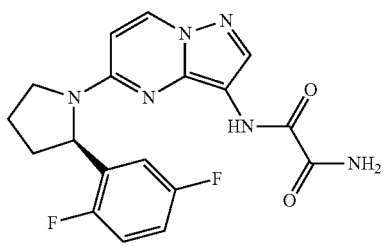 [SMILES: NC(=O)C(=O)Nc1cnn2ccc(N3CCC[C@@H]3c3cc(F)ccc3F)nc12]

(R)—N[1]-(5-(2-(2,5-difluorophenyl)pyrrolidin-1-yl)pyrazolo[1,5-a]pyrimidin-3-yl)oxalamide Prepared by the same method as described in Example 97, substituting dimethylamine with ammonia (7 M, methanol), and the reaction was carried out at 50° C. overnight. The crude product was purified by reverse phase column chromatography, eluting with 5 to 55% acetonitrile/water to yield the final product as a white solid (50 mg, 82% yield). MS (apci) m/z=387.1 (M+H).

Example 100

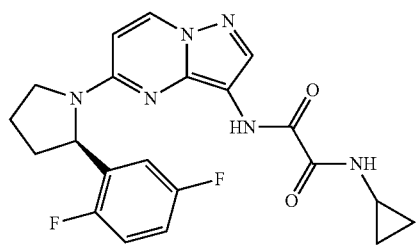 [SMILES: O=C(Nc1cnn2ccc(N3CCC[C@@H]3c3cc(F)ccc3F)nc12)C(=O)NC1CC1]

(R)—N[1]-cyclopropyl-N2-(5-(2-(2,5-difluorophenyl)pyrrolidin-1-yl)pyrazolo[1,5-a]pyrimidin-3-yl)oxalamide Prepared by the same method as described in Example 97, substituting dimethylamine with cyclopropanamine, and the reaction was carried out at ambient temperature instead of at reflux. The crude product was purified by reverse phase column chromatography, eluting with 5 to 65% acetonitrile/water to yield the final product as a white solid (50 mg, 74% yield). MS (apci) m/z=427.2 (M+H).

Example 101

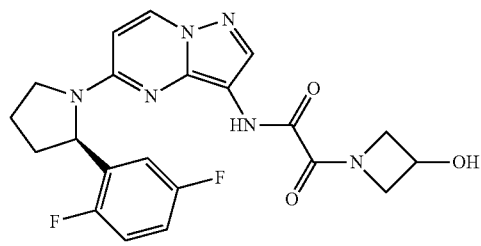 [SMILES: O=C(Nc1cnn2ccc(N3CCC[C@@H]3c3cc(F)ccc3F)nc12)C(=O)N1CC(O)C1]

(R)—N-(5-(2-(2,5-difluorophenyl)pyrrolidin-1-yl)pyrazolo[1,5-a]pyrimidin-3-yl)-2-(3-hydroxyazetidin-1-yl)-2-oxoacetamide Prepared by the same method as described in Example 97, substituting dimethylamine with azetidin-3-ol, and the reaction was carried out at 50° C. overnight. The crude product was purified by reverse phase column chromatography, eluting with 5 to 55% acetonitrile/water to yield the final product as a pale-yellowish solid (53 mg, 75% yield). MS (apci) m/z=443.1 (M+H).

Example 102

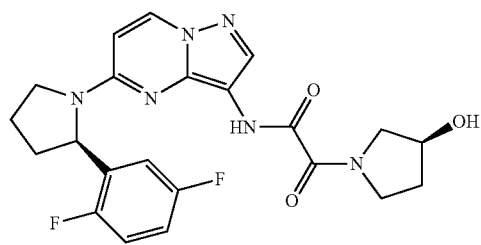 [SMILES: O=C(Nc1cnn2ccc(N3CCC[C@@H]3c3cc(F)ccc3F)nc12)C(=O)N1CC[C@H](O)C1]

N-(5-((R)-2-(2,5-difluorophenyl)pyrrolidin-1-yl)pyrazolo[1,5-a]pyrimidin-3-yl)-2-((S)-3-hydroxypyrrolidin-1-yl)-2-oxoacetamide Prepared by the same method as described in Example 97, substituting dimethylamine with (S)-pyrrolidin-3-ol, and the reaction was carried out at ambient temperature for 1 hour instead of at reflux. The crude product was purified by reverse phase column chromatography, eluting with 5 to 55% acetonitrile/water to yield the final product as a pale-yellowish solid (54 mg, 75% yield). MS (apci) m/z=457.2 (M+H).

Example 103

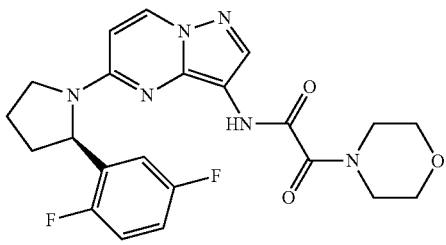 [SMILES: O=C(Nc1cnn2ccc(N3CCC[C@@H]3c3cc(F)ccc3F)nc12)C(=O)N1CCOCC1]

(R)—N-(5-(2-(2,5-difluorophenyl)pyrrolidin-1-yl)pyrazolo[1,5-a]pyrimidin-3-yl)-2-morpholino-2-oxoacetamide Prepared by the same method as described in Example 97, substituting dimethylamine with morpholine, and the reaction was carried out at 50° C. for 1 hour. The crude product was purified by reverse phase column chromatography, eluting with 5 to 60% acetonitrile/water to yield the final product as a pale-yellowish solid (52 mg, 72% yield). MS (apci) m/z=457.1 (M+H).

Example 104

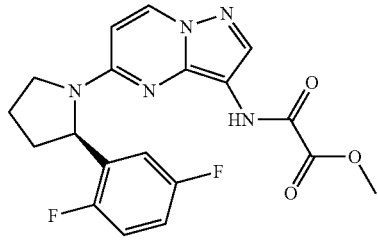 [SMILES: COC(=O)C(=O)Nc1cnn2ccc(N3CCC[C@@H]3c3cc(F)ccc3F)nc12]

(R)-methyl 2-(5-(2-(2,5-difluorophenyl)pyrrolidin-1-yl)pyrazolo[1,5-a]pyrimidin-3-ylamino)-2-oxoacetate A DCM (5 mL, 0.7928 mmol) solution of (R)-5-(2-(2,5-difluorophenyl)pyrrolidin-1-yl)pyrazolo[1,5-a]pyrimidin-3-amine (Preparation B; 250 mg, 0.7928 mmol) and DIEA (0.2071 mL, 1.189 mmol) was first cooled in an ice-water bath, then methyl 2-chloro-2-oxoacetate (0.07657 mL, 0.8325 mmol) was added to reaction drop-wise. Ice bath was removed and the reaction was stirred at ambient temperature for approx. 10 minutes to reach completion. The reaction was washed with 10% citric acid (aqueous). The aqueous layer was back-washed with DCM. The combined organic layer was washed with 1:1 water/brine, dried (Na₂SO₄) and concentrated. The crude oil residue was directly purified by silica chromatography, eluting with EtOAc/hexanes 1:1 to 2:1, yielding the final product as a pale-yellowish foamy powder (270 mg, 85% yield). MS (apci) m/z=402.2 (M+H).

Example 105

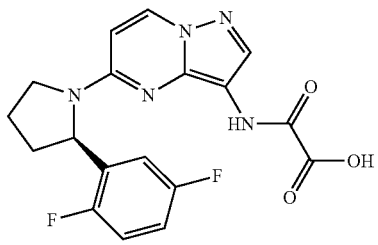 [SMILES: O=C(O)C(=O)Nc1cnn2ccc(N3CCC[C@@H]3c3cc(F)ccc3F)nc12]

(R)-2-(5-(2-(2,5-difluorophenyl)pyrrolidin-1-yl)pyrazolo[1,5-a]pyrimidin-3-ylamino)-2-oxoacetic acid (R)-methyl 2-(5-(2-(2,5-difluorophenyl)pyrrolidin-1-yl)pyrazolo[1,5-a]pyrimidin-3-ylamino)-2-oxoacetate (Example 104; 100 mg, 0.249 mmol) was dissolved in a mixture solvent of THF:MeOH:water (2:2:1, 1 mL), followed by addition of LiOH—H₂O (31.4 mg, 0.747 mmol). The reaction was stirred at ambient temperature for 10 minutes to reach completion. The reaction was concentrated, re-dissolved in water (20 mL) and acidified with 6 N HCl. The precipitate was vacuum-filtered, rinsed with water, heptane, and dried on high vacuum, giving the final product as a fine pale-yellowish powder (50 mg, 52% yield). MS (apci negative) m/z=386.1 (M−H).

What is claimed is:

1. A compound having the general formula I

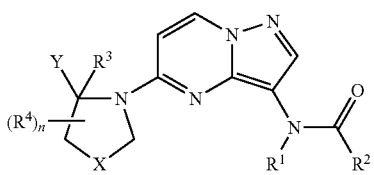

or a pharmaceutically acceptable salt thereof, wherein:
$R^1$ is H or (1-6C alkyl);
$R^2$ is $NR^bR^c$, (1-4C)alkyl, (1-4C)fluoroalkyl, $CF_3$, (1-4C)hydroxyalkyl, -(1-4C alkyl)hetAr¹, -(1-4C alkyl)NH₂, -(1-4C alkyl)NH(1-4C alkyl), -(1-4C allyl)N(1-4C alkyl)₂, hetAr², hetCyc¹, hetCyc², phenyl which is optionally substituted with NHSO₂(1-4C alkyl), (3-6C) cycloalkyl [which is optionally substituted with (1-4C alkyl), CN, OH, OMe, NH₂, NHMe, N(CH₃)₂, F, CF₃, CO₂(1-4C alkyl), or CO₂H], C(=O)NR$^e$R$^f$ or C(=O)OR$^g$;
$R^b$ is H or (1-6C alkyl);
$R^c$ is H, (1-4C)alkyl, (1-4C)hydroxyallyl, hetAr³, or phenyl, wherein said phenyl is optionally substituted with one or more substituents independently selected from halogen, CN, CF₃ and —O(1-4C alkyl),
or $NR^bR^c$ forms a 4 membered heterocyclic ring having a ring nitrogen atom, wherein said heterocyclic ring is optionally substituted with one or more substituents independently selected from halogen, OH, (1-4C alkyl), (1-4C)alkoxy, —OC(=O)(1-4C alkyl), NH₂, —NHC(=O)O(1-4C alkyl) and (1-4C)hydroxyalkyl, or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo, or NR$^b$R$^c$ forms a 7-8 membered bridged heterocyclic ring having a ring nitrogen atom and optionally having a second ring heteroatom selected from N and O, wherein said ring is optionally substituted with CO$_2$(1-4C alkyl);

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4C)alkoxy and NH(1-4C alkyl);

hetCyc$^1$ is a carbon-linked 4-6 membered azacyclic ring optionally substituted with one or more substituents independently selected from (1-4C alkyl), and CO$_2$(1-4C alkyl);

hetCyc$^2$ is a pyridinone or pyridazinone ring which is optionally substituted with a substituent selected from (1-4C)alkyl;

hetAr$^3$ is a 5-6 membered heteroaryl ring having 1-2 ring heteroatoms independently selected from N and O and optionally substituted with one or more substituents independently selected from (1-4C)alkyl;

R$^e$ is H or (1-4C)alkyl;

R$^f$ is H, (1-4C)alkyl, or (3-6C)cycloalkyl;

or NR$^e$R$^f$ forms a 4-6-membered azacyclic ring optionally having an additional ring heteroatom selected from N and O, wherein the azacyclic ring is optionally substituted with OH;

R$^g$ is H or (1-6C)alkyl;

Y is (i) phenyl optionally substituted with one or more substituents independently selected from halogen, (1-4C)alkoxy, CF$_3$ and CHF$_2$, or (ii) a pyridinyl ring, wherein said pyridinyl ring is optionally substituted with one or more halogen atoms;

X is —CH$_2$;

R$^3$ is H or (1-4C alkyl);

each R$^4$ is independently selected from halogen, (1-4C) alkyl, OH, (1-4C)alkoxy, NH$_2$, NH(1-4C alkyl) and CH$_2$OH; and n is 0, 1, 2, 3, 4, 5 or 6.

2. A compound of claim 1, wherein R$^2$ is NR$^b$R$^c$, (1-4C) alkyl, (1-4C)fluoroalkyl, CF$_3$, (1-4C)hydroxyallyl, -(1-4C alkyl)hetAr$^1$, -(1-4C alkyl)NH$_2$, -(1-4C alkyl)NH(1-4C alkyl), -(1-4C alkyl)N(1-4C alkyl)$_2$, hetAr$^2$, hetCyc$^1$, hetCyc$^2$, phenyl which is optionally substituted with NHSO$_2$(1-4C alkyl), or (3-6C)cycloalkyl which is optionally substituted with (1-4C alkyl), CN, OH, OMe, NH$_2$, NHMe, N(CH$_3$)$_2$, F, CF$_3$, CO$_2$(1-4C alkyl) or CO$_2$H.

3. A compound of claim 1, wherein R$^2$ is NR$^b$R$^c$.

4. A compound according to claim 1, wherein:
NR$^b$R$^c$ forms a 4 membered heterocyclic ring having a ring nitrogen atom, wherein said ring is optionally substituted with one or more substituents independently selected from halogen, OH, (1-4C alkyl), (1-4C)alkoxy, —OC(=O)(1-4C alkyl), NH$_2$, —NHC(=O)O(1-4C alkyl) and (1-4C)hydroxyalkyl, or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, CF$_3$, (1-4C)alkyl, CO$_2$(1-4C alkyl), CO$_2$H, NH$_2$, NHC(=O)O(1-4C alkyl) and oxo, or NR$^b$R$^c$ forms a 7-8 membered bridged heterocyclic ring having a ring nitrogen atom and optionally having a second ring heteroatom selected from N and O, wherein said ring is optionally substituted with CO$_2$(1-4C alkyl).

5. A compound according to claim 1, wherein:
R$^c$ is H, (1-4C)alkyl, (1-4C)hydroxyalkyl, hetAr$^3$, or phenyl, wherein said phenyl is optionally substituted with one or more substituents independently selected from halogen, CN, CF$_3$ and —O(1-4C alkyl).

6. A compound of claim 1, wherein R$^2$ is (1-4C)alkyl, (1-4C)fluoroalkyl, CF$_3$, -(1-4C alkyl)hetAr$^1$ or -(1-4C alkyl)NH(1-4C alkyl).

7. A compound of claim 1, wherein R$^2$ is hetAr$^2$, hetCyc$^1$ or hetCyc$^2$.

8. A compound of claim 1, wherein R$^2$ is phenyl optionally substituted with NHSO$_2$(1-4C alkyl).

9. A compound of claim 1, wherein R$^2$ is (3-6C)cycloalkyl which is optionally substituted with (1-4C alkyl), CN, OH, CF$_3$, CO$_2$(1-4C alkyl) or CO$_2$H.

10. A compound of claim 1, wherein R$^2$ is C(=O)NR$^e$R$^f$ or C(O)OR$^g$.

11. A compound according to claim 1, wherein Y is phenyl optionally substituted with one or more substituents independently selected from halogen, (1-4C)alkoxy, CF$_3$ and CHF$_2$.

12. A compound according to claim 11, wherein Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl or 3-chloro-5-fluorophenyl.

13. A compound according to claim 1, wherein Y is a pyridinyl ring, wherein said pyridinyl ring is optionally substituted with one or more halogen atoms.

14. A compound according to claim 1, wherein Y has the absolute configuration of FIG. Ia:

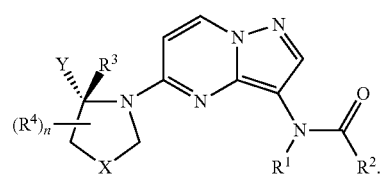

15. A compound according to claim 1, wherein R$^3$ is H.

16. A compound according to claim 1, wherein:
R$^1$ is H or (1-6C alkyl);
R$^2$ is NR$^b$R$^c$;
NR$^b$R$^c$ forms a 4 membered heterocyclic ring having a ring nitrogen atom, wherein said heterocyclic ring is optionally substituted with one or more substituents independently selected from halogen, OH, (1-4C alkyl), (1-4C) alkoxy, —OC(=O)(1-4C alkyl), NH$_2$, —NHC(=O)O (1-4C alkyl) and (1-4C)hydroxyalkyl, or NR$^b$R$^c$ forms a 5-6 membered heterocyclic ring having a ring heteroatom which is nitrogen and optionally having a second ring heteroatom or group selected from N, O and SO$_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo;

Y is phenyl optionally substituted with one or more substituents independently selected from halogen, (1-4C) alkoxy, $CF_3$ and $CHF_2$;

X is —$CH_2$;

$R^3$ is H or (1-4C alkyl);

each $R^4$ is independently selected from halogen, (1-4C) alkyl, OH, (1-4C)alkoxy, $NH_2$, NH(1-4C alkyl) and $CH_2OH$; and n is 0, 1, or 2.

17. A compound according to claim 16, wherein:

$R^1$ is H or (1-6C alkyl);

$R^2$ is $NR^bR^c$;

$NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, $NHC(=O)O$(1-4C alkyl) and oxo;

Y is phenyl optionally substituted with one or more substituents independently selected from halogen, (1-4C) alkoxy, $CF_3$ and $CHF_2$;

X is —$CH_2$—;

$R^3$ is H or (1-4C alkyl);

each $R^4$ is independently selected from halogen, (1-4C) alkyl, OH, (1-4C)alkoxy, $NH_2$, NH(1-4C alkyl) and $CH_2OH$; and n is 0, 1, or 2.

18. A compound according to claim 17, wherein the heterocyclic ring formed by $NR^bR^c$ is optionally substituted with one or two substituents independently selected from OH, F, $NH_2$, $CO_2H$, $CO_2Et$, $NHCO_2C(CH_3)_3$, $CF_3$, methyl, ethyl, isopropyl, $CO_2C(CH_2)_3$ and oxo.

19. A compound according to claim 18, wherein Y is phenyl optionally substituted with one or more halogen atoms.

20. A compound according to claim 19, wherein Y is phenyl optionally substituted with one or two fluorine atoms.

21. A compound according claim 16, wherein:

$R^1$ is H or (1-6C alkyl);

$R^2$ is $NR^bR^c$;

$NR^bR^c$ forms a 4 membered heterocyclic ring having a ring nitrogen atom, wherein said ring is optionally substituted with one or more substituents independently selected from halogen, OH, (1-4C alkyl), (1-4C)alkoxy, —OC(=O)(1-4C alkyl), $NH_2$, —NHC(=O)O(1-4C alkyl) and (1-4C)hydroxyalkyl;

Y is phenyl optionally substituted with one or more substituents independently selected from halogen, (1-4C) alkoxy, $CF_3$ and $CHF_2$;

X is —$CH_2$—;

$R^3$ is H or (1-4C alkyl);

each $R^4$ is independently selected from halogen, (1-4C) alkyl, OH, (1-4C)alkoxy, $NH_2$, NH(1-4C alkyl) and $CH_2OH$; and n is 0, 1, or 2.

22. A compound according to claim 21, wherein the heterocyclic ring formed by $NR^bR^c$ is optionally substituted with one or two substituents independently selected from F, OH, methyl, OMe, $OC(=O)C(CH_3)_2$, $NH_2$, —$NHC(=O)OC(CH_3)_3$ and $CH_2OH$.

23. A compound according to claim 22, wherein Y is phenyl optionally substituted with one or more halogen atoms.

24. A compound according to claim 23, wherein Y is phenyl optionally substituted with one or two fluorine atoms.

25. A compound according to claim 16, wherein n is zero or one.

26. A compound according to claim 25, wherein $R^3$ is hydrogen.

27. A compound according to claim 26, wherein $R^1$ is hydrogen.

28. A compound according to claim 1, which is a trifluoroacetate salt, a sulfate salt or a hydrochloride salt.

29. A compound according to claim 1, selected from:

(R)-N-(5-(2-(2,5-difluorophenyl)pyrrolidin-1-yl)pyrazolo[1,5-a]pyrimidin-3-yl)-3-hydroxyazetidine-1-carboxamide;

(R)-3-(5-(2-(2,5-difluorophenyl)pyrrolidin-1-yl)pyrazolo[1,5-a]pyrimidin-3-yl)-1,1-dimethylurea;

(R)-1-tert-butyl-3-(5-(2-(2,5-difluorophenyppyrrolidin-1-yl)pyrazolo[1,5-a]pyrimidin-3-yl)urea;

(R)-1-(5-(2-(2,5-difluorophenyl)pyrrolidin-1-yl)pyrazolo[1,5-a]pyrimidin-3-yl)-3-phenylurea;

(R)-N-(5-(2-(2,5-difluorophenyl)pyrrolidin-1-yl)pyrazolo[1,5-a]pyrimidin-3-yl)isobutyramide;

(R)-N-(5-(2-(3-fluorophenyl)pyrrolidin-1-yl)pyrazolo[1,5-a]pyrimidin-3-yl)-1-methyl-6-oxo-1,6-dihydropyridazine-3-carboxamide;

(R)-N-(5-(4,4-difluoro-2-(3-fluorophenyl)pyrrolidin-1-yl)pyrazolo[1,5-a]pyrimidin-3-yl)-3-hydroxyazetidine-1-carboxamide;

(R)-N-(5-(2-(2-chloro-5-fluorophenyl)pyrrolidin-1-yl)pyrazolo[1,5-a]pyrimidin-3-yl)-3-hydroxyazetidine-1-carboxamide;

(R)-N-(5-(2-(3-fluorophenyl)pyrrolidin-1-yl)pyrazolo[1,5-a]pyrimidin-3-yl)morpholine-4-carboxamide;

N-(5-(2-(3-fluorophenyl)-2-methylpyrrolidin-1-yl)pyrazolo[1,5-a]pyrimidin-3-yl)-3-hydroxyazetidine-1-carboxamide;

(R)-N-(5-(2-(3-chloro-5-fluorophenyl)pyrrolidin-1-yl)pyrazolo[1,5-a]pyrimidin-3-yl)-3-hydroxyazetidine-1-carboxamide;

(R)-N-(5-(2-(2-(difluoromethyl)-5-fluorophenyl)pyrrolidin-1-yl)pyrazolo[1,5-a]pyrimidin-3-yl)-3-hydroxyazetidine-1-carboxamide;

(R)-N-(5-(2-(2,5-difluorophenyl)pyrrolidin-1-yl)pyrazolo[1,5-a]pyrimidin-3-yl)morpholine-4-carboxamide;

(S)-N-(5-((R)-2-(2,5-difluorophenyl)pyrrolidin-1-yl)pyrazolo[1,5-a]pyrimidin-3-yl)-3-hydroxypyrrolidine-1-carboxamide;

(3R,4R)-N-(5-((R)-2-(2,5-difluorophenyl)pyrrolidin-1-yl)pyrazolo[1,5-a]pyrimidin-3-yl)-3,4-dihydroxypyrrolidine-1-carboxamide;

(R)-N-(5-(2-(2,5-difluorophenyl)pyrrolidin-1-yl)pyrazolo[1,5-a]pyrimidin-3-yl)-3-methoxyazetidine-1-carboxamide;

(R)-N-(5-(2-(2,5-difluorophenyl)pyrrolidin-1-yl)pyrazolo[1,5-a]pyrimidin-3-yl)-3-hydroxy-3-methylazetidine-1-carboxamide;

(R)-1-(5-(2-(2,5-difluorophenyl)pyrrolidin-1-yl)pyrazolo[1,5-a]pyrimidin-3-yl)-3-(4-fluorophenyl)urea;

(R)-1-(4-chlorophenyl)-3-(5-(2-(2,5-difluorophenyl)pyrrolidin-1-yl)pyrazolo[1,5-a]pyrimidin-3-yl)urea;

(R)-1-(5-(2-(2,5-difluorophenyl)pyrrolidin-1-yl)pyrazolo[1,5-a]pyrimidin-3-yl)-3-(4-methoxyphenyl)urea;

(R)-N-(5-(2-(2-chloro-5-fluorophenyl)pyrrolidin-1-yl)pyrazolo[1,5-a]pyrimidin-3-yl)-3-methoxyazetidine-1-carboxamide;

(R)-N-(5-(2-(2-chloro-5-fluorophenyl)pyrrolidin-1-yl)pyrazolo[1,5-a]pyrimidin-3-yl)-3-hydroxy-3-methylazetidine-1-carboxamide;

(R)-N-(5-(2-(2-chloro-5-fluorophenyl)pyrrolidin-1-yl)pyrazolo[1,5-a]pyrimidin-3-yl)morpholine-4-carboxamide;

(S)-tert-butyl 4-(5-((R)-2-(2-chloro-5-fluorophenyl)pyrrolidin-1-yl)pyrazolo[1,5-a]pyrimidin-3-ylcarbamoyl)-2-methylpiperazine-1-carboxylate;

(S)-N-(5-((R)-2-(2-chloro-5-fluorophenyl)pyrrolidin-1-yl)pyrazolo[1,5-a]pyrimidin-3-yl)-3-methylpiperazine-1-carboxamide;

(R)-N-(5-(2-(2,5-difluorophenyl)pyrrolidin-1-yl)pyrazolo[1,5-a]pyrimidin-3-yl)-4-isopropylpiperazine-1-carboxamide;

(R)-N-(5-(2-(2,5-difluorophenyl)pyrrolidin-1-yl)pyrazolo[1,5-a]pyrimidin-3-yl)-4-ethylpiperazine-1-carboxamide;

(R)-N-(5-(2-(2,5-difluorophenyl)pyrrolidin-1-yl)pyrazolo[1,5-a]pyrimidin-3-yl)-4-methylpiperazine-1-carboxamide;

N-(5-((R)-2-(2,5-difluorophenyl)pyrrolidin-1-yl)pyrazolo[1,5-a]pyrimidin-3-yl)-3,5-dimethylpiperazine-1-carboxamide;

(S)-tert-butyl 4-(5-((R)-2-(2,5-difluorophenyl)pyrrolidin-1-yl)pyrazolo[1,5-a]pyrimidin-3-ylcarbamoyl)-2-methylpiperazine-1-carboxylate;

(S)-N-(5-((R)-2-(2,5-difluorophenyl)pyrrolidin-1-yl)pyrazolo[1,5-a]pyrimidin-3-yl)-3-methylpiperazine-1-carboxamide hydrochloride;

(R)-N-(5-(2-(3-fluorophenyl)pyrrolidin-1-yl)pyrazolo[1,5-a]pyrimidin-3-yl)-3-hydroxyazetidine-1-carboxamide;

(R)-methyl 1-(5-(2-(2,5-difluorophenyl)pyrrolidin-1-yl)pyrazolo[1,5-a]pyrimidin-3-ylcarbamoyl)cyclopropanecarboxylate;

(R)-1-(5-(2-(2,5-difluorophenyl)pyrrolidin-1-yl)pyrazolo[1,5-a]pyrimidin-3-ylcarbamoyl)cyclopropanecarboxylic acid;

(S)-N-(5-((R)-2-(3-chloro-5-fluorophenyl)pyrrolidin-1-yl)pyrazolo[1,5-a]pyrimidin-3-yl)-3-hydroxypyrrolidine-1-carboxamide;

(R)-N-(5-((R)-2-(2-(difluoromethyl)-5-fluorophenyl)pyrrolidin-1-yl)pyrazolo[1,5-a]pyrimidin-3-yl)-3-hydroxypyrrolidine-1-carboxamide;

(S)-N-(5-((R)-2-(2-(difluoromethyl)-5-fluorophenyppyrrolidin-1-yl)pyrazolo[1,5-a]pyrimidin-3-yl)-3-hydroxypyrrolidine-1-carboxamide;

(R)-N-(5-(2-(2-(difluoromethyl)-5-fluorophenyl)pyrrolidin-1-yl)pyrazolo[1,5-a]pyrimidin-3-y1)-4-hydroxypiperidine-1-carboxamide;

(R)-N-(5-((R)-2-(2-(difluoromethyl)-5-fluorophenyl)pyrrolidin-1-yl)pyrazolo[1,5-a]pyrimidin-3-yl)-3-hydroxypiperidine-1-carboxamide;

(S)-N-(5-((R)-2-(2-(difluoromethyl)-5-fluorophenyl)pyrrolidin-1-yl)pyrazolo[1,5-a]pyrimidin-3-yl)-3-hydroxypiperidine-1-carboxamide;

(R)-N-(5-((R)-2-(2-chloro-5-fluorophenyl)pyrrolidin-1-yl)pyrazolo[1,5-a]pyrimidin-3-yl)-3-hydroxypyrrolidine-1-carboxamide;

(R)-N-(5-(2-(2-chloro-5-fluorophenyl)pyrrolidin-1-yl)pyrazolo[1,5-a]pyrimidin-3-yl)-4-hydroxypiperidine-1-carboxamide;

(R)-N-(5-((R)-2-(2-chloro-5-fluorophenyl)pyrrolidin-1-yl)pyrazolo[1,5-a]pyrimidin-3-yl)-3-hydroxypiperidine-1-carboxamide;

(S)-N-(5-((R)-2-(2-chloro-5-fluorophenyl)pyrrolidin-1-yl)pyrazolo[1,5-a]pyrimidin-3-yl)-3-hydroxypiperidine-1-carboxamide;

(R)-N-(5-(2-(2,5-difluorophenyl)pyrrolidin-1-yl)pyrazolo[1,5-a]pyrimidin-3-yl)pivalamide;

(R)-tert-butyl 3-(5-(2-(2-chloro-5-fluorophenyl)pyrrolidin-1-yl)pyrazolo[1,5-a]pyrimidin-3-ylcarbamoyl)azetidine-1-carboxylate;

(R)-N-(5-(2-(2-chloro-5-fluorophenyl)pyrrolidin-1-yl)pyrazolo[1,5-a]pyrimidin-3-yl)azetidine-3-carboxamide;

(R)-tert-butyl 4-(5-(2-(2-chloro-5-fluorophenyl)pyrrolidin-1-yl)pyrazolo[1,5-a]pyrimidin-3-ylcarbamoyl)-4-methylpiperidine-1-carboxylate;

(R)-N-(5-(2-(2-chloro-5-fluorophenyl)pyrrolidin-1-yl)pyrazolo[1,5-a]pyrimidin-3-yl)-4-methylpiperidine-4-carboxamide;

(R)-N-(5-(2-(2,5-difluorophenyl)pyrrolidin-1-yl)pyrazolo[1,5-a]pyrimidin-3-yl)-2-hydroxy-2-methylpropanamide;

(R)-N-(5-(2-(2,5-difluorophenyl)pyrrolidin-1-yl)pyrazolo[1,5-a]pyrimidin-3-yl)-1-(trifluoromethyl)cyclopropanecarboxamide;

(R)-1-cyano-N-(5-(2-(2,5-difluorophenyl)pyrrolidin-1-yl)pyrazolo[1,5-a]pyrimidin-3-yl)cyclopropanecarboxamide;

(R)-N-(5-((R)-2-(2,5-difluorophenyl)pyrrolidin-1-yl)pyrazolo[1,5-a]pyrimidin-3-yl)-2-methylpyrrolidine-2-carboxamide;

(R)-N-(5-(2-(2,5-difluorophenyl)pyrrolidin-1-yl)pyrazolo[1,5-a]pyrimidin-3-yl)-2-fluoro-2-methylpropanamide;

(R)-N-(5-(2-(2,5-difluorophenyl)pyrrolidin-1-yl)pyrazolo[1,5-a]pyrimidin-3-yl)-2-(isopropylamino)thiazole-4-carboxamide;

(R)-N-(5-(2-(2,5-difluorophenyl)pyrrolidin-1-yl)pyrazolo[1,5-a]pyrimidin-3-yl)-2-methyl-2-(1H-1,2,4-triazol-1-yl)propanamide;

(R)-N-(5-(2-(2,5-difluorophenyl)pyrrolidin-1-yl)pyrazolo[1,5-a]pyrimidin-3-yl)pyrazine-2-carboxamide;

(R)-N-(5-(2-(2,5-difluorophenyl)pyrrolidin-1-yl)pyrazolo[1,5-a]pyrimidin-3-yl)-5-methylpyrazine-2-carboxamide;

(R)-N-(5-(2-(2,5-difluorophenyl)pyrrolidin-1-yl)pyrazolo[1,5-a]pyrimidin-3-yl)picolinamide;

(R)-N-(5-(2-(2,5-difluorophenyl)pyrrolidin-1-yl)pyrazolo[1,5-a]pyrimidin-3-yl)-6-methylpicolinamide;

(R)-5-chloro-N-(5-(2-(2,5-difluorophenyl)pyrrolidin-1-yl)pyrazolo[1,5-a]pyrimidin-3-yl)picolinamide;

(R)-4-chloro-N-(5-(2-(2,5-difluorophenyl)pyrrolidin-1-yl)pyrazolo[1,5-a]pyrimidin-3-yl)picolinamide;

(R)-N-(5-(2-(2,5-difluorophenyl)pyrrolidin-1-yl)pyrazolo[1,5-a]pyrimidin-3-yl)-3-methylpicolinamide;

(R)-N-(5-(2-(2,5-difluorophenyl)pyrrolidin-1-yl)pyrazolo[1,5-a]pyrimidin-3-yl)-3-hydroxy-2,2-dimethylpropanamide;

(R)-N-(5-(2-(2,5-difluorophenyl)pyrrolidin-1-yl)pyrazolo[1,5-a]pyrimidin-3-yl)-1-hydroxycyclopropanecarboxamide;

(R)-N-(5-(2-(2,5-difluorophenyl)pyrrolidin-1-yl)pyrazolo[1,5-a]pyrimidin-3-yl)-2-methyl-2-(methylamino)propanamide;

(R)-N-(5-(2-(2,5-difluorophenyl)pyrrolidin-1-yl)pyrazolo[1,5-a]pyrimidin-3-yl)pyrimidine-2-carboxamide;

(R)-N-(5-(2-(3-fluorophenyl)pyrrolidin-1-yl)pyrazolo[1,5-a]pyrimidin-3-yl)picolinamide;

(R)-N-(5-(2-(3-fluorophenyl)pyrrolidin-1-yl)pyrazolo[1,5-a]pyrimidin-3-yl)-3-methylpicolinamide;

(R)-N-(5-(2-(3-fluorophenyl)pyrrolidin-1-yl)pyrazolo[1,5-a]pyrimidin-3-yl)-1-methyl-2-oxo-1,2-dihydropyridine-4-carboxamide;
(R)-6-chloro-N-(5-(2-(2,5-difluorophenyl)pyrrolidin-1-yl)pyrazolo[1,5-a]pyrimidin-3-yl)picolinamide;
(R)-4-(ethylsulfonamido)-N-(5-(2-(3-fluorophenyl)pyrrolidin-1-yl)pyrazolo[1,5-a]pyrimidin-3-yl)benzamide;
(R)-N-(5-(2-(3-fluorophenyl)pyrrolidin-1-yl)pyrazolo[1,5-a]pyrimidin-3-yl)-1-methyl-1H-pyrazole-3-carboxamide;
(R)-N-(5-(2-(3-fluorophenyl)pyrrolidin-1-yl)pyrazolo[1,5-a]pyrimidin-3-yl)-1H-pyrazole-3-carboxamide;
(R)-N-(5-(2-(3-fluorophenyl)pyrrolidin-1-yl)pyrazolo[1,5-a]pyrimidin-3-yl)-6-methoxypicolinamide;
(R)-N-(5-(2-(3-fluorophenyl)pyrrolidin-1-yl)pyrazolo[1,5-a]pyrimidin-3-yl)nicotinamide;
(R)-N-(5-(2-(3-fluorophenyl)pyrrolidin-1-yl)pyrazolo[1,5-a]pyrimidin-3-yl)isonicotinamide;
(R)-N-(5-(2-(3-fluorophenyl)pyrrolidin-1-yl)pyrazolo[1,5-a]pyrimidin-3-yl)-6-methylnicotinamide;
(R)-N-(5-(2-(3-fluorophenyl)pyrrolidin-1-yl)pyrazolo[1,5-a]pyrimidin-3-yl)-2-methoxynicotinamide;
(R)-N-(5-(2-(3-fluorophenyl)pyrrolidin-1-yl)pyrazolo[1,5-a]pyrimidin-3-yl)-3-methylisonicotinamide;
(S)-N-(5-((R)-2-(2-chloro-5-fluorophenyl)pyrrolidin-1-yl)pyrazolo[1,5-a]pyrimidin-3-yl)-3-hydroxypyrrolidine-1-carboxamide;
(R)-N-(5-(2-(3-fluorophenyl)pyrrolidin-1-yl)pyrazolo[1,5-a]pyrimidin-3-yl)-5-methylpyrazine-2-carboxamide;
(R)-N-(5-(2-(3-fluorophenyl)pyrrolidin-1-yl)pyrazolo[1,5-a]pyrimidin-3-yl)-1-methyl-1H-imidazole-2-carboxamide;
(S)-N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide;
(R)-N-(5-((R)-2-(5-fluoro-2-(trifluoromethyl)phenyl)pyrrolidin-1-yl)pyrazolo[1,5-a]pyrimidin-3-yl)-3-hydroxypyrrolidine-1-carboxamide;
(R)-N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide;
(S)-N-(5-((R)-2-(5-fluoro-2-(trifluoromethyl)phenyl)pyrrolidin-1-yl)pyrazolo[1,5-a]pyrimidin-3-yl)-3-hydroxypiperidine-1-carboxamide;
(S)-N-(5-((R)-2-(5-fluoropyridin-3-yl)pyrrolidin-1-yl)pyrazolo[1,5-a]pyrimidin-3-yl)-3-hydroxypyrrolidine-1-carboxamide;
(R)-N-(5-((R)-2-(5-fluoropyridin-3-yl)pyrrolidin-1-yl)pyrazolo[1,5-a]pyrimidin-3-yl)-3-hydroxypyrrolidine-1-carboxamide;
(S)-N-(5-((R)-2-(5-fluoro-2-methoxyphenyl)pyrrolidin-1-yl)pyrazolo[1,5-a]pyrimidin-3-yl)-3-hydroxypyrrolidine-1-carboxamide;
(S)-N-(5((R)-2-(5-fluoro-2-methoxypheny)pyrrolidin-1-yl)pyrazolo[1,5-a]pyrimidin-3-yl)-3-hydroxypiperidine-1-carboxamide;
(1S,4S)-N-(5-((R)-2-(2,5-difluorophenyl)pyrrolidin-1-yl)pyrazolo[1,5-a]pyrimidin-3-yl)-2-oxa-5-azabicyclo[2.2.1]heptane-5-carboxamide;
(R)-N-(5-((R)-2-(2,5-difluorophenyl)pyrrolidin-1-yl)pyrazolo[1,5-a]pyrimidin-3-yl)-3-hydroxypyrrolidine-1-carboxamide;
(1S,3R)-N-(5-((R)-2-(2,5-difluorophenyl)pyrrolidin-1-yl)pyrazolo[1,5-a]pyrimidin-3-yl)-3-hydroxycyclopentanecarboxamide;
(1S,3S)-N-(5-((R)-2-(2,5-difluorophenyl)pyrrolidin-1-yl)pyrazolo[1,5-a]pyrimidin-3-yl)-3-hydroxycyclopentanecarboxamide;
(R)-N-(5-(2-(2,5-difluorophenyl)pyrrolidin-1-yl)pyrazolo[1,5-a]pyrimidin-3-yl)-3-hydroxycyclobutanecarboxamide;
(R)-$N^1$-(5-(2-(2,5-difluorophenyl)pyrrolidin-1-yl)pyrazolo[1,5-a]pyrimidin-3-yl)-$N^2,N^2$-dimethyloxalamide;
(R)-$N^1$-(5-(2-(2,5-difluorophenyOpyrrolidin-1-yl)pyrazolo[1,5-a]pyrimidin-3-yl)-$N^2$-methyloxalamide;
(R)-$N^1$-(5-(2-(2,5-difluorophenyl)pyrrolidin-1-yl)pyrazolo[1,5-a]pyrimidin-3-yl)oxalamide;
(R)-$N^1$-cyclopropyl-N2-(5-(2-(2,5-difluorophenyl)pyrrolidin-1-yl)pyrazolo[1,5-a]pyrimidin-3-yl)oxalamide;
(R)-N-(5-(2-(2,5-difluorophenyl)pyrrolidin-1-yl)pyrazolo[1,5-a]pyrimidin-3-yl)-2-(3-hydroxyazetidin-1-yl)-2-oxoacetamide;
N-(5-((R)-2-(2,5-difluorophenyl)pyrrolidin-1-yl)pyrazolo[1,5-a]pyrimidin-3-yl)-2-((S)-3-hydroxypyrrolidin-1-yl)-2-oxoacetamide;
(R)-N-(5-(2-(2,5-difluorophenyl)pyrrolidin-1-yl)pyrazolo[1,5-a]pyrimidin-3-yl)-2-morpholino-2-oxoacetamide;
(R)-methyl 2-(5-(2-(2,5-difluorophenyl)pyrrolidin-1-yl)pyrazolo[1,5-a]pyrimidin-3-ylamino)-2-oxoacetate;
(R)-2-(5-(2-(2,5-difluorophenyl)pyrrolidin-1-yl)pyrazolo[1,5-a]pyrimidin-3-ylamino)-2-oxoacetic acid;
or a pharmaceutically acceptable salt thereof.

30. A pharmaceutical composition, which comprises a compound of Formula I as defined in claim 1, or a pharmaceutically acceptable salt thereof, and a pharmaceutically acceptable diluent or carrier.

* * * * *

UNITED STATES PATENT AND TRADEMARK OFFICE
CERTIFICATE OF CORRECTION

PATENT NO. : 8,513,263 B2  
APPLICATION NO. : 13/125263  
DATED : August 20, 2013  
INVENTOR(S) : Julia Haas et al.

It is certified that error appears in the above-identified patent and that said Letters Patent is hereby corrected as shown below:

IN THE CLAIMS

Column 99, Line 46, In Claim 1, delete "X is –$CH_2$" and insert -- X is –$CH_2$– --, therefor.

Column 99, Line 53, In Claim 2, delete "(1-4C)hydroxyallyl" and insert -- (1-4C)hydroxyalkyl --, therefor.

Column 100, Line 30, In Claim 10, delete "C(O)OR$^g$" and insert -- C(=O)OR$^g$ --, therefor.

Column 101, Line 8, In Claim 16, delete "X is –$CH_2$" and insert -- X is –$CH_2$– --, therefor.

Column 101, Line 38, In Claim 18, delete "$CO_2C(CH_2)_3$" and insert -- "$CO_2C(CH_3)_3$" --, therefor.

Column 101, Line 64, In Claim 22, delete "$OC(=O)C(CH_3)_2$" and insert -- $OC(=O)C(CH_3)_3$ --, therefor.

Column 102, Lines 16-17, In Claim 29, delete "(R)-1-tert-butyl-3-(5-(2-(2,5-difluorophenyppyrrolidin-1-yl)pyrazolo[1,5-a]pyrimidin-3-yl)urea" and insert -- (R)-1-tert-butyl-3-(5-(2-(2,5-difluorophenyl)pyrrolidin-1-yl)pyrazolo[1,5-a]pyrimidin-3-yl)urea --, therefor.

Column 103, Line 47, In Claim 29, delete "(S)-N-(5-((R)-2-(2-(difluoromethyl)-5-fluorophenyppyrrolidin-1-yl)pyrazolo[1,5-a]pyrimidin-3-yl)-3-hydroxypyrrolidine-l-carboxamide" and insert -- (S)-N-(5-((R)-2-(2-(difluoromethyl)-5-fluorophenyl)pyrrolidin-1-yl)pyrazolo[1,5-a]pyrimidin-3-yl)-3-hydroxypyrrolidine-l-carboxamide --, therefor.

Column 106, Line 4, In Claim 29, delete "(S)-N-(5((R)-2-(5-fluoro-2-methoxypheny)pyrrolidin-1-yl)pyrazolo[1,5-a]pyrimidin-3-yl)-3-hydroxypiperidine-1-carboxamide" and insert -- (S)-N-(5((R)-2-(5-fluoro-2-methoxyphenyl)pyrrolidin-1-yl)pyrazolo[1,5-a]pyrimidin-3-yl)-3-hydroxypiperidine-1-carboxamide --, therefor.

Signed and Sealed this  
Twenty-third Day of February, 2016

Michelle K. Lee  
*Director of the United States Patent and Trademark Office*